US012760376B2

(12) United States Patent
Li et al.

(10) Patent No.: US 12,760,376 B2

(45) Date of Patent: Oct. 13, 2026

(54) **DNAzyme FOR *Clostridium difficile* DETECTION**

(71) Applicant: McMaster University, Hamilton (CA)

(72) Inventors: Yingfu Li, Dundas (CA); Shuwen Qian, Hamilton (CA); Dingran Chang, Toronto (CA); Jimmy Gu, Mississauga (CA); Bruno Salena, Ancaster (CA)

(73) Assignee: McMaster University, Hamilton (CA)

( * ) Notice: Subject to any disclaimer, the term of this patent is extended or adjusted under 35 U.S.C. 154(b) by 344 days.

(21) Appl. No.: 18/642,242

(22) Filed: Apr. 22, 2024

(65) Prior Publication Data

US 2024/0352540 A1 Oct. 24, 2024

Related U.S. Application Data

(60) Provisional application No. 63/460,799, filed on Apr. 20, 2023.

(51) Int. Cl.

*C12Q 1/68* (2018.01)
*C12Q 1/6818* (2018.01)
*C12Q 1/689* (2018.01)

(52) U.S. Cl.

CPC ........... *C12Q 1/689* (2013.01); *C12Q 1/6818* (2013.01)

(58) Field of Classification Search

None

See application file for complete search history.

(56) References Cited

U.S. PATENT DOCUMENTS 9,624,551 B2 4/2017 Li et al.

OTHER PUBLICATIONS

Shen et al. (Angew. Chem. Int. Ed. 2016, 55, 2431-2434) (Year: 2016).*

Smits et al. Clostridium difficile infection. Author Manuscript. Nature Reviews Disease Primers, vol. 2 (16020), published Apr. 7, 2016, 47 pages.

Wiegand et al. Clinical and economic burden of Clostridium difficile infection in Europe: a systematic review of healthcare-facility-acquired infection. Journal of Hospital Infection, vol. 81, published online Apr. 11, 2012, pp. 1-14.

Ong et al. Clostridium difficile colitis: A clinical review. The American Journal of Surgery, vol. 213(3), published Mar. 2017, pp. 565-571.

Leffler and Lamont. Clostridium difficile Infection. The New England Journal of Medicine, vol. 372, published Apr. 16, 2015, pp. 1539-1548.

Martin et al. Clostridium difficile infection: advances in epidemiology, diagnosis and 2 understanding of transmission. Repository Copy. Nature Reviews Gastroenterology and Hepatology, vol. 13(4), published Mar. 9, 2016, 15 pages.

Czepiel et al. Clostridium difficile infection: review. European Journal of Clinical Microbiology & Infectious Diseases, vol. 38, published online Apr. 3, 2019, pp. 1211-1221.

Lessa et al. Burden of Clostridium difficile Infection in the United States. The New England Journal of Medicine, vol. 372, published Feb. 26, 2015, pp. 825-834.

Xia et al. Epidemiology of Clostridioides difficile infection in Canada: A six-year review to support vaccine decision-making. Canada Communicable Disease Report (CCDR), vol. 45, published Jul. 4, 2019, pp. 191-211.

Czepiel et al. Mortality Following Clostridioides difficile Infection in Europe: A Retrospective Multicenter Case-Control Study. Antibiotics, vol. 10(299), published Mar. 13, 2021, pp. 1-11.

Finn et al. Burden of Clostridioides difficile infection (CDI)—a systematic review of the epidemiology of primary and recurrent CDI. BMC Infectious Diseases, vol. 21(456), published online May 19, 2021, pp. 1-11.

Peng et al. Advances in the diagnosis and treatment of Clostridium difficile infections. Emerging Microbes & Infections, vol. 7(15), published online Feb. 7, 2018, pp. 1-14.

Jensen et al. Diagnosis of Clostridium difficile: real-time PCR detection of toxin genes in faecal samples is more sensitive compared to toxigenic culture. European Journal of Clinical Microbiology & Infectious Diseases, vol. 34, published online Nov. 25, 2014, pp. 727-736.

Solomon and Milner. ID Learning Unit: Understanding and Interpreting Testing for Clostridium difficile. Open Forum Infectious Diseases. Brief Report, published online May 16, 2014, 3 pages.

Kouhsari et al. Clostridium difficile infection: a review. Reviews in Medical Microbiology, vol. 29(3), published Apr. 2018, pp. 103-109.

Khan and Elzouki. Clostridium difficile infection: a review of the literature. Asian Pacific Journal of Tropical Medicine, vol. 7, published online Sep. 18, 2014, pp. S6-S13.

Longtin et al. Impact of the Type of Diagnostic Assay on Clostridium difficile Infection and Complication Rates in a Mandatory Reporting Program. Clinical Infectious Diseases, vol. 56(1), published online Sep. 25, 2012, pp. 67-73.

Liu et al. Selection and characterization of DNA aptamers for detection of glutamate dehydrogenase from Clostridium difficile. Biochimie, vol. 145, published online Sep. 4, 2017, pp. 151-157.

Liu et al. In Vitro Selection of Circular DNA Aptamers for Biosensing Applications. Angewandte Chemie, International Edition, vol. 58, published online May 8, 2019, pp. 8013-8017.

Liu et al. In Vitro Selection of a DNA Aptamer Targeting Degraded Protein Fragments for Biosensing. Angewandte Chemie, International Edition, vol. 59, published online Mar. 24, 2020, pp. 7706-7710.

Li et al. A Highly Specific DNA Aptamer for RNase H2 from Clostridium difficile. ACS Applied Materials and Interfaces, vol. 13, published Jan. 7, 2021, pp. 9464-9471.

Shen et al. A Catalytic DNA Activated by a Specific Strain of Bacterial Pathogen. Angewandte Chemie, vol. 55, published online Dec. 16, 2015, pp. 2477-2480.

(Continued)

*Primary Examiner* — Juliet C Switzer

(57) ABSTRACT

This disclosure relates to catalytic nucleic acids, catalytic nucleic acid probes, biosensors, and kits for detecting the presence of *Clostridium difficile*. Also provided are methods for detecting the presence of *Clostridium difficile* in a test sample, using the catalytic nucleic acids, catalytic nucleic acid probes, biosensors, and kits.

20 Claims, 17 Drawing Sheets

Specification includes a Sequence Listing.

(56) References Cited

OTHER PUBLICATIONS

Ellington and Szostak. In vitro selection of RNA molecules that bind specific ligands. Nature, vol. 346, published Aug. 30, 1990, pp. 818-822.
Tuerk and Gold. Systematic Evolution of Ligands by Exponential Enrichment: RNA Ligands to Bacteriophage T4 DNA Polymerase. Science, vol. 249, published Aug. 3, 1990, pp. 505-510.
Silverman. Survey and Summary. In vitro selection, characterization, and application of deoxyribozymes that cleave RNA. Nucleic Acids Research, vol. 33(19), published online Nov. 11, 2005, pp. 6151-6163.
Liu et al. Functional Nucleic Acid Sensors. Chemical Reviews, vol. 109(5), published online Mar. 20, 2009, pp. 1948-1998.
Schlosser and Li. Biologically Inspired Synthetic Enzymes Made from DNA. Chemistry & Biology, vol. 16, published Mar. 27, 2009, pp. 311-322.
Morrison et al. DNAzymes: Selected for Applications. Small Methods, vol. 2(1700319), published online Jan. 25, 2018, pp. 1-12.
McConnell et al. Biosensors Made of Synthetic Functional Nucleic Acids Toward Better Human Health. Analytical Chemistry, vol. 92, published Oct. 28, 2019, pp. 327-344.
McConnell et al. Biosensing with DNAzymes. Author manuscript. Chemical Society Reviews, vol. 50, published Aug. 21, 2021, 92 pages.
Liu et al. Screening, identification, and application of nucleic acid aptamers applied in food safety biosensing. Trends in Food Science & Technology, vol. 123, published online Mar. 30, 2022, pp. 355-375.
Huo et al. Recent advances on functional nucleic acid-based biosensors for detection of food contaminants. Talanta, vol. 222(121565), published online Aug. 26, 2020, pp. 1-12.
Chang et al. Functional Nucleic Acids for Pathogenic Bacteria Detection. Accounts of Chemical Research, vol. 54, published Sep. 3, 2021, pp. 3540-3549.
Cozma et al. DNAzymes as key components of biosensing systems for the detection of biological targets. Biosensors and Bioelectronics, vol. 177(112972), published online Jan. 8, 2021, pp. 1-13.
Liu et al. Discovery and Biosensing Applications of Diverse RNA-Cleaving DNAzymes. Accounts of Chemical Research, vol. 50, published Aug. 14, 2017, pp. 2273-2283.
Mei et al. An Efficient RNA-Cleaving DNA Enzyme that Synchronizes Catalysis with Fluorescence Signaling. Journal of the American Chemical Society, vol. 125(2), published Jan. 15, 2003, pp. 412-420.
Liu et al. Assemblage of Signaling DNA Enzymes with Intriguing Metal-lon Specificities and pH Dependences. Journal of the American Chemical Society, vol. 125(25), published Jun. 25, 2003, pp. 7539-7545.
Ali et al. Fluorogenic DNAzyme Probes as Bacterial Indicators. Angewandte Chemie, vol. 123, published online Mar. 15, 2011, pp. 3835-3838.
Ali et al. A DNAzyme-Based Colorimetric Paper Sensor for Helicobacter pylori. Angewandte Chemie, vol. 131, publsihed online Jun. 6, 2019, pp. 10012-10016.
Rothenbroker et al. Selection and Characterization of an RNA-Cleaving DNAzyme Activated by Legionella pneumophila. Angewandte Chemie, International Edition, vol. 60, published online Jan. 20, 2021, pp. 4782-4788.
Ali et al. A Lateral Flow Test for Staphylococcus aureus in Nasal Mucus Using a New DNAzyme as the Recognition Element. Angewandte Chemie, vol. 134(e202112346), published online Dec. 2, 2021, 5 pages.
Ali et al. A Simple DNAzyme-Based Fluorescent Assay for Klebsiella pneumoniae. Chembiochem, vol. 20, published online Feb. 11, 2019, pp. 906-910.
Schmieder and Edwards. Quality control and preprocessing of metagenomic datasets. Bioinformatics, vol. 27(6), Advance Access publication Jan. 28, 2011, pp. 863-864.
Li and Godzik. Cd-hit: a fast program for clustering and comparing large sets of protein or nucleotide sequences. Bioinformatics, vol. 22(13), Advance Access publication May 26, 2006, pp. 1658-1659.
Zhang et al. A Universal DNA Aptamer that Recognizes Spike Proteins of Diverse SARS-CoV-2 Variants of Concern. Chemistry—A European Journal, vol. 28(e202200078), published online Feb. 18, 2022, 7 pages.
Chang et al. An Unintentional Discovery of a Fluorogenic DNA Probe for Ribonuclease I. ChemBioChem, vol. 21, published online Oct. 21, 2019, pp. 464-468.
Monot et al. Clostridium difficile: New Insights into the Evolution of the Pathogenicity Locus. Scientific Reports, vol. 5 (15023), published Oct. 8, 2015, pp. 1-13.
Borriello. Pathogenesis of Clostridium difficile infection. Journal of Antimicrobial Chemotherapy, vol. 41, published May 1998, pp. 13-19.
Drudy et al. Toxin A-negative, toxin B-positive Clostridium difficile. International Journal of Infectious Diseases, vol. 11, published Jan. 2007, pp. 5-10.
McDonald et al. An Epidemic, Toxin Gene-Variant Strain of Clostridium difficile. The New England Journal of Medicine, vol. 353(23), published Dec. 8, 2005, pp. 2433-2441.
Loo et al. A Predominantly Clonal Multi-Institutional Outbreak of Clostridium difficile-Associated Diarrhea with High Morbidity and Mortality. The New England Journal of Medicine, vol. 353(23), published Dec. 8, 2005, pp. 2442-2449.
Miller et al. Health Care-Associated Clostridium difficile Infection in Canada: Patient Age and Infecting Strain Type Are Highly Predictive of Severe Outcome and Mortality. Clinical Infectious Diseases, vol. 50, published online Dec. 21, 2009, pp. 194-201.
Jiménez et al. Molecular epidemiology and antimicrobial resistance of Clostridium difficile in a national geriatric hospital in Costa Rica. Journal of Hospital Infection, vol. 99, published online Mar. 28, 2018, pp. 475-480.
Eyre et al. Two Distinct Patterns of Clostridium diffcile Diversity Across Europe Indicating Contrasting Routes of Spread. Clinical Infectious Diseases, vol. 67(7), published online Apr. 6, 2018, pp. 1035-1044.
Katz et al. The evolving epidemiology of Clostridium difficile infection in canadian hospitals during a postepidemic period (2009-2015). CMAJ, vol. 190(25), published Jun. 25, 2018, pp. E758-E765.
Goorhuis et al. Emergence of Clostridium difficile Infection Due to a New Hypervirulent Strain, Polymerase Chain Reaction Ribotype 078. Clinical Infectious Diseases, vol. 47, published Nov. 1, 2008, pp. 1162-1170.
Hensgens et al. Clostridium difficile infection in an endemic setting in the Netherlands. European Journal of Clinical Microbiology & Infectious Diseases, vol. 30, published online Dec. 31, 2010, pp. 587-593.
Bakker et al. Relatedness of Human and Animal Clostridium difficile PCR Ribotype 078 Isolates Determined on the Basis of Multilocus Variable-Number Tandem-Repeat Analysis and Tetracycline Resistance. Journal of Clinical Microbiology, vol. 48, published Oct. 2010, pp. 3744-3749.
Wehrhahn et al. A series of three cases of severe Clostridium difficile infection in Australia associated with a binary toxin producing clade 2 ribotype 251 strain. Anaerobe, vol. 55, published online Nov. 27, 2018, pp. 117-123.
Arvand et al. Clostridium difficile ribotypes 001, 017, and 027 are associated with lethal C. difficile infection in Hesse, Germany. Eurosurveillance, vol. 14(45), published Nov. 12, 2009, pp. 1-4.
Huang et al. Distinct ribotypes and rates of antimicrobial drug resistance in Clostridium difficile from Shanghai and Stockholm. Clinical Microbiology and Infection, vol. 15, published online Jul. 15, 2009, pp. 1170-1173.
Calderaro et al. Comparative analysis of different methods to detect Clostridium difficile infection. New Microbiologica, vol. 36, published Jan. 2013, pp. 57-63.
Eigner et al. Detection of C. difficile toxin as a model assay for performing fully automated high-throughput RT-PCR on clinical stool samples. Journal of Microbiological Methods, vol. 172(105882), published online Feb. 28, 2020, 8 pages.

(56) References Cited

OTHER PUBLICATIONS

Bélanger et al. Rapid Detection of Clostridium difficile in Feces by Real-Time PCR. Journal of Clinical Microbiology, vol. 41(2), published Feb. 2003, pp. 730-734.

Ganji et al. Comparison of the Detection Limits of the Culture and PCR Methods for the Detection of Clostridium difficile, Clostridium perfringens, Campylobacter jejuni, and Yersinia enterocolitica in Human Stool. Archives of Pediatric Infectious Diseases, vol. 5(1):e38888, published online Sep. 4, 2016, 7 pages.

Hink et al. A Systematic Evaluation of Methods to Optimize Culture-Based Recovery of Clostridium difficile From Stool Specimens. Author Manuscript. Anaerobe, vol. 19, published Feb. 2013, 14 pages.

Pandey et al. DNAzyme-Immobilizing Microgel Magnetic Beads Enable Rapid, Specific, Culture-Free, and Wash-Free Electrochemical Quantification of Bacteria in Untreated Urine. ACS Sensors, vol. 7, published Apr. 6, 2022, pp. 985-994.

Liu et al. Programming a topologically constrained DNA nanostructure into a sensor. Nature Communications, vol. 7:12074, published Jun. 23, 2016, pp. 1-7.

Pandey et al. Integrating programmable DNAzymes with electrical readout for rapid and culture-free bacterial detection using a handheld platform. Nature Chemistry, vol. 13, published Sep. 2021, pp. 895-901.

Chi et al. Single bacteria detection by droplet DNAzymecoupled rolling circle amplification. Analytical Methods, vol. 14, first published May 12, 2022, pp. 2244-2248.

McManus and Li. A Deoxyribozyme with a Novel Guanine Quartet-Helix Pseudoknot Structure. Journal of Molecular Biology, vol. 375, published online Nov. 6, 2007, pp. 960-968.

Chiuman and Li. Revitalization of Six Abandoned Catalytic DNA Species Reveals a Common Three-way Junction Framework and Diverse Catalytic Cores. Journal of Molecular Biology, vol. 357, published online Jan. 30, 2006, pp. 748-754.

Chiuman and Li. Simple Fluorescent Sensors Engineered with Catalytic DNA 'MgZ' Based on a Non-Classic Allosteric Design. PLOS ONE, vol. 2(e1224), published Nov. 21, 2007, pp. 1-11.

Kandadai and Li. Characterization of a catalytically efficient acidic RNA-cleaving deoxyribozyme. Nucleic Acids Research, vol. 33(22), published online Jan. 3, 2006, pp. 7164-7175.

Chen et al. Evolution of Sequence-Defined Highly Functionalized Nucleic Acid Polymers. Author manuscript. Nature Chemistry, vol. 10(4), published Apr. 2018, 18 pages.

Achenbach et al. Secondary-Structure Characterization of Two Proficient Kinase Deoxyribozymes. Biochemistry, vol. 44(10), published online Feb. 18, 2005, pp. 3765-3774.

Louie et al. Differences of the Fecal Microflora With Clostridium difficile Therapies. Clinical Infectious Diseases, vol. 60(S2), published May 2015, pp. S91-S97.

* cited by examiner

DNAzyme FOR *Clostridium difficile* DETECTION

CROSS-REFERENCE TO RELATED APPLICATION

This application claims the benefit of U.S. Provisional Patent Application No. 63/460,799 filed Apr. 20, 2023, herein incorporated by reference in its entirety.

INCORPORATION OF SEQUENCE LISTING

A computer readable form of the Sequence Listing "3244-P71841US01_SequenceListing" (90,757 bytes), submitted via Patent Center and created on Apr. 22, 2024, is herein incorporated by reference.

FIELD

The present disclosure relates to the field of functional nucleic acids, and in particular, to DNAzymes for detecting *Clostridium difficile* and methods of use thereof.

BACKGROUND

*Clostridium difficile* (*C. difficile*) is the bacterial pathogen responsible for an infectious disease known as *C. difficile* infection (CDI), a widespread healthcare-associated infection. Major symptoms of CDI include diarrhea, inflammation, abdominal pain, colitis and tissue necrosis with a mortality rate ranging from 2%-42%.[1-3] CDI represents a major health threat around the world, including North America, Europe, Asia, Western Pacific, Latin America, and Africa.[4-6] In the United States, this pathogen causes almost half a million infections every year, resulting in about ten thousand deaths.[7] In Canada, the number of CDI cases has been increasing dramatically since 2000 and CDI has become a frequent cause for hospital-associated diarrhea.[8] In Europe, healthcare-associated CDI cases are estimated to be around 125,500 annually with a financial burden estimated to be around €300 million.[9,10]

Early detection of pathogenic bacteria is very important for outbreak control and disease management. For diagnosing CDI, toxigenic culture and cell cytotoxicity assay are gold standard methods. However, these tests are labour-intensive and time-consuming, as they have to be conducted in diagnostic labs by skilled professionals and the time to produce reliable results can take up to 5 days.[11] To overcome some of these limitations, polymerase chain reaction (PCR) methods have also been adopted to achieve rapid diagnosis of CDI by identifying the presence of toxin-coding genes, tcdA and tcdB. Despite their high sensitivity,[12] PCR methods fail to distinguish active toxin production from asymptomatic carriers.[13] Alternatively, enzyme immunoassays (EIA) against toxin A or toxin B have been developed as rapid tests. However, the low sensitivity of these more rapid tests limits their clinical utility.[14,15] Another alternative and relatively rapid test involves the use of EIA to detect glutamate dehydrogenase (GDH) of *C. difficile*.[16] This test is rapid and highly sensitive, but cannot distinguish toxigenic strains of *C. difficile* from non-toxigenic strains.[15] Therefore, a positive GDH result requires a follow-up toxin assay to confirm the toxin expression.

There is interest in developing alternative assays for CDI based on functional nucleic acids, including DNA aptamers and DNAzymes.[17-21] DNA aptamers are artificial single-stranded DNA sequences that can be isolated from a synthetic random-sequence DNA pool to bind a specific target of interest through the use of a technique called in vitro selection.[22,23] DNAzymes are also artificial single-stranded DNA molecules isolated from a DNA pool but they are engineered to possess catalytic functions.[24-27] They can also be combined with aptamers for the creation of aptazymes that can be activated by a specific target. Many aptamers and DNAzymes have been reported for diverse target molecules and have been used as molecular recognition elements for the design of biosensors and bioassays.[28-31]

RNA-cleaving DNAzymes have been developed as biosensors for bacterial detection.[32,33] These DNAzymes are selected from a random-sequence DNA pool to cleave an RNA site embedded in a DNA substrate in the presence of a complex molecular mixture from a specific bacterial species.[34] The RNA site is flanked by a pair of nucleotides modified with a fluorophore and a matching quencher, and therefore the derived RNA-cleaving DNAzymes are inherently fluorogenic, capable of emitting high levels of fluorescence upon RNA cleavage.[35'36] To date, RNA-cleaving fluorogenic DNAzymes (RFDs) have been developed for a few different bacterial pathogens, including *Escherichia coli*,[37] *Helicobacter pylori*,[38] *Legionella pneumophila*,[39] *Staphylococcus aureus*,[40] *Klebsiella pneumoniae*,[41], and *C. difficile*.[21] U.S. Pat. No. 9,624,551 discloses an RNA-cleaving DNAzyme-based probe for detecting an unidentified protein target from a microorganism.

In the case of *C. difficile*, a previously described RFD, termed RFD-CD1 hereinafter, was selected to recognize a strain of *C. difficile* named BI/027-H (Hamilton), a locally isolated hypervirulent strain.[21] This DNAzyme possessed remarkable specificity as it can only be activated by the specific BI/027-H strain and shows no cleavage activity in the presence of eleven other *C. difficile* strains. This profound selectivity is attributed to the recognition of a uniquely mutated version of a protein named TcdC by RFD-CD1.[21] Unfortunately, this high specificity presents a problem for CDI diagnosis: RFD-CD1 cannot be used as a universal DNAzyme probe to diagnose CDI caused by other strains of *C. difficile*.

The background herein is included solely to explain the context of the disclosure. This is not to be taken as an admission that any of the material referred to was published, known, or part of the common general knowledge as of the priority date.

SUMMARY

In accordance with an aspect of the present disclosure, provided herein is a catalytic nucleic acid comprising a nucleotide sequence selected from the group consisting of SEQ ID NOs: 10-16, 19-21, 23, 29-32, 36, 37, 39-44, and 47, a functional fragment thereof, or a functional variant thereof, for detecting *Clostridium difficile* (*C. difficile*).

In some embodiments, the catalytic nucleic acid comprises the nucleotide sequence selected from the group consisting of SEQ ID NOs: 10-15, 19, 30, 36, 37, 39-43, and 47.

In some embodiments, the catalytic nucleic acid comprises the nucleotide sequence selected from the group consisting of SEQ ID NOs: 11, 36, 40-42, and 47.

In some embodiments, the catalytic nucleic acid has a limit-of-detection of about 100 CFU/mL *C. difficile*.

In some embodiments, the catalytic nucleic acid is for cleavage of a nucleic acid substrate.

In accordance with another aspect of the present disclosure, provided herein is a catalytic nucleic acid probe comprising the catalytic nucleic acid disclosed herein and a detectable substrate.

In some embodiments, the detectable substrate comprises a ribonucleotide flanked by a fluorophore modified nucleic acid residue and a quencher modified nucleic acid residue.

In some embodiments, the catalytic nucleic acid probe is configured to generate a fluorogenic signal upon contacting *C. difficile*.

In some embodiments, the detectable substrate comprises the nucleotide sequence of SEQ ID NO: 1 or 76.

In some embodiments, the catalytic nucleic acid probe comprises the nucleotide sequence selected from the group consisting of SEQ ID NOs: 48-53 and 70-75.

In accordance with another aspect of the present disclosure, provided herein is a biosensor for detecting *C. difficile* comprising the catalytic nucleic acid disclosed herein, or the catalytic nucleic acid probe disclosed herein, functionalized on and/or in a material.

In accordance with another aspect of the present disclosure, provided herein is a method for detecting the presence of *C. difficile* in a sample, the method comprising:

a) combining the sample with the catalytic nucleic acid probe of claim 6 in a liquid to form a mixture;
b) incubating the mixture to allow for a cleavage reaction in which the catalytic nucleic acid cleaves the detectable substrate, thereby releasing a fragment comprising a quencher modified nucleic acid residue to produce a fluorogenic signal;
c) optionally quenching the cleavage reaction;
d) detecting the fluorogenic signal and/or a cleaved fragment;

wherein detecting the fluorogenic signal and/or the cleaved fragment indicates presence of *C. difficile* in the sample.

In some embodiments, b) comprises incubating the mixture at about 37° C.

In some embodiments, the liquid is a buffer.

In some embodiments, the buffer comprises about 50 mM $Mg^{2+}$.

In some embodiments, the buffer is about pH 8.0.

In some embodiments, quenching of the cleavage reaction comprises adding a quenching buffer to the mixture.

In some embodiments, the quenching buffer comprises EDTA and/or urea.

In some embodiments, detecting the fluorogenic signal comprises analysis via denaturing polyacrylamide gel electrophoresis.

In some embodiments, the method detects *C. difficile* infection in a subject.

In some embodiments, the sample is a stool sample.

In accordance with another aspect of the present disclosure, provided herein is a kit for detecting *C. difficile* in a sample, wherein the kit comprises the catalytic nucleic acid disclosed herein, the catalytic nucleic acid probe disclosed herein, the biosensor disclosed herein, or components required for the method disclosed herein, and instructions for use of the kit.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should be given the broadest interpretation consistent with the description as a whole.

DRAWINGS

Certain embodiments of the disclosure will now be described in greater detail with reference to the attached drawings in which:

FIG. 1A shows in vitro selection of *C. difficile*-responsive RNA-cleaving DNAzymes in exemplary embodiments of the disclosure. FIG. 1A shows counter-selection and positive-selection steps implemented to drive the selection of *C. difficile*-responsive RNA-cleaving DNAzymes from a random-sequence DNA pool-R: adenosine ribonucleotide; F: fluorophore (FAM) modification; Q: quencher (Dabcyl) modification—the constant region is shown in black and the random domain in grey.

FIG. 1B shows in vitro selection of *C. difficile*-responsive RNA-cleaving DNAzymes in exemplary embodiments of the disclosure. FIG. 1B shows the full-length sequence of QRF30-RFD-CD2 (SEQ ID NO: 48) from 5' end to 3' end-RFD-CD2 (SEQ ID NO: 11), comprising a 20-nt forward primer binding site (SEQ ID NO: 3), a 50-nt random domain, and a 20-nt reverse primer binding site (SEQ ID NO: 9), was ligated with a 30-nt substrate (QRF30, SEQ ID NO: 1).

FIG. 1C shows in vitro selection of *C. difficile*-responsive RNA-cleaving DNAzymes in exemplary embodiments of the disclosure. FIG. 1C shows 10% dPAGE analysis to assess the cleavage performance of RFD-CD2 (SEQ ID NO: 48; SEQ ID NO: 11 further comprising SEQ ID NO: 1) in selection buffer (SB) and SB containing CEM-NAP1-MK: marker of RFD-CD2, produced by incubating RFD-CD2 with 0.2 M NaOH at 90° C. for 1.5 minutes (a condition that leads to the cleavage of the RNA unit).

FIG. 1D shows in vitro selection of *C. difficile*-responsive RNA-cleaving DNAzymes in exemplary embodiments of the disclosure. FIG. 1D shows 10% dPAGE analysis to assess the cleavage response of RFD-CD2 towards CEM prepared from *C. difficile* NAP1 (N1), NAP2 (N2) and NAP7 (N7) strains—cleavage percentage is calculated as: % $Clv=(FI_{Clv}/6)/[(FI_{Clv}/6)+FI_{Unclv}]$; $FI_{Clv}$: fluorescence intensity of cleaved band; $FI_{Unclv}$: fluorescence intensity of uncleaved band.

FIG. 2 shows in vitro selection strategy for isolating *C. difficile*-responsive RFD from a DNA pool in exemplary embodiments of the disclosure: the selection starts with a ligation reaction where the random sequence pool is ligated with a chimeric RNA/DNA substrate sequence (step 1); the ligated molecules are purified by dPGA and then incubated with control bacteria in a counter-selection step (step 2) to remove crossing-reacting DNA species; the nonreactive DNA molecules are purified by dPAGE (step 3) and are incubated with *C. difficile* in the positive selection step (step 4) to induce the cleavage of *C. difficile*-reactive DNAzyme molecules (step 5). The cleavage products are isolated by dPAGE (step 6) and amplified with PCR (polymerase chain reaction); the PCR uses a normal forward primer and a reverse primer containing 20 adenine nucleotides at 5'-end separated by a nonamplifiable linker such that the amplicons from the PCR step contain a DNAzyme-coding forward strand and a non-DNAzyme-coding reverse strand that is 20 nucleotides longer; the DNAzyme-coding strand is then purified by dPAGE and used as the DNA pool to initiate the next round of selection –; R: adenosine ribonucleotide; F: fluorophore (FAM); Q: quencher (Dabcyl); P: phosphate; the constant region is black and the random domain is grey.

FIG. 3 shows in vitro selection progress in exemplary embodiments of the disclosure: cleavage percentage in counter selection (left column) and positive selection (right column) from round 1 to round 7.

FIG. 4 shows assessment of cleavage activity of the top three candidate DNAzymes (SEQ ID NOs: 10-12 further comprising further comprising SEQ ID NO: 1) from round-7 pool in exemplary embodiments of the disclosure: the cleavage activity of each candidate was accessed with selection buffer (SB) only and in SB containing CEM-NAP1-MK: marker of each candidate sequence, prepared by treating each candidate with 0.2 M NaOH at 90° C. for 1.5 minutes.

FIG. 5A shows improved magnesium concentration for RFD-CD2 (SEQ ID NO: 48).

FIG. 5B shows improved reaction temperature for RFD-CD2.

FIG. 5C shows improved reaction pH for RFD-CD2.

FIG. 5D shows kinetic profiles of RFD-CD2 under original (SB) and improved (RB2) conditions.

Figure 5A:
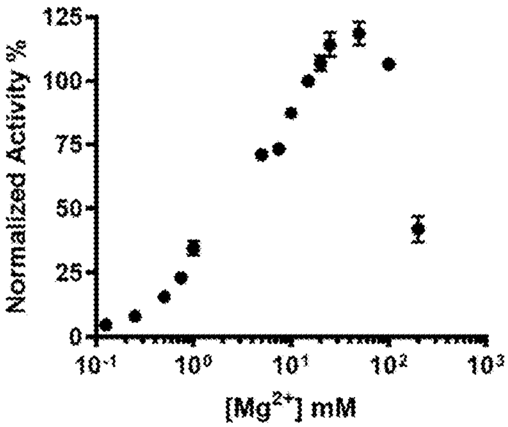
FIG. 5A shows improved reaction condition improvement in exemplary embodiments of the disclosure.
Figure 5B:
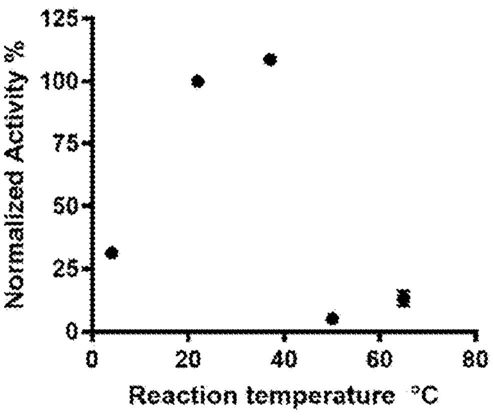
FIG. 5B shows reaction condition improvement in exemplary embodiments of the disclosure.
Figure 5C:
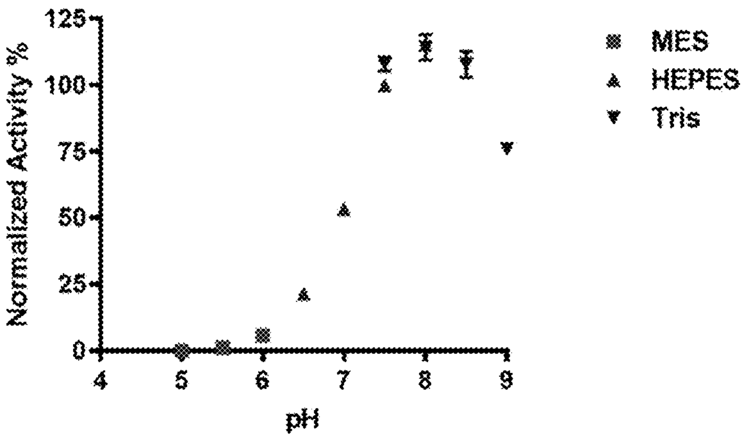
FIG. 5C shows reaction condition improvement in exemplary embodiments of the disclosure.
Figure 5D:
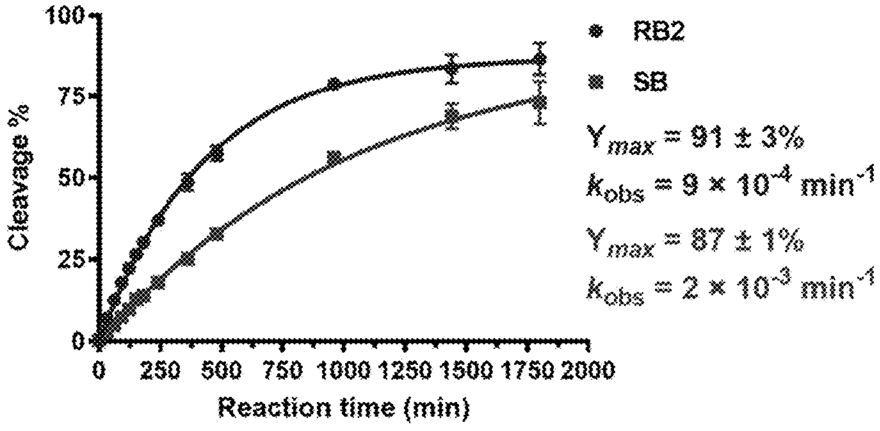
FIG. 5D shows reaction condition improvement in exemplary embodiments of the disclosure.
Figure 5E:
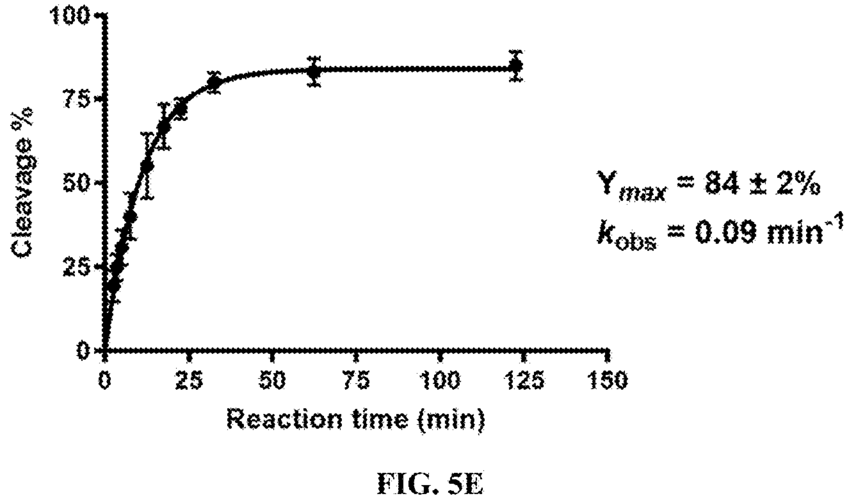

FIG. 5E shows reaction condition improvement in exemplary embodiments of the disclosure. FIG. 5E shows kinetic profile of RFD-CD2 with concentrated CEM-NAP1—cleavage percentage was fit by one-phase association equation $Y=Y_{max}[1-e^{-kt}]$ with Graphpad Prism 4.03; Y: cleavage percentage; $Y_{max}$: maximum cleavage yields; k: observed rate constant $k_{obs}$—each data point in each graph is the mean number of three trials and error bar represent the standard deviation.

Figure 6:
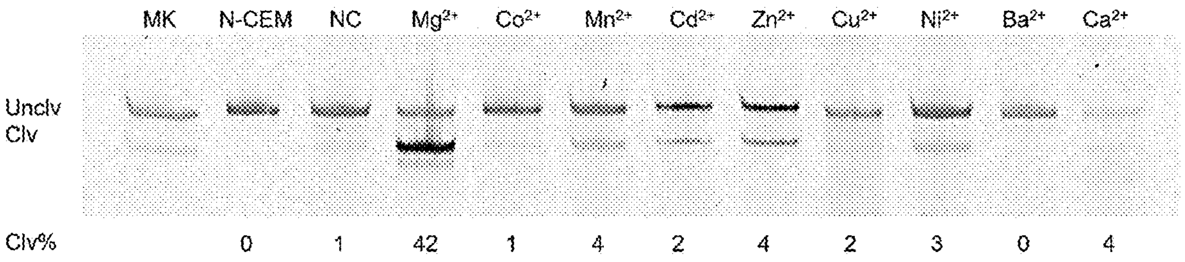

FIG. 6 shows assessment of divalent metal ion dependence of RFD-CD2 (SEQ ID NO: 48) in exemplary embodiments of the disclosure—MK: marker; N-CEM: reaction without CEM-NAP1; NC: reaction without any divalent metal ion—RFD-CD2 was incubated with 15 mM $MCl_2$ for 24 hours.

Figure 7A:
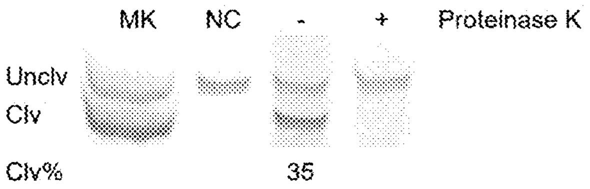

FIG. 7A shows characterization of the target molecule of RFD-CD2 (SEQ ID NO: 48) in exemplary embodiments of the disclosure. FIG. 7A shows response of RFD-CD2 to proteinase K-treated CEM-NAP1.

Figure 7B:
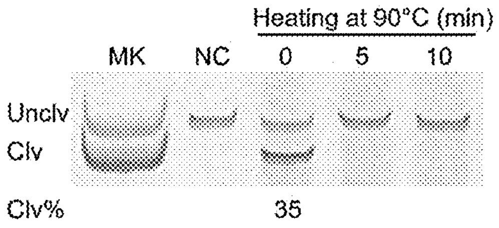

FIG. 7B shows characterization of the target molecule of RFD-CD2 (SEQ ID NO: 48) in exemplary embodiments of the disclosure. FIG. 7B shows response of RFD-CD2 to heat-treated CEM-NAP1.

Figure 7C:
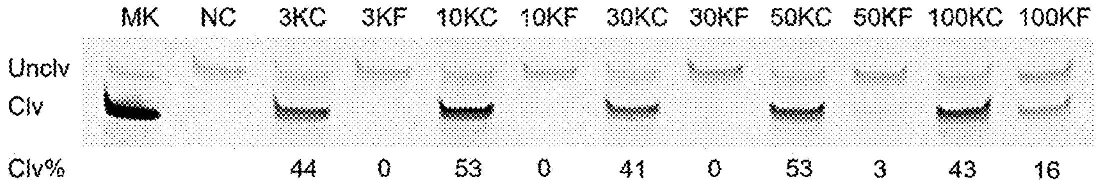

FIG. 7C shows characterization of the target molecule of RFD-CD2 (SEQ ID NO: 48) in exemplary embodiments of the disclosure. FIG. 7C shows assessment of the size of the target protein of RFD-CD2-CEM-NAP1 was passed through spin columns with membrane sizes ranging from 3 to 100 kDa; molecules retained above the membrane were collected as the concentrate fraction (KC) and the passing-through molecules were collected as the filtrate fraction (KF)-MK: marker of RFD-CD2, produced with 0.2 M NaOH at 90° C. for 1.5 minutes; NC: negative control, RFD-CD2 incubated with RB2 only; reactions were incubated at 37° C. for 4 hours.

Figure 8A:
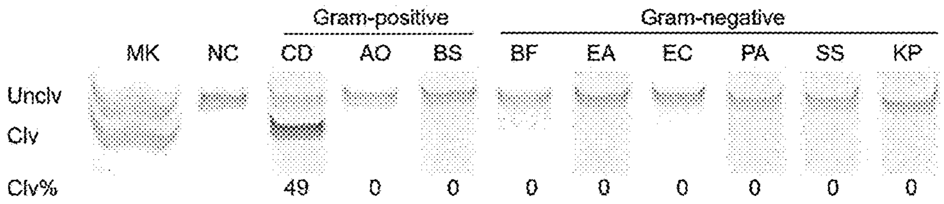

FIG. 8A shows specificity and selectivity of RFD-CD2 (SEQ ID NO: 48) in exemplary embodiments of the disclosure. FIG. 8A shows species specificity of RFD-CD2-CD: *Clostridium difficile*; AO: *Actinomyces orientalis*; BS: *Bacillus subtilis*; BF: *Bacteroid fragilis*; EA: *Enterobacter aerogenes*; EC: *Escherichia coli*; PA: *Pseudomonas aeruginosa*; SS: *Shigella sonnei*; and KP: *Klebsiella pneumoniae.*

Figure 8B:
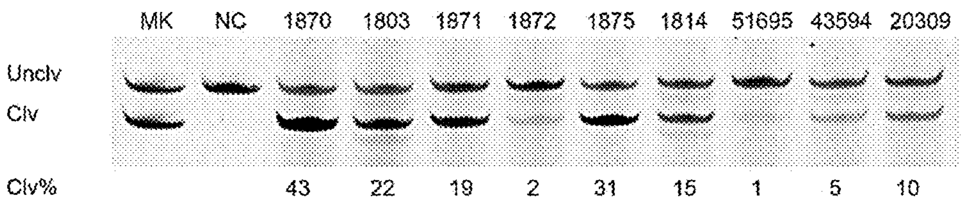

FIG. 8B shows specificity and selectivity of RFD-CD2 (SEQ ID NO: 48) in exemplary embodiments of the disclosure. FIG. 8B shows strain selectivity of RFD-CD2-MK: marker of RFD-CD2, produced by treating RFD-CD2 with 0.2 M NaOH at 90° C. for 1.5 minutes; NC: negative control, RFD-CD2 incubated with RB2 only; cleavage reactions between RFD-CD2 and relevant CEM were performed at 37° C. for 4 hours.

Figure 9A:
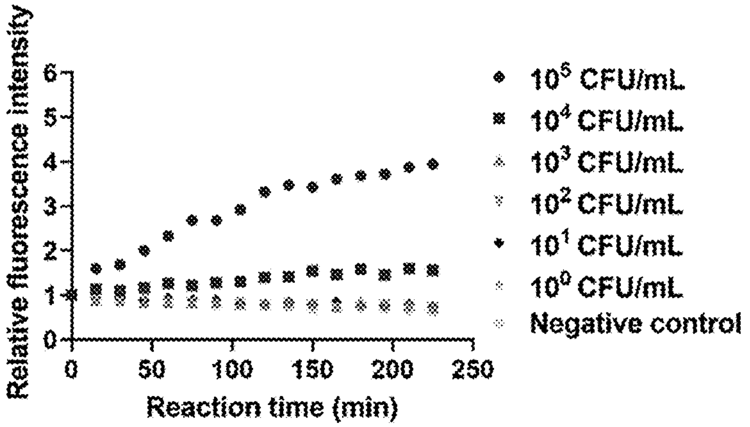

FIG. 9A shows RFD-CD2 (SEQ ID NO: 48) as a fluorescent sensor for *C. difficile* in exemplary embodiments of the disclosure. FIG. 9A shows fluorescence response of RFD-CD2 with whole cell culture of NAP1 prepared at various concentrations—the relative fluorescence intensity was calculated as $(F-F_b)/(F_0-F_b)$; $F_b$: fluorescence intensity of whole cell culture (without the DNAzyme); F: fluorescence intensity of the DNAzyme reaction at a given reaction time; $F_0$: fluorescence intensity at time 0.

Figure 9B:
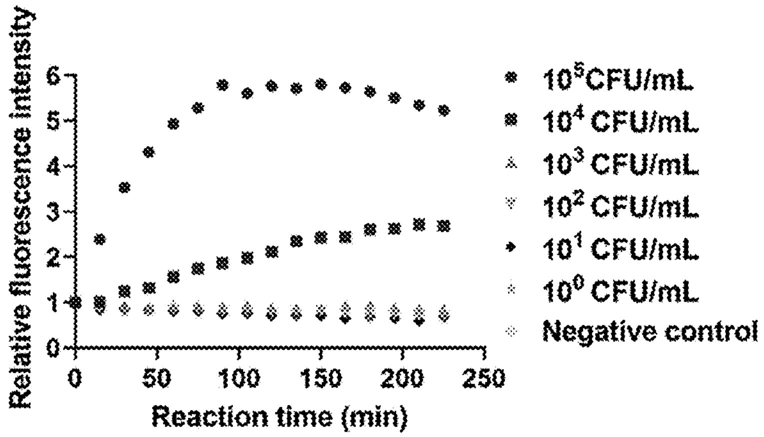

FIG. 9B shows RFD-CD2 (SEQ ID NO: 48) as a fluorescent sensor for *C. difficile* in exemplary embodiments of the disclosure. FIG. 9B shows fluorescence response of RFD-CD2 with CEM-NAP1 prepared at various concentrations from its corresponding whole cell culture—the relative fluorescence intensity was calculated as $(F-F_b)/(F_0-F_b)$; $F_b$: fluorescence intensity of CEM-NAP1 (without the DNAzyme); F: fluorescence intensity of the DNAzyme reaction at a given reaction time; $F_0$: fluorescence intensity at time 0.

Figure 9C:
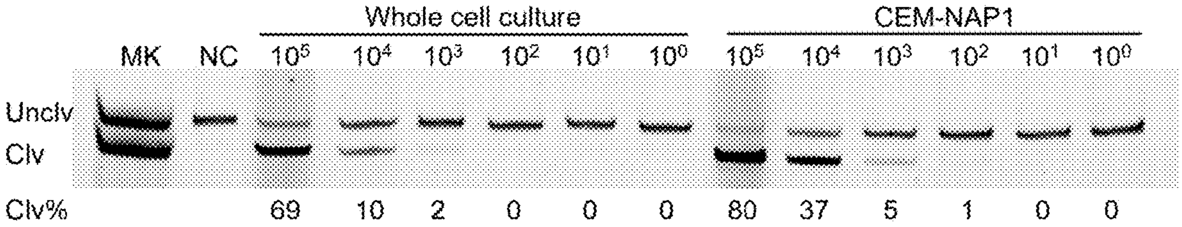

FIG. 9C shows RFD-CD2 (SEQ ID NO: 48) as a fluorescent sensor for *C. difficile* in exemplary embodiments of the disclosure. FIG. 9C shows testing signal responses with 10% dPAGE-MK: marker of RFD-CD2, produced by treating RFD-CD2 with 0.2 M NaOH at 90° C. for 1.5 minutes; NC: negative control where RFD-CD2 was incubated with RB2 only; all cleavage reactions were performed at 37° C. for 4 hours.

Figure 10A:
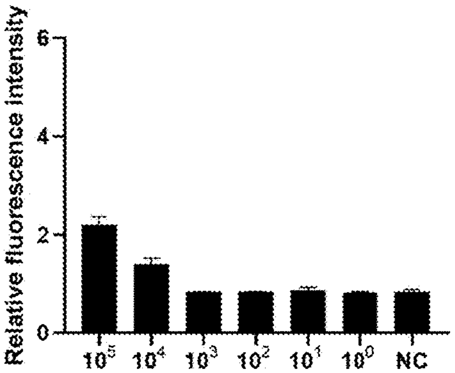

FIG. 10A shows the limit of detection of RFD-CD2 (SEQ ID NO: 48) with a fluorescence reader after 1-hour incubation in exemplary embodiments of the disclosure. FIG. 10A shows fluorescence towards whole cell culture of NAP1 in CFU/mL.

Figure 10B:
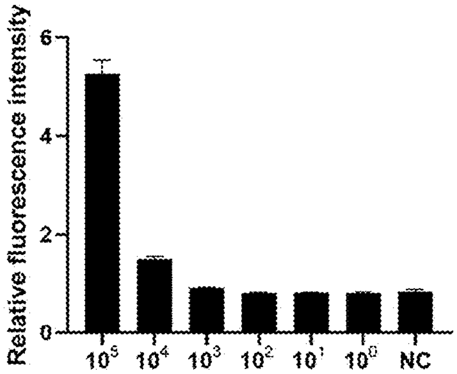

FIG. 10B shows the limit of detection of RFD-CD2 (SEQ ID NO: 48) with a fluorescence reader after 1-hour incubation in exemplary embodiments of the disclosure. FIG. 10B shows fluorescence towards CEM-NAP1 in CFU/mL—the columns represent the mean and the error bars represent the standard deviation of triplicate experiments; NC: negative control where RFD-CD2 was incubated with RB2 only.

Figure 11A:
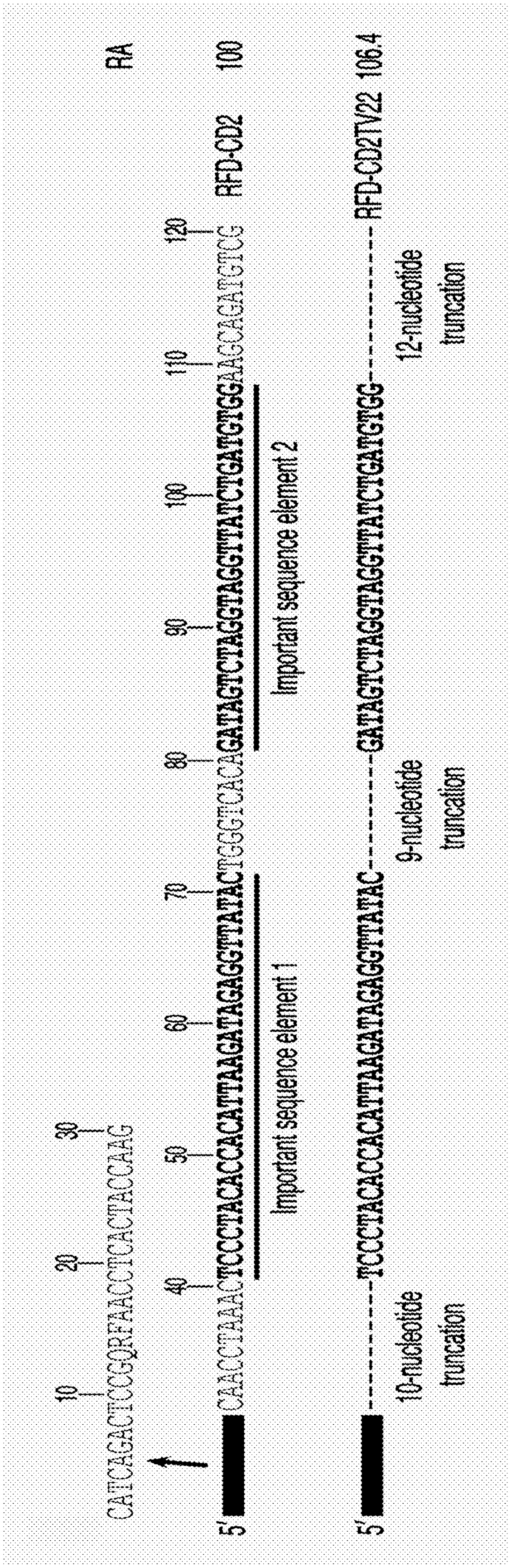

FIG. 11A shows sequence characterization of RFD-CD2 (SEQ ID NO: 48) in exemplary embodiments of the disclosure. FIG. 11A shows identification of functionally important sequence elements via sequence truncation of RFD-CD2: the first 30 nucleotides—substrate domain; $C_{31}$-$C_{50}$—forward primer binding site; $A_{51}$-$A_{110}$—the original random-sequence domain; $G_{111}$-$G_{120}$—reverse primer binding site; $T_{41}$-$C_{71}$ (shown in bold font)—important sequence element 1; $G_{81}$-$G_{108}$ (also shown in bold font)—important sequence element 2; sequence elements $C_{31}$-$C_{40}$, $T_{72}$-$C_{79}$, and $A_{108}$-$G_{120}$ (all shown in regular font)—dispensable sequence elements; RA: relative activity with RFD-CD2 taken as 100.

Figure 11B:
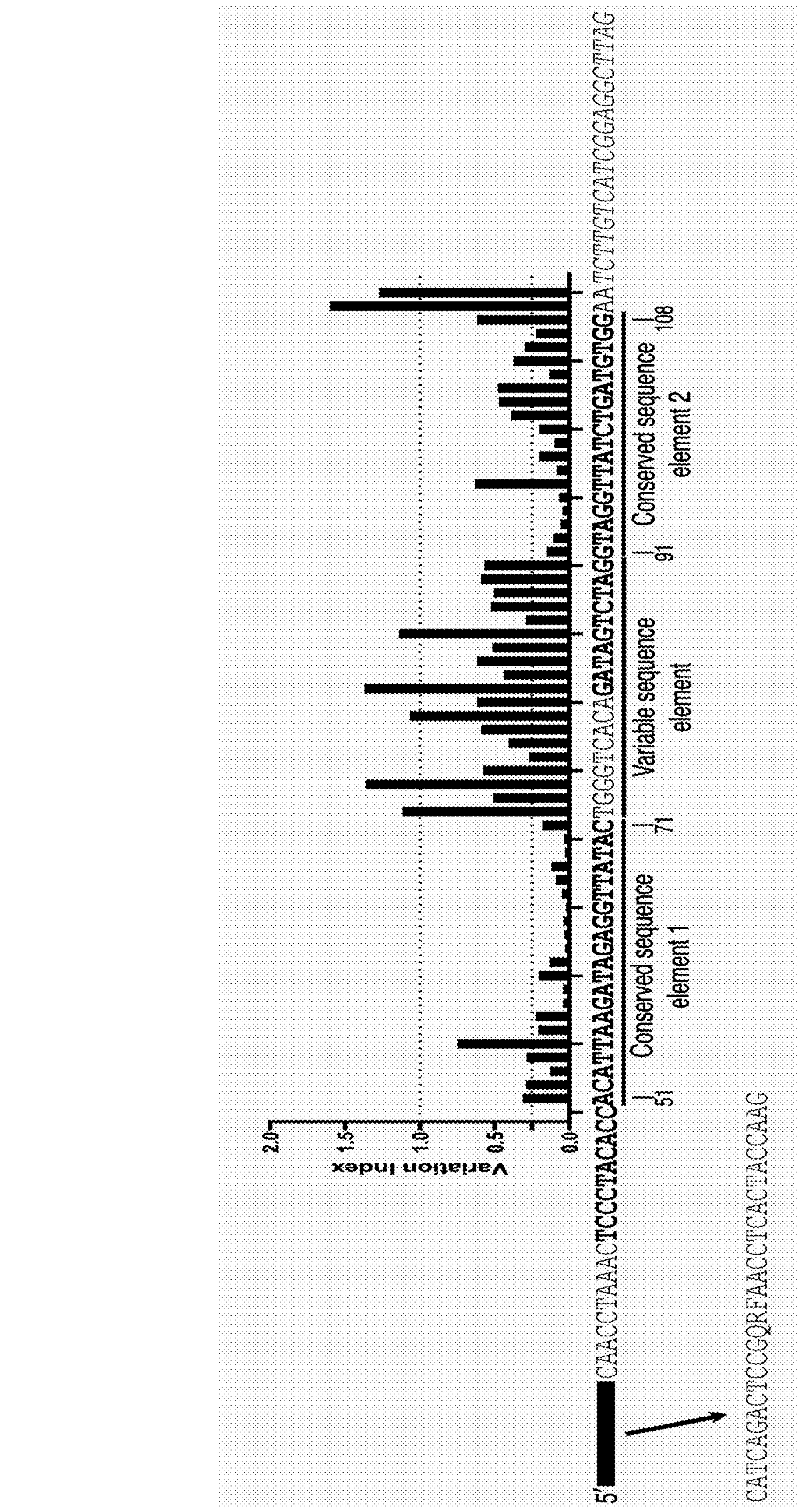

FIG. 11B shows sequence characterization of RFD-CD2 (SEQ TD NO: 48) in exemplary embodiments of the disclosure. FIG. 11B shows sequence analysis of the reselection pool—the variation index (VI) was calculated by dividing the sum mutation rate of top 450 centroids at each position by 0.24 (the mutation rate of the starting library); VI=1.0 and VI=0.25 were horizontally dot-lined—the full-length DNAzyme sequence in the reselection displayed below the VI bar chart; nucleotides $C_1$-$A_{110}$—same sequence from RFD-CD2; nucleotides $T_{111}$-$G_{130}$—the reverse primer binding site in the reselection (shown in italic font).

Figure 12:
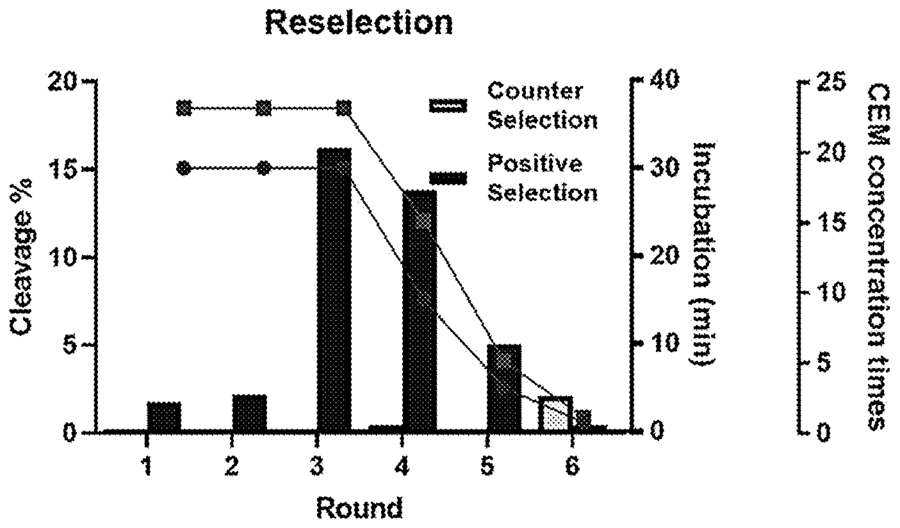

FIG. 12 shows in vitro reselection progress towards CEM-NAP1 in exemplary embodiments of the disclosure: the columns represent the cleavage percentage in counter selection (light grey) and positive selection (dark grey) over six rounds in reselection and selection pressure incubation time (line with circles) and CEM concentration (line with squares) in positive selection are shown from round 1 to round 6.

Figure 13A:
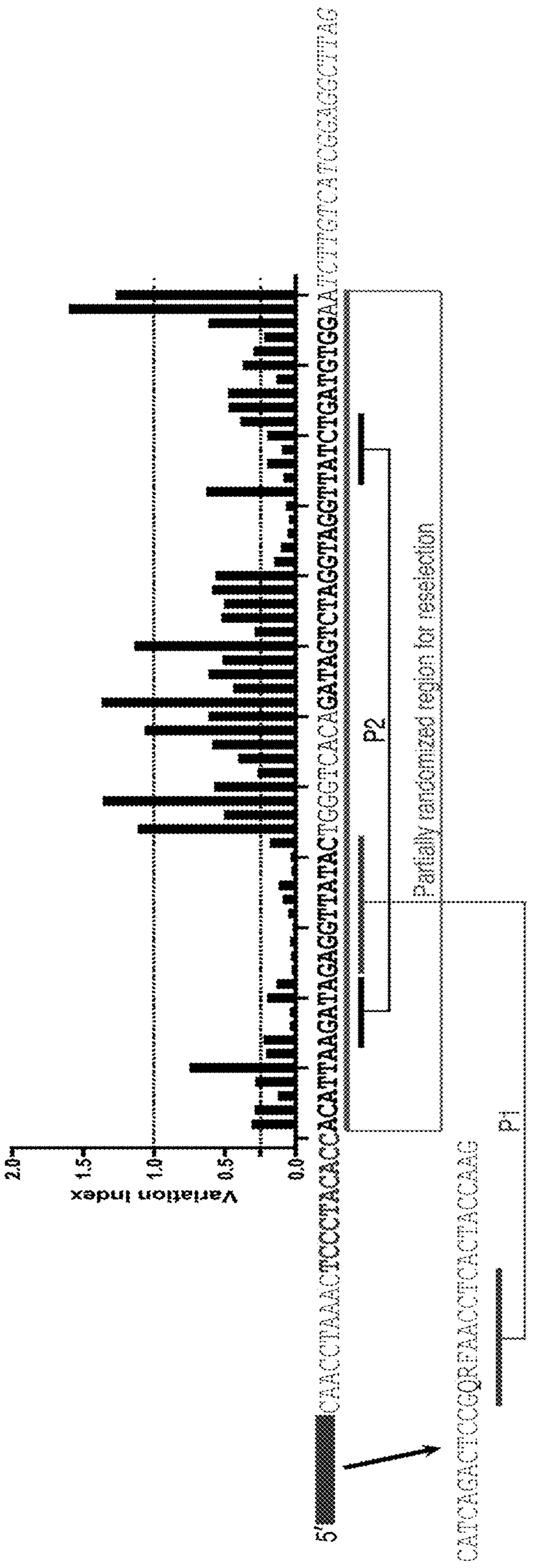

FIG. 13A shows elucidation of the secondary structure of RFD-CD2 (SEQ ID NO: 48) in exemplary embodiments of the disclosure. FIG. 13A shows two proposed pairing elements, P1 and P2, in full-length RFD-CD2 sequence.

Figure 13B:
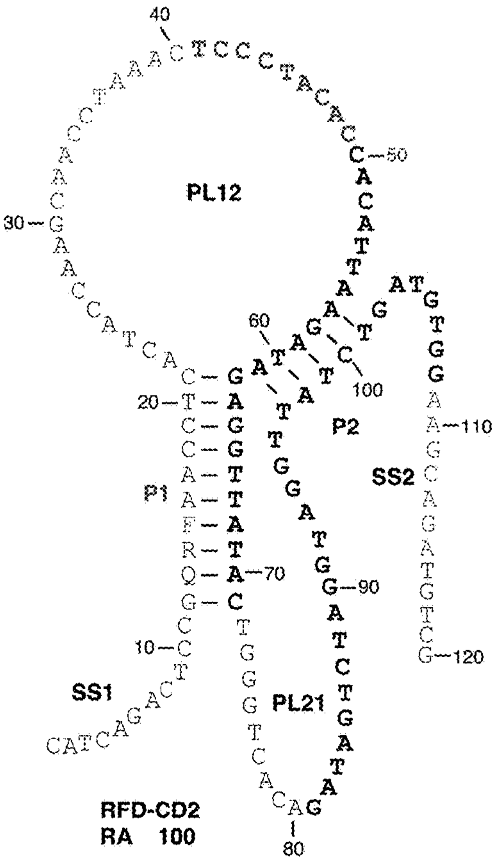

FIG. 13B shows elucidation of the secondary structure of RFD-CD2 (SEQ ID NO: 48) in exemplary embodiments of the disclosure. FIG. 13B shows proposed secondary structure of RFD-CD2.

Figure 13C:
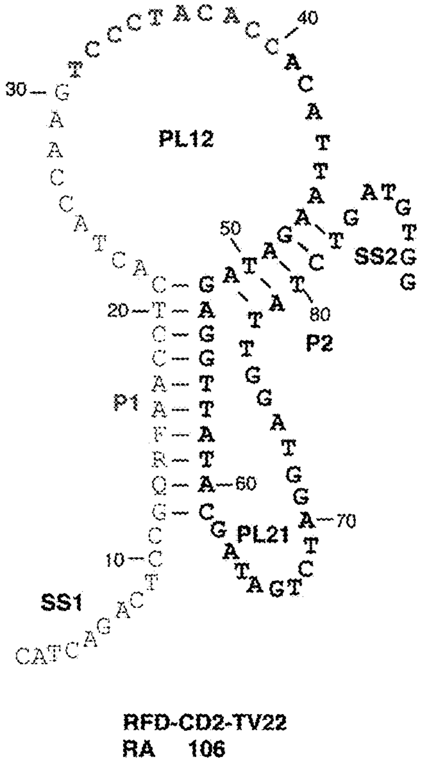

FIG. 13C shows elucidation of the secondary structure of RFD-CD2 (SEQ ID NO: 49) in exemplary embodiments of the disclosure. FIG. 13C shows proposed secondary structure of RFD-CD2-TV22.

Figure 13D:
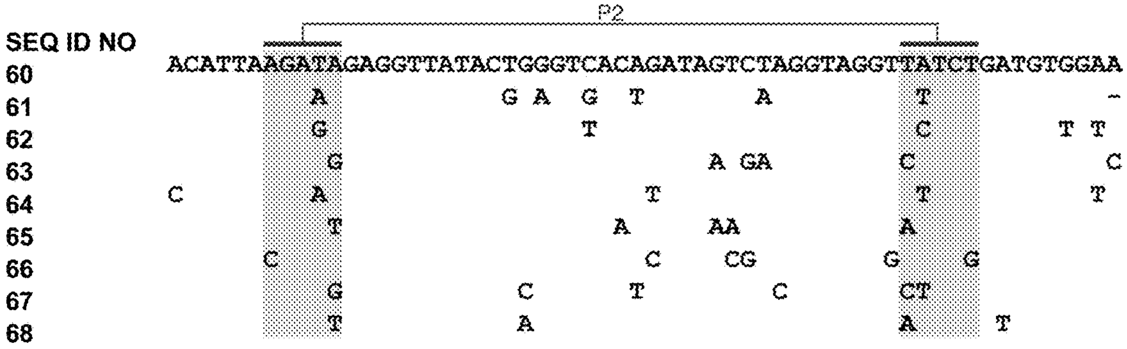

FIG. 13D shows elucidation of the secondary structure of RFD-CD2 (SEQ ID NO: 48) in exemplary embodiments of the disclosure. FIG. 13D shows examples of complementary base covariant mutations in P2 observed in the selected mutants of RFD-CD2—nucleotides involved in P2 were shown in grey background; unmutated nucleotides were left blank; a dash represents a deletion.

Figure 13E:
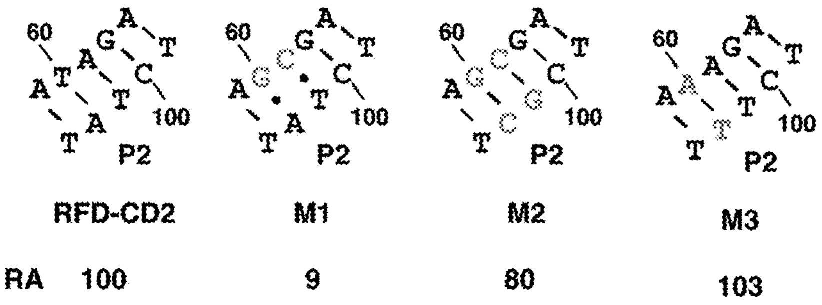

FIG. 13E shows elucidation of the secondary structure of RFD-CD2 (SEQ ID NO: 48) in exemplary embodiments of the disclosure. FIG. 13E shows mutants designed to test the functionality of P2—mutated nucleotides shown in light grey—RA: relative activity with RFD-CD2 taken as 10.

Figure 13F:
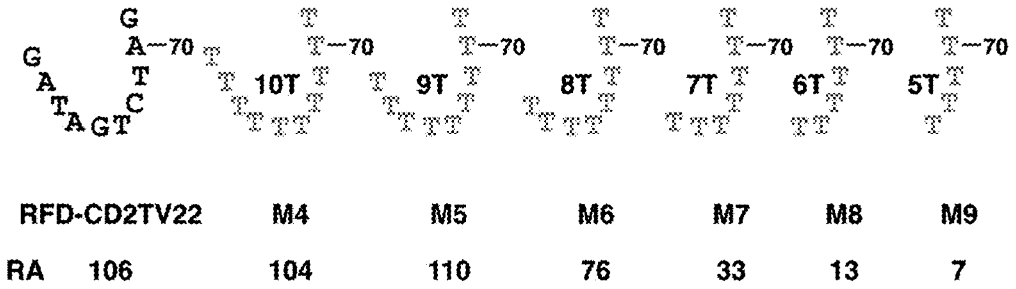

FIG. 13F shows elucidation of the secondary structure of RFD-CD2 (SEQ ID NO: 48) in exemplary embodiments of the disclosure. FIG. 13F shows examination of mutants with a poly-T linker of varying lengths in PL21 of RFD-CD2-TV22 (SEQ ID NO: 49) and their relative activity to RFD-CD2.

Figure 13G:
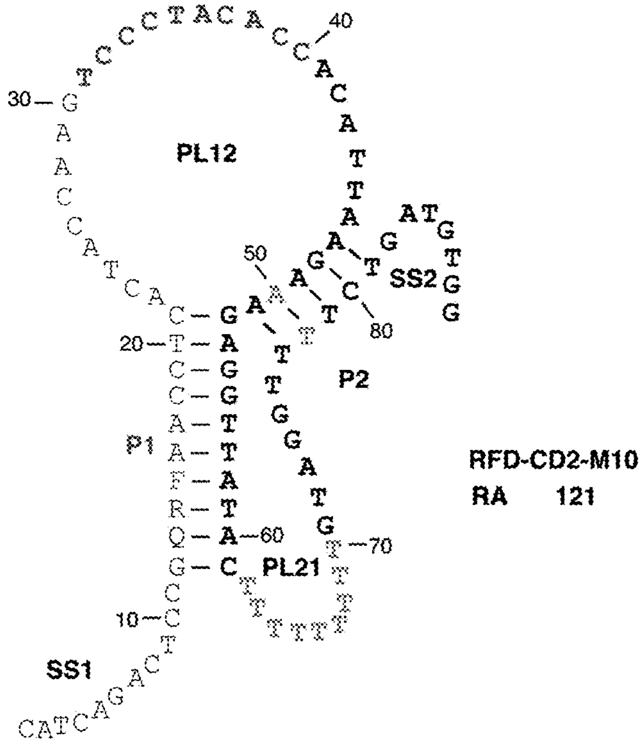

FIG. 13G shows elucidation of the secondary structure of RFD-CD2 (SEQ ID NO: 53) in exemplary embodiments of the disclosure. FIG. 13G shows proposed secondary structure of RFD-CD2-M10 with a 9T linker and an inverted A-T pair at position 50 and 78.

Figure 14A:
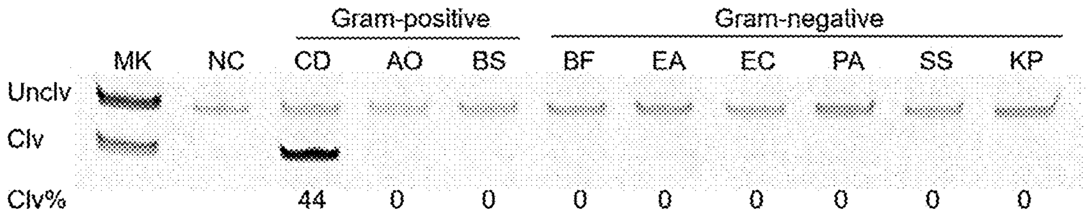

FIG. 14A shows specificity and selectivity of RFD-CD2-M10 (SEQ ID NO: 53) in exemplary embodiments of the disclosure. FIG. 14A shows species specificity of RFD-CD2-M10-CD: *Clostridium difficile*; AO: *Actinomyces orientalis*; BS: *Bacillus subtilis*; BF: *Bacteroid fragilis*; EA: *Enterobacter aerogenes*; EC: *Escherichia coli*; PA: *Pseudomonas aeruginosa*; SS: *Shigella sonnei*; and KP: *Klebsiella pneumoniae.*

Figure 14B:
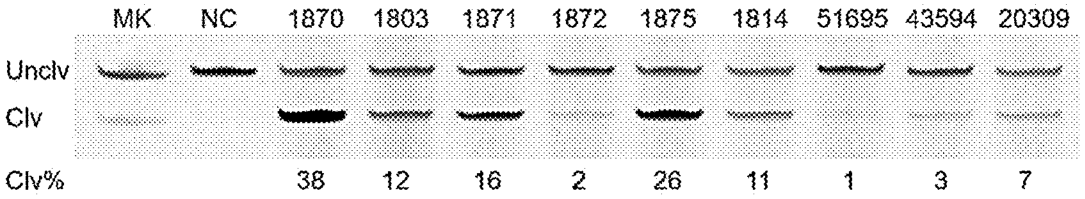

FIG. 14B shows specificity and selectivity of RFD-CD2-M10 (SEQ ID NO: 53) in exemplary embodiments of the disclosure. FIG. 14B shows strain selectivity of RFD-CD2-M10-MK: marker of RFD-CD2-M10, produced by treating RFD-CD2-M10 with 0.2 M NaOH at 90° C. for 1.5 minutes; NC: negative control, RFD-CD2-M10 incubated with RB2 only—cleavage reactions between RFD-CD2-M10 and relevant CEM were performed at 37° C. for 4 hours.

Further aspects and features of the example embodiments described herein will appear from the following description taken together with the accompanying drawings.

DETAILED DESCRIPTION

I. Definitions

Unless otherwise indicated, the definitions and embodiments described in this and other sections are intended to be applicable to all embodiments and aspects of the present disclosure herein described for which they are suitable as would be understood by a person skilled in the art. It is also to be understood that the terminology used herein is for the purpose of describing particular aspects only and is not intended to be limiting.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies. The modifier "about" used in connection with a quantity is inclusive of the stated value and has the meaning dictated by the context (e.g., it includes the degree of error associated with measurement of the particular quantity). In addition, all ranges disclosed herein are inclusive of the endpoints and also any intermediate range points, whether explicitly stated or not, and the endpoints are independently combinable with each other. Further, the recitation of ranges by endpoints herein includes all numbers and fractions subsumed within that range (e.g. 1 to 5 includes for example 1, 1.5, 2, 2.75, 3, 3.90, 4, and 5). It is also to be understood that all numbers and fractions thereof are presumed to be modified by the term "about".

As used in this disclosure, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The abbreviation, "e.g." is derived from the Latin exempli gratia and is used herein to indicate a non-limiting example. Thus, the abbreviation "e.g." is synonymous with the term "for example." The word "or" is intended to include "and" unless the context clearly indicates otherwise.

The term "sample" or "test sample" as used herein refers to any material in which the presence or amount of a target analyte is unknown and can be determined in an assay. The sample can be from any source, for example, any biological (e.g. human or animal samples, including clinical samples), environmental (e.g. water, soil or air) or natural (e.g. plants) source, or from any manufactured or synthetic source (e.g. food or drinks). The sample can be comprised or is suspected of comprising one or more analytes. The sample can be a "biological sample" comprising cellular and non-cellular material, including, but not limited to, tissue samples, saliva, sputum, urine, feces, blood, serum, other bodily fluids and/or secretions.

The term "target", "analyte" or "target analyte" as used herein refer to any agent, including, but not limited to, a small inorganic molecule, small organic molecule, metal ion, biomolecule, toxin, biopolymer (such as a nucleic acid, carbohydrate, lipid, peptide, protein), cell, tissue, microorganism and virus, for which one would like to sense or detect. The analyte can be either isolated from a natural source or synthetic. The analyte can be a single compound or a class of compounds, such as a class of compounds that share structural or functional features. The term analyte also includes combinations (e.g. mixtures) of compounds or agents such as, but not limited, to combinatorial libraries and samples from an organism or a natural environment. In some embodiments, the target is from *Clostridium difficile*. In some embodiments, the target is a protein target. In some embodiments, the protein target is a protein target of greater than about 30 kDa. In some embodiments, the protein target is a protein target of greater than about 100 kDa. In some embodiments, the protein target is a protein target of between about 30 kDa and about 100 kDa.

The term "subject" as used herein includes all members of the animal kingdom including mammals such as a mouse, a rat, a dog and a human.

The term "nucleic acid" as used herein refers to a biopolymer comprising monomers of nucleotides, such as deoxyribonucleic acid (DNA), ribonucleic acid (RNA) and other polynucleotides of modified nucleotides and/or nucleotide derivatives, and can be either double stranded (ds) or single stranded (ss). In some embodiments, modified nucleotides contain one or more modified bases (e.g. unusual bases such as inosine, and functional modifications to the bases such as amino), modified backbones (e.g. peptide nucleic acid, PNA) and/or other chemically, enzymatically, or metabolically modified forms. Examples of modified nucleotides which can be used to generate the nucleic acids disclosed herein include xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine. Alternatively, the nucleic acid molecules can be produced biologically using an expression vector. The term "functional fragment" as used herein refers to a fragment of the nucleic acid that retains the functional property of the full-length nucleic acid, for example, the ability of the fragment to act as a DNAzyme for detecting a particular analyte, for example, *Clostridium difficile*.

The term "catalytic nucleic acid", "catalytic DNA", "deoxyribozyme", "DNA enzyme", or "DNAzyme" as used herein can refer to a nucleic acid molecule or oligonucleotide sequence that can catalyze or initiate a reaction. DNAzymes may be single-stranded DNA and can include RNA, modified nucleotides and/or nucleotide derivatives. In some embodiments, the DNAzyme is "RNA-cleaving" and catalyzes the cleavage of a particular substrate, for example a nucleic acid sequence comprising one or more ribonucleotides, at a defined cleavage site. In some embodiments, the DNAzyme cleaves a single ribonucleotide linkage. In some embodiments, the single ribonucleotide linkage is in a nucleic acid sequence wherein the remaining nucleotides are ribonucleotides. In some embodiments, the single ribonucleotide linkage is in a nucleic acid sequence wherein the remaining nucleotides are deoxyribonucleotides. In some embodiments, the DNAzyme cleaves a nucleic acid sequence at a single ribonucleotide linkage thereby producing a nucleic acid cleavage fragment.

The term "hybridizes", "hybridized" or "hybridization" as used herein refers to the sequence specific non-covalent binding interaction with a complementary, or partially complementary, nucleic acid sequence. When, for example, the 5'-end region of a DNAzyme hybridizes to the 3'-end region, it can form a duplex DNA element.

The term "biosensor" as used herein refers to a device that incorporates a biological entity as a molecular recognition element and is capable of producing a measurable signal upon binding of a target analyte to the molecular recognition element. The biosensor can also be part of a larger device.

The term "functionalizing" or "functionalized on" as used herein refers to various common approaches for functionalizing a material, which can be classified as mechanical, physical, chemical and biological. Any suitable form of coupling can be utilized (e.g. coating, binding, etc.). The functionalized material, for example, a nucleic acid or a blocking species, is also immobilized.

It will be understood that any component defined herein as being included can be explicitly excluded by way of proviso or negative limitation, such as any specific compounds or method steps, whether implicitly or explicitly defined herein.

Although methods and materials similar or equivalent to those described herein can be used in the practice or testing of this disclosure, suitable methods and materials are described below.

II. DNAzymes and Methods of the Disclosure

Disclosed herein is an RNA-cleaving DNAzyme and corresponding RNA-cleaving fluorogenic DNAzyme (RFD) probe that is not only highly specific to *C. difficile* but also capable of recognizing diverse pathogenic *C. difficile* strains. Extensive sequence and structure characterization established a pseudoknot structure and a significantly minimized sequence for this RFD for detecting pathogenic *C. difficile* strains, termed RFD-CD2 hereinafter. As a fluorescent sensor, RFD-CD2 can detect *C. difficile* at a concentration as low as 100 CFU/mL, making this DNAzyme an attractive molecular probe for rapid diagnosis of CDI caused by diverse strains of *C. difficile*.

Accordingly, provided herein is a catalytic nucleic acid comprising a nucleotide sequence selected from the group consisting of SEQ ID NOs: 10-16, 19-21, 23, 29-32, 36, 37, 39-44, and 47, a functional fragment thereof, or a functional variant thereof, for detecting *Clostridium difficile* (*C. difficile*).

In some embodiments, the catalytic nucleic acid comprises the nucleotide sequence selected from the group consisting of SEQ ID NOs: 10-15, 19, 30, 36, 37, 39-43, and 47, a functional fragment thereof, or a functional variant thereof.

In some embodiments, the catalytic nucleic acid comprises the nucleotide sequence selected from the group consisting of SEQ ID NOs: 11, 36, 40-42, and 47, a functional fragment thereof, or a functional variant thereof. In some embodiments, the catalytic nucleic acid comprises the nucleic acid sequence of SEQ ID NO: 10, a functional fragment thereof, or a functional variant thereof. In some embodiments, the catalytic nucleic acid comprises the nucleic acid sequence of SEQ ID NO: 11, a functional fragment thereof, or a functional variant thereof. In some embodiments, the catalytic nucleic acid comprises the nucleic acid sequence of SEQ ID NO: 12, a functional fragment thereof, or a functional variant thereof. In some embodiments, the catalytic nucleic acid comprises the nucleic acid sequence of SEQ ID NO: 13, a functional fragment thereof, or a functional variant thereof. In some embodiments, the catalytic nucleic acid comprises the nucleic acid sequence of SEQ ID NO: 14, a functional fragment thereof, or a functional variant thereof. In some embodiments, the catalytic nucleic acid comprises the nucleic acid sequence of SEQ ID NO: 15, a functional fragment thereof, or a functional variant thereof. In some embodiments, the catalytic nucleic acid comprises the nucleic acid sequence of SEQ ID NO: 16, a functional fragment thereof, or a functional variant thereof. In some embodiments, the catalytic nucleic acid comprises the nucleic acid sequence of SEQ ID NO: 19, a functional fragment thereof, or a functional variant thereof. In some embodiments, the catalytic nucleic acid comprises the nucleic acid sequence of SEQ ID NO: 20, a functional fragment thereof, or a functional variant thereof. In some embodiments, the catalytic nucleic acid comprises the nucleic acid sequence of SEQ ID NO: 21, a functional fragment thereof, or a functional variant thereof. In some embodiments, the catalytic nucleic acid comprises the nucleic acid sequence of SEQ ID NO: 23, a functional fragment thereof, or a functional variant thereof. In some embodiments, the catalytic nucleic acid comprises the nucleic acid sequence of SEQ ID NO: 29, a functional fragment thereof, or a functional variant thereof. In some embodiments, the catalytic nucleic acid comprises the nucleic acid sequence of SEQ ID NO: 30, a functional fragment thereof, or a functional variant thereof. In some embodiments, the catalytic nucleic acid comprises the nucleic acid sequence of SEQ ID NO: 31, a functional fragment thereof, or a functional variant thereof. In some embodiments, the catalytic nucleic acid comprises the nucleic acid sequence of SEQ ID NO: 32, a functional fragment thereof, or a functional variant thereof. In some embodiments, the catalytic nucleic acid comprises the nucleic acid sequence of SEQ ID NO: 36, a functional fragment thereof, or a functional variant thereof. In some embodiments, the catalytic nucleic acid comprises the nucleic acid sequence of SEQ ID NO: 37, a functional fragment thereof, or a functional variant thereof. In some embodiments, the catalytic nucleic acid comprises the nucleic acid sequence of SEQ ID NO: 39, a functional fragment thereof, or a functional variant thereof. In some embodiments, the catalytic nucleic acid comprises the nucleic acid sequence of SEQ ID NO: 40, a functional fragment thereof, or a functional variant thereof. In some embodiments, the catalytic nucleic acid comprises the nucleic acid sequence of SEQ ID NO: 41, a functional fragment thereof, or a functional variant thereof. In some embodiments, the catalytic nucleic acid comprises the nucleic acid sequence of SEQ ID NO: 42, a functional fragment thereof, or a functional variant thereof. In some embodiments, the catalytic nucleic acid comprises the nucleic acid sequence of SEQ ID NO: 43, a functional fragment thereof, or a functional variant thereof. In some embodiments, the catalytic nucleic acid comprises the nucleic acid sequence of SEQ ID NO: 44, a functional fragment thereof, or a functional variant thereof. In some embodiments, the catalytic nucleic acid comprises the nucleic acid sequence of SEQ ID NO: 47, a functional fragment thereof, or a functional variant thereof.

The catalytic nucleic acid described herein possess high sensitivity and specificity. In some embodiments, the catalytic nucleic acid has a limit-of-detection of about 100 CFU/mL *C. difficile*. In some embodiments, the catalytic nucleic acid has a limit-of-detection of about $10^4$ CFU/mL *C. difficile*. In some embodiments, the catalytic nucleic acid does not detect and/or contact *Actinomyces orientalis, Bacillus subtilis, Bacteroid fragilis, Enterobacter aerogenes, Escherichia coli, Pseudomonas aeruginosa, Shigella sonnei, Klebsiella pneumoniae.*

In some embodiments, the catalytic nucleic acid is for cleavage of a nucleic acid substrate.

Provided herein is also a catalytic nucleic acid probe comprising the catalytic nucleic acid disclosed herein and a detectable substrate.

In some embodiments, the detectable substrate comprises a ribonucleotide flanked by a fluorophore modified nucleic acid residue and a quencher modified nucleic acid residue.

In some embodiments, the catalytic nucleic acid probe is configured to generate a fluorogenic signal upon contacting *C. difficile*.

In some embodiments, the detectable substrate comprises the nucleotide sequence of SEQ ID NO: 1 or 76. In some embodiments, the detectable substrate comprises the nucleotide sequence of SEQ ID NO: 1. In some embodiments, the detectable substrate comprises the nucleotide sequence of SEQ ID NO: 76.

In some embodiments, the detectable substrate is at the 5' end of the catalytic nucleic acid.

In some embodiments, the catalytic nucleic acid probe comprises a catalytic nucleic acid comprising a nucleotide sequence selected from the group consisting of SEQ ID NOs: 10-16, 19-21, 23, 29-32, 36, 37, 39-44, and 47, a functional fragment thereof, or a functional variant thereof, and a detectable substrate comprising the nucleotide sequence of SEQ ID NO: 1 or 76 at the 5' end of the catalytic nucleic acid. In some embodiments, the catalytic nucleic acid probe comprises a catalytic nucleic acid comprising a nucleotide sequence selected from the group consisting of SEQ ID NOs: 10-15, 19, 30, 36, 37, 39-43, and 47, a functional fragment thereof, or a functional variant thereof, and a detectable substrate comprising the nucleotide sequence of SEQ ID NO: 1 or 76 at the 5' end of the catalytic nucleic acid. In some embodiments, the catalytic nucleic acid probe comprises a catalytic nucleic acid comprising a nucleotide sequence selected from the group consisting of SEQ ID NOs: 11, 36, 40-42, and 47, a functional fragment thereof, or a functional variant thereof, and a detectable substrate comprising the nucleotide sequence of SEQ ID NO: 1 or 76 at the 5' end of the catalytic nucleic acid. In some embodiments, the catalytic nucleic acid probe comprises a catalytic nucleic acid comprising a nucleotide sequence selected from the group consisting of SEQ ID NOs: 11 and 47, a functional fragment thereof, or a functional variant thereof, and a detectable substrate comprising the nucleotide sequence of SEQ ID NO: 1 or 76 at the 5' end of the catalytic nucleic acid.

In some embodiments, the catalytic nucleic acid probe comprises the nucleotide sequence selected from the group consisting of SEQ ID NOs: 48-53 and 70-75, a functional fragment thereof, or a functional variant thereof. In some embodiments, the catalytic nucleic acid probe comprises the nucleotide sequence selected from the group consisting of SEQ ID NOs: 48, 49, and 53. In some embodiments, the catalytic nucleic acid probe comprises the nucleotide sequence selected from the group consisting of SEQ ID NOs: 48 and 53, a functional fragment thereof, or a functional variant thereof. In some embodiments, the catalytic nucleic acid probe comprises the nucleotide sequence selected from the group consisting of SEQ ID NOs: 70, 71, and 75. In some embodiments, the catalytic nucleic acid probe comprises the nucleotide sequence selected from the group consisting of SEQ ID NOs: 70 and 75, a functional fragment thereof, or a functional variant thereof. In some embodiments, the catalytic nucleic acid probe comprises the nucleotide sequence of SEQ ID NO: 48, a functional fragment thereof, or a functional variant thereof. In some embodiments, the catalytic nucleic acid probe comprises the nucleotide sequence of SEQ ID NO: 49, a functional fragment thereof, or a functional variant thereof. In some embodiments, the catalytic nucleic acid probe comprises the nucleotide sequence of SEQ ID NO: 50, a functional fragment thereof, or a functional variant thereof. In some embodiments, the catalytic nucleic acid probe comprises the nucleotide sequence of SEQ ID NO: 51, a functional fragment thereof, or a functional variant thereof. In some embodiments, the catalytic nucleic acid probe comprises the nucleotide sequence of SEQ ID NO: 52, a functional fragment thereof, or a functional variant thereof. In some embodiments, the catalytic nucleic acid probe comprises the nucleotide sequence of SEQ ID NO: 53, a functional fragment thereof, or a functional variant thereof. In some embodiments, the catalytic nucleic acid probe comprises the nucleotide sequence of SEQ ID NO: 70, a functional fragment thereof, or a functional variant thereof. In some embodiments, the catalytic nucleic acid probe comprises the nucleotide sequence of SEQ ID NO: 71, a functional fragment thereof, or a functional variant thereof. In some embodiments, the catalytic nucleic acid probe comprises the nucleotide sequence of SEQ ID NO: 72, a functional fragment thereof, or a functional variant thereof. In some embodiments, the catalytic nucleic acid probe comprises the nucleotide sequence of SEQ ID NO: 73, a functional fragment thereof, or a functional variant thereof. In some embodiments, the catalytic nucleic acid probe comprises the nucleotide sequence of SEQ ID NO: 74, a functional fragment thereof, or a functional variant thereof. In some embodiments, the catalytic nucleic acid probe comprises the nucleotide sequence of SEQ ID NO: 75, a functional fragment thereof, or a functional variant thereof.

In some embodiments, the catalytic nucleic acid probe is for use in screening and/or diagnostics, environmental monitoring, health monitoring, and/or pharmaceutical development. In some embodiments, the catalytic nucleic acid probe is for use in screening, diagnostics, and/or health monitoring of *C. difficile* infection.

The catalytic nucleic acid and the catalytic nucleic acid probe described herein can be incorporated into a biosensor useful for detecting *C. difficile*. Also provided herein is a biosensor for detecting *C. difficile* comprising the catalytic nucleic acid disclosed herein, or the catalytic nucleic acid probe disclosed herein, functionalized on and/or in a material.

In some embodiments, the biosensor is a fluorogenic biosensor, a colorimetric biosensor, or an electrochemical biosensor. In some embodiments, the biosensor is a lateral flow device.

Also provided herein is a method for detecting the presence of *C. difficile* in a sample, the method comprising:

a) combining the sample with the catalytic nucleic acid probe of claim 6 in a liquid to form a mixture;

b) incubating the mixture to allow for a cleavage reaction in which the catalytic nucleic acid cleaves the detectable substrate, thereby releasing a fragment comprising a quencher modified nucleic acid residue to produce a fluorogenic signal;

c) optionally quenching the cleavage reaction;

d) detecting the fluorogenic signal and/or a cleaved fragment;

wherein detecting the fluorogenic signal and/or the cleaved fragment indicates presence of *C. difficile* in the sample.

In some embodiments, b) comprises incubating the mixture at about 37° C. In some embodiments, the liquid is a buffer. In some embodiments, the buffer comprises a divalent ion. In some embodiments, the divalent ion is $Mg^{2+}$. In some embodiments, the buffer comprises from about 5 mM to about 100 mM, about 5 mM to about 100 mM, about 10 mM to about 90 mM, about 20 mM to about 80 mM, about 30 mM to about 70 mM, about 40 mM to about 60 mM, or about 45 mM to about 55 mM $Mg^{2+}$. In some embodiments, the buffer comprises about 50 mM $Mg^{2+}$.

In some embodiments, the buffer is from about pH 5.0 to about pH 9.0, about pH 6.0 to about pH 9.0, about pH 7.0 to about pH 9.0, about pH 7.5 to about pH 9.0, about pH 7.5 to about pH 8.5, or about pH 7.8 to about pH 8.2. In some embodiments, the buffer is about pH 8.0.

In some embodiments, the mixture is incubated at about 37° C. for about 1 hour to about 4 hours to allow a ribonucleotide linkage cleavage reaction to occur.

In some embodiments, quenching of the cleavage reaction comprises adding a quenching buffer to the mixture. In some embodiments, the quenching buffer comprises EDTA and/or urea. In some embodiments, the EDTA concentration is from about 5 mM to about 200 mM, about 10 mM to about 150 mM, about 10 mM to about 100 mM, about 10 mM to about 80 mM, about 10 mM to about 60 mM, about 15 mM to about 50 mM, about 20 mM to about 40 mM, about 20 mM to about 35 mM, or about 25 mM to about 35 mM. In some embodiments, the EDTA concentration is about 30 mM. In some embodiments, the quenching buffer comprises EDTA, urea, and loading buffer. In some embodiments, the loading buffer comprises HEPES.

In some embodiments, the cleavage reaction is quenched by heating the mixture. In some embodiments, the heating is at about 90° C. or more. In some embodiments, the heating is at about 90° C. or more for about 3 minutes.

The fluorogenic signal can be detected by a fluorescence assay, which allows for quantitative or qualitative analysis. One method is fluorescence spectroscopy, which involves exciting a sample with a specific wavelength of light, causing the molecules within to emit light at a longer wavelength, which is then captured and analyzed. Another method is flow cytometry, which involves analysis of the physical and chemical characteristics of particles in a fluid as they pass through at least one laser. Each particle passes through the laser beam individually, and both the light scattered from each particle and any fluorescent light emitted are collected and analyzed. A fluorescence assay can also employ a fluorimeter, which detects and measures the fluorescence emitted by samples when excited by light. This device typically incorporates a light source and a detector, often a photodiode or a photomultiplier tube, to excite fluorescent dyes within the sample and then record the intensity of the light emitted. Those skilled in the art can readily recognize a fluorescence assay, along with any associated instruments and separation techniques, such as denaturing polyacrylamide gel electrophoresis, which are useful for detecting the fluorogenic signal and cleaved fragments generated by the catalytic nucleic acid described herein. In some embodiments, detecting the fluorogenic signal comprises analysis via a fluorescence assay. In some embodiments, detecting the fluorogenic signal comprises analysis via fluorescence spectroscopy. In some embodiments, detecting the fluorogenic signal comprises analysis via flow cytometry. In some embodiments, detecting a fluorogenic signal comprises analysis using a fluorimeter. In some embodiments, detecting the fluorogenic signal comprises analysis via denaturing polyacrylamide gel electrophoresis.

In some embodiments, the method detects *C. difficile* infection in a subject.

In some embodiments, the sample is a stool sample. In some embodiments, the stool sample is a fresh stool sample. In some embodiments, the stool samples is a refrigerated stool sample. In some embodiments, the sample comprises feces.

Also provided herein is a kit for detecting *C. difficile* in a sample, wherein the kit comprises the catalytic nucleic acid probe disclosed herein, the biosensor disclosed herein, or components required for the method disclosed herein, and instructions for use of the kit. In some embodiments, the kit further comprises reagents and/or solutions, such as at least one buffer, to provide conditions for cleavage by the catalytic nucleic acid described herein. In some embodiments, the buffer comprises a reaction buffer. In some embodiments, the reaction buffer is a HEPES buffer. In some embodiments, the reaction buffer comprises a divalent cation. In some embodiments, the divalent cation is $Mg^{2+}$. In some embodiments, the buffer comprises a quenching buffer. In some embodiments, the quenching buffer comprises a chelator or a denaturant. In some embodiments, the chelator is EDTA. In some embodiments, the denaturant is urea. In some embodiments, the kit further comprises a test sample collection device. In some embodiments, the sample collection device is a swab or a container. In some embodiments, the kit comprises a label for identifying a sample. In some embodiments, the kit comprises a package for the kit.

Also provided herein is an isolated nucleic acid comprising a nucleotide sequence selected from the group consisting of SEQ ID NOs: 1-76, a nucleotide sequence shown in Tables 2, 4, 5, 7, 9, and 10, or a functional fragment thereof, or a functional variant thereof.

Also provided herein is use of the catalytic nucleic acid, the catalytic nucleic acid probe, the biosensor, or the kit disclosed herein, to determine the presence of *Clostridium difficile*.

EXAMPLES

The following non-limiting Examples are illustrative of the present disclosure:

Methods

Materials and Reagents. Substrate sequence QRF30, libraries for selection and reselection were synthesized by Yale University Keck Facilities. All other oligonucleotides listed in Table 2, 4, and 7 were synthesized by IDT (Integrated DNA Technologies, Coralville, IA, USA). Oligo sequences were purified by 10% denaturing (8 M urea) polyacrylamide gel electrophoresis (dPAGE) before use. T4 polynucleotide kinase (PNK), T4 DNA ligase, and proteinase K were purchased from Thermo Scientific (Ottawa, ON, Canada). *Thermus aquaticus* (Taq) DNA polymerase and standard Taq reaction buffer were from New England BioLabs (Ipswich, Massachusetts, United States). Urea (ultrapure) and 40% polyacrylamide solution (29:1) were acquired from BioShop Canada (Burlington, ON, Canada). The water used was purified via Milli-Q Synthesis A10 water purifier. All other chemicals were purchased from Bioshop Canada and used without further purification. Centrifugal devices were purchased from Amicon with nominal molecular weight limit (NMWL) from 3K (3000 Daltons), 10K, 30 K, 50K, and 100K.

Bacterial strains and culture conditions. *C. difficile* strains, BAA-1870 (NAP1), BAA-1803 (NAP1), BAA-1871 (NAP2), BAA-1872 (NAP4), BAA-1875 (NAP7), BAA-1814, 51695 and 43594 were obtained from the American Type Culture Collection (ATCC; Manassas, Va.); 20309 was purchased from CCUG (Culture Collection University of Gothenburg). *E. coli* strain was *E. coli* K12. *K. aerogenes* was a gift from Professor Gerard Wright (Michael G. DeGroote Institute for Infectious Disease Research, McMaster University). Other bacteria used in this study were routinely cultured and maintained in-laboratory. *C. difficile* strains were streaked on cooked meat broth (CMB) agar plate from a frozen glycerol stock and anaerobically cultured at 37° C. for 2 days. A single colony was then inoculated into 5 mL liquid CMB for 48-hour anerobic culture at 37° C. Other anaerobic bacteria were cultured in the same way. Aerobic bacteria were cultured in lysogeny broth (LB) media at 37° C. until $OD_{600}$ reached ~1.0.

Preparation of bacteria crude extracellular mixture (CEM). For anaerobic bacteria, liquid culture was collected after 48-hour culture; for aerobic bacteria culture, the liquid culture was collected at $OD_{600}$~1.0. The collected liquid culture was centrifuged at 11,000 g for 5 minutes. CEM was obtained by passing the supernatant through 0.22 μm filter. CEM aliquots were stored at −80° C.

In vitro selection. In vitro selection was performed as previously introduced. Briefly 1 nmol of purified library was phosphorylated by 20 units of PNK in the presence of ATP in 1×PNK buffer at 37° C. for 20 minutes. The reaction was quenched by heating the reaction mixture at 90° C. for 5 minutes. After cooling down to room temperature, 1.1× molar substrate and splint sequence were added and properly mixed. The mixture was heated at 90° C. for 2 minutes and cooled to room temperature. 20 units of T4 DNA ligase and 10×T4 ligase buffer were added to the mixture, which was incubated for 2 hours. The resulting reaction mixture was then quenched by heating at 90° C. for 5 minutes. The ligated sequence was separated by 10% dPAGE gel. The purified library was then incubated with unintended targets in 1× selection buffer (1×SB) (50 mM HEPES, pH 7.5, 150 mM NaCl, 15 mM $MgCl_2$, and 0.01% Tween 20) in the counter selection step. After ethanol precipitation, the uncleaved sequence was purified by 10% dPAGE gel and dissolved in $ddH_2O$ for position selection. The DNA library was then incubated with CEM-NAP1 at room temperature in 1×SB. The reaction was quenched by a stop solution with 100 mM EDTA and 8 M urea. After ethanol precipitation, the cleavage products were separated by 10% dPAGE, dissolved in 10 μL of $ddH_2O$, and stored at −20° C. The PCR1 mixture (50 μL) contained 4 μL of the template prepared above, 0.5 μM each of forward primer FP1 and reverse primer RP1, 200 μM each of dNTPs (dATP, dCTP, dGTP and dTTP), 1×PCR buffer (10 mM Tris-HCl, pH 8.3, 1.5 mM $MgCl_2$, 50 mM KCl) and 2.5 units of Taq DNA polymerase. The DNA was amplified using the following thermocycling steps: 94° C. for 1 minute; 11-13 (dependent on the amount of cleavage of the DNA pool) cycles of 94° C. for 45 seconds, 53° C. for 45 seconds and 72° C. for 45 seconds; 72° C. for 1 minute. For the PCR2 reaction, 1 μL of the PCR1 product was diluted with $ddH_2O$ to 20 μL, 2-5 μL of which was used as the template for PCR2. The PCR 2 mixture (50 μL×8 to generate enough DNA) used the same recipe, but the reverse primer RP1 was replaced with RP2. The amplified sense strand was purified by 10% dPAGE and used for the next round of selection. Sequence details are provided in Table 1.

High-throughput sequencing. The cleaved product from round 7 in selection was amplified by PCR with Illumina sequencing primers. PCR products were purified by 2% agarose gel electrophoresis and extracted from gel with GenElute Gel Extraction Kit (Sigma Aldrich). Purified samples were sequenced with paired-end next-generation sequencing (NGS) with an Illumina MiSeq system. Sequence data was processed with Geneious after primer trimming. PrinSeq v0.20.4 was used to obtain high-quality reads of top candidate sequences.[42] Only sequences with base-call probability >=99% were recorded. A clustering algorithm CD-HIT-EST was applied to group the obtained sequences into clusters (also known as classes) with the following input parameter: identity threshold (-c), 0.9; word length (-n), 7; (-d), 0; (-g), 1.[43] Grouped classes were ranked by their reads from highest to lowest in the pool. The round-6 cleavage product in reselection was sequenced as previously published.[44]

Cleavage reactions. Before reaction condition improvement, a typical cleavage reaction was composed of 1 μL of 1 μM RFD-CD2, 4 μL of CEM-NAP1, and 5 μL of 2× selection buffer (SB) (100 mM HEPES, pH 7.5, 300 mM NaCl, 30 mM $MgCl_2$ and 0.02% Tween 20). After incubation at room temperature (22° C.) for 4 hours, the reaction was quenched by 2× quenching buffer (QB), a solution with 60 mM EDTA, 14 M urea and loading dye. The quenched reaction mixture was heated at 90° C. for 3 minutes and then loaded onto 10% dPAGE gel. The gel image was obtained with a Typhoon Amersham imager (GE Healthcare) at Centre for Microbial Chemical Biology (CMCB) McMaster University with the following imaging parameters: emission filter: 526 SP Fluorescein, Cy2, AlexaFluor488; laser: blue (488 nm); PMT: 400; Focal plane: +3; 200 pixels. The images were quantified using ImageJ software. The percent cleavage of RFD-CD2 was calculated with the following formulas: $\% \text{ Clv}=(FI_{Clv}/6)/[(FI_{Clv}/6)+FI_{Unclv}]$. $FI_{Clv}$: fluorescence intensity of cleaved band; $FI_{Unclv}$: fluorescence intensity of uncleaved band.

After reaction condition improvement, the cleavage reaction was typically composed of 1 μL of 1 μM RFD-CD2, 4 μL of CEM-NAP1, and 5 μL of 2× improved Reaction Buffer 2 (RB2) (100 mM HEPES, pH 8.0, 300 mM NaCl, 100 mM $MgCl_2$ and 0.02% Tween 20). The cleavage reaction was incubated at 37° C. for 4 hours and then quenched by QB. The cleavage reaction mixture was then analyzed by 10% dPAGE, and quantified with Typhoon 9200 and ImageJ.

Reaction condition improvement. For magnesium concentration test, 2× selection buffer' (SB') (100 mM HEPES, pH 7.5, 300 mM NaCl, 0.02% Tween 20 with various magnesium concentrations) were prepared. The reaction was composed of 1 μL of 1 μM RFD-CD2, 4 μL of CEM-NAP1 and 5 μL of 2×SB'. Tested magnesium final concentrations were 0, 0.125, 0.25, 0.5, 0.75, 1, 5, 7.5, 10, 15, 20, 25, 50, 100, and 200 mM. Reactions were carried out at 22° C. for 24 hours and then quenched by QB. For reaction temperature test, the reaction system was composed of 1 μL of 1 μM RFD-CD2, 4 μL of CEM-NAP1 and 5 μL of 2×RB1 (100 mM $MgCl_2$, 300 mM NaCl, 100 mM HEPES, pH 7.5, and 0.02% Tween 20). Cleavage reactions were performed at 4° C., 22° C., 37° C., 50° C. and 65° C. separately for 24 hours and quenched by QB. For pH test, the reaction mixture was composed of 1 μL of 1 μM RFD-CD2, 4 μL of CEM-NAP1 and 5 μL of 2×pH buffer' (100 mM buffering agent, 300 mM NaCl, 100 mM $MgCl_2$ and 0.02% Tween 20). The buffering agents used were MES at pH 5.0, 5.5, 6.0, HEPES at pH 6.5, 7.0, 7.5, 8.0 and Tris at pH 7.5, 8.0, 8.5, 9.0. Cleavage reactions were at 22° C. for 24 hours and quenched by QB.

Kinetic analysis of DNAzymes. One cleavage reaction master mixture (120 μL) was prepared with 12 μL of 1 μM RFD-CD2, 48 μL of CEM-NAP1, and 60 μL of 2×SB or 2×RB2. The cleavage reaction under the original selection conditions was performed at room temperature (22° C.); all other reactions were done at 37° C. The timepoints were 30, 60, 90, 120, 150, 180, 240, 360, 480, 960, 1440, 1800 minutes or 0.5, 1, 2.5, 5, 10, 15, 20, 30, 60, 120 minutes. A 10-μL aliquot was taken from the master reaction mixture at a time point and quenched with QB. The quenched reaction mixture was then heated at 90° C. for 3 minutes for 10% dPAGE analysis. The gel imaging and quantification process was the same as described above. Percent cleavage of RFD-CD2 versus reaction time was plotted, and non-linear fitting (one phase exponential association) was applied to the data using the equation of $Y=Y_{max}[1-e^{-kt}]$ in Prism (GraphPad, 4.03). $Y_{max}$ represents the maximal cleavage yield and k is the observed first-order rate constant ($k_{obs}$).

Target identification. To investigate the nature of the target of RFD-CD2, 1 μL of 20 mg/mL proteinase K was mixed with 4 μL of CEM-NAP1 and 5 μL of 2×RB2. The mixture was incubated at room temperature for 1 hour. After the incubation, 1 μL of 1 μM RFD-CD2 was added to the solution, which was further incubated at 37° C. for 4 hours. The reaction was quenched by QB and the mixture was subjected to 10% dPAGE analysis. To examine the thermostability of the target molecule, CEM-NAP1 was heated at 90° C. for 5 and 10 minutes. After cooling down to room temperature, 4 μL of heated and non-heated CEM-NAP1 were incubated with 1 μL of 1 μM RFD-CD2 and 5 μL of 2×RB2. Aliquots of 0.4 mL CEM-NAP1 was filled into Amicon Ultra-0.5 mL Centrifugal Filters and centrifuged at 14,000 g. The filtrate (the liquid that passed through the filter) and the concentrate of each column were separately collected and incubated with RFD-CD2 as described above.

Specificity test. CEMs from relevant bacteria were prepared in the same way as described above for the preparation of CEM-NAP1. 4 μL of each bacterial CEM was incubated with 1 μL of 1 μM RFD-CD2 and 5 μL of 2×RB2 at 37° C. for 4 hours. The reaction was quenched by QB and the reaction mixture was analyzed by 10% dPAGE.

Sensitivity test. A single colony of NAP1 on CMB agar plate was inoculated into 5 mL of liquid CMB. After 48-hour growth, *C. difficile* culture was serially diluted 10 times. 100 μL of each dilution was streaked out on a CMB agar plate with triplicate. Plates with 30-300 colonies were counted and triplicates were averaged for concentration calculation (CFU/mL). Based on this diluted concentration, the concentration at other dilutions was calculated. CEMs at each dilution were prepared from their corresponding culture.

The fluorescence assay was performed on infinite 200Pro and the fluorescence intensity was read by Tecan i-control (2.0.10.0). The excitation wavelength was 488 nm and the emission wavelength was 520 nm. The fluorescence intensity was recorded every 15 minutes for 4 hours. For each dilution, the fluorescence intensity of the CEM was measured as $F_b$. The fluorescence intensity of the DNAzyme cleavage reaction mixture at a given timepoint was measured as F. The fluorescence intensity of the DNAzyme cleavage reaction mixture at the starting point (0 min) was measured as $F_0$. The relative fluorescence intensity was calculated using the equation of $(F-F_b)/(F_0-F_b)$.

Reselection. The reselection protocol was similar to the original selection protocol except for the use of a different starting pool and a different set of reverse primers (see Table 5).

Results and Discussion

Figure 1A:
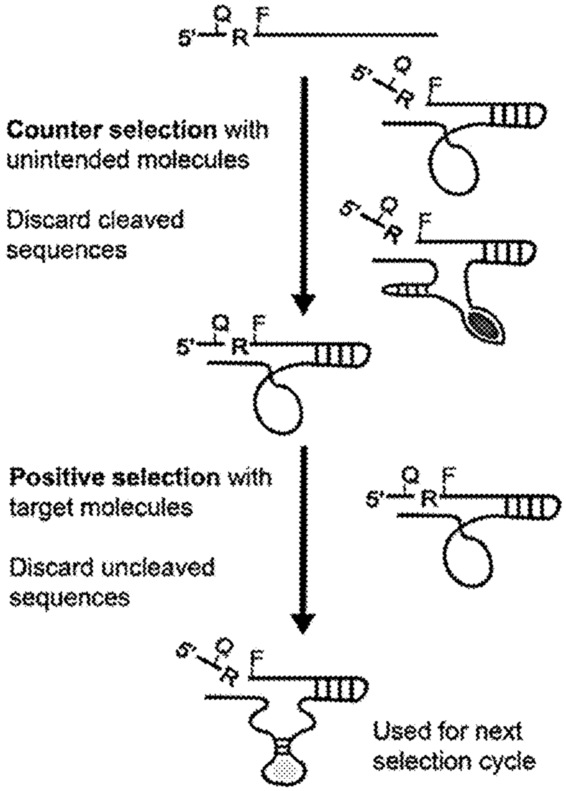
Figure 2:
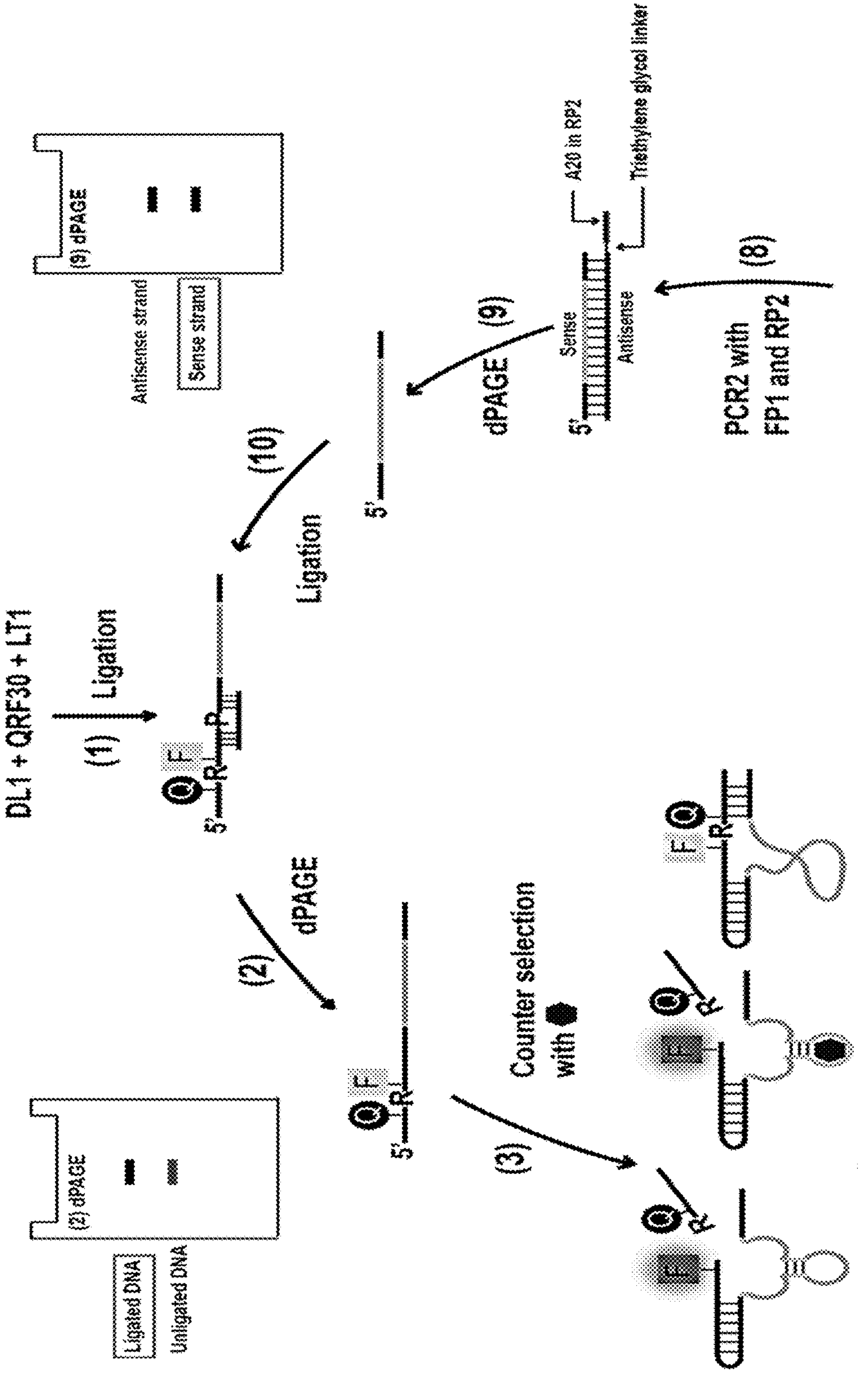
Figure 2:
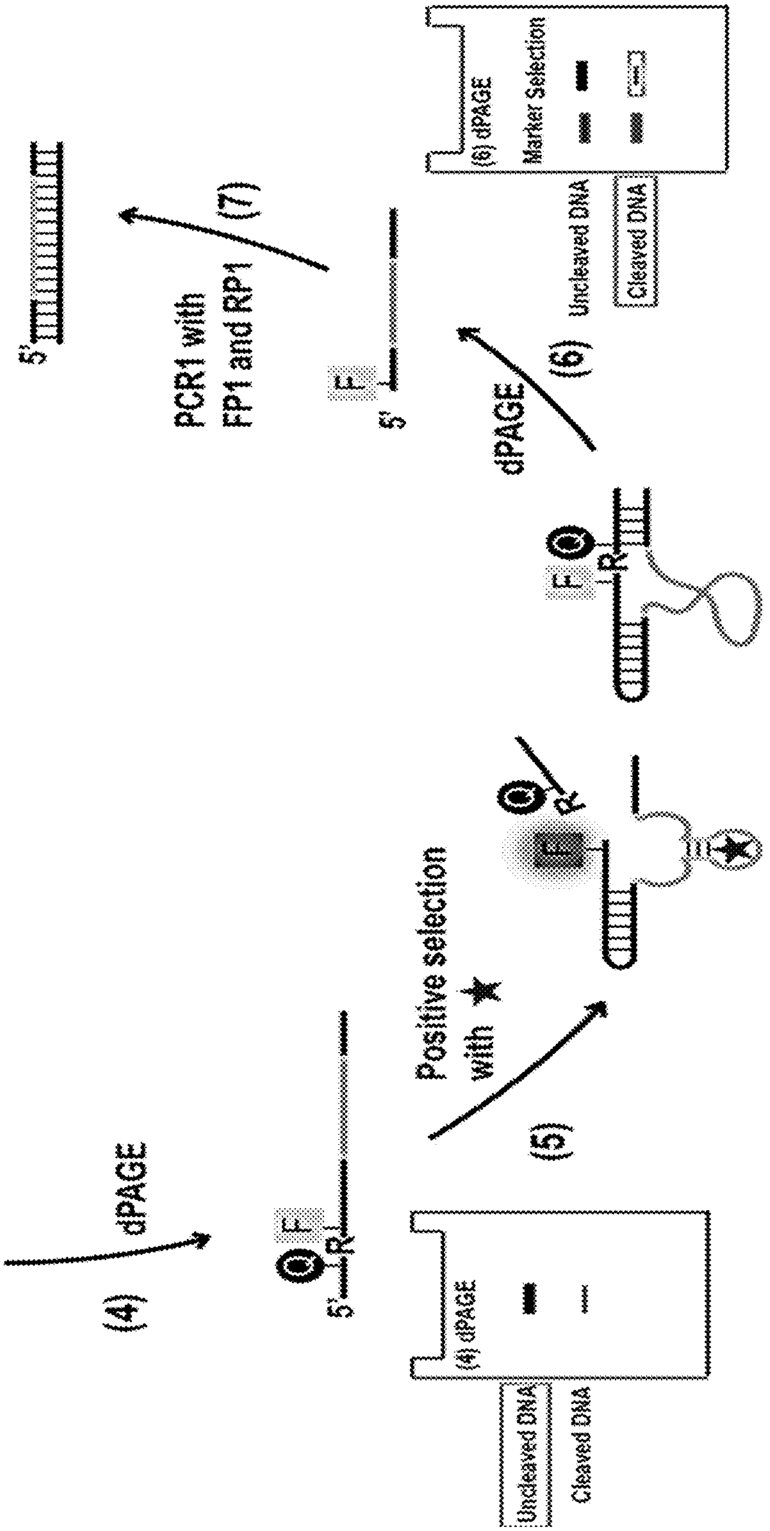

RFD-CD2 isolation via in vitro selection. An in vitro selection was performed to isolate DNAzymes specifically targeting *C. difficile* from a random-sequence DNA pool (a simplified selection strategy is illustrated in FIG. 1A; the detailed selection scheme is given in FIG. 2; the sequences of all synthetic oligonucleotides used for the selection experiment are provided in Table 1). The DNA library (termed DL1 hereinafter) contains a 50-nucleotide (nt) random-sequence domain flanked with two 20-nt constant primer regions for PCR. DL1 was ligated to a 30-nt chimeric DNA/RNA sequence containing a single RNA unit (R, adenosine ribonucleotide) as well as a pair of thymidine nucleotides modified with a quencher (Q, dabcyl) and a fluorophore (F, FAM) that flank the RNA site (termed QRF30 hereinafter). The ligated chimeric and labeled DNA library, termed QRF30-DL1 hereinafter, was used as the initial pool for the selection of *C. difficile*-responsive RFD molecules.

Figure 3:
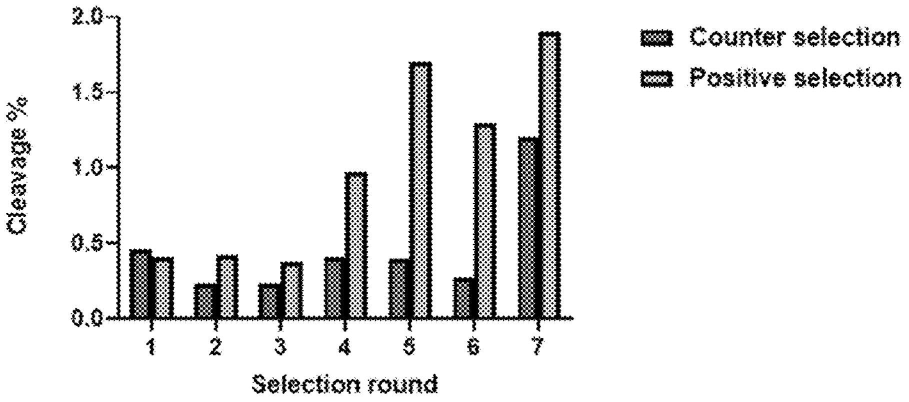

A total of 7 rounds of selection was conducted with an original goal of isolating RFDs that can be activated by a hypervirulent *C. difficile* strain BAA-1870 (also known as BI/NAP1/027 or simply NAP1). The progress of the selection is provided in FIG. 3 and Table 8. There were two important RNA cleavage steps in each round of selection: the cleavage reaction in the counter-selection step and the cleavage reaction in the positive-selection step. The positive selection in each round was always conducted with the crude extracellular mixture prepared from NAP1, termed CEM-NAP1 hereinafter. However, the counter-selection step was varied in different rounds for different reasons. In the round one, the initial DNA pool was first incubated with selection buffer (SB; 15 mM $MgCl_2$, 150 mM NaCl, 50 mM HEPES, pH 7.5); this step served as the counter-selection step with the intention to remove target-independent self-cleaving RFDs. The uncleaved QRF30-DL1 was purified by denaturing (8 M urea) polyacrylamide gel electrophoresis (dPAGE) and incubated with CEM-NAP1 in the positive-selection step where NAP1-responsive RFD molecules were expected to cleave. The cleaved product was then purified by dPAGE, amplified by PCR using a double-PCR. After a dPAGE-based purification step, the DNAzyme-coding strand from the double-stranded DNA amplicon was used as the DNA pool to initiate the second round of selection. In rounds 2 and 3, the counter-selection was conducted with SB containing cooked meat broth (CMB) media; because *C. difficile* was cultured in CMB, this step was intended to remove any RFDs that can recruit an activating target present in CMB. In rounds 4-7, the counter-selection step was done with the CEM prepared from NAP2 (BAA-1871), NAP4 (BAA-1872) and NAP7 (BAA-1875), three other strains of *C. difficile*, with a goal of deriving RFDs that can be turned on by NAP1 but not by NAP2, NAP4 and NAP7. The cleavage product from the positive-selection step from round 7 was sent for deep sequencing.

Figure 1B:
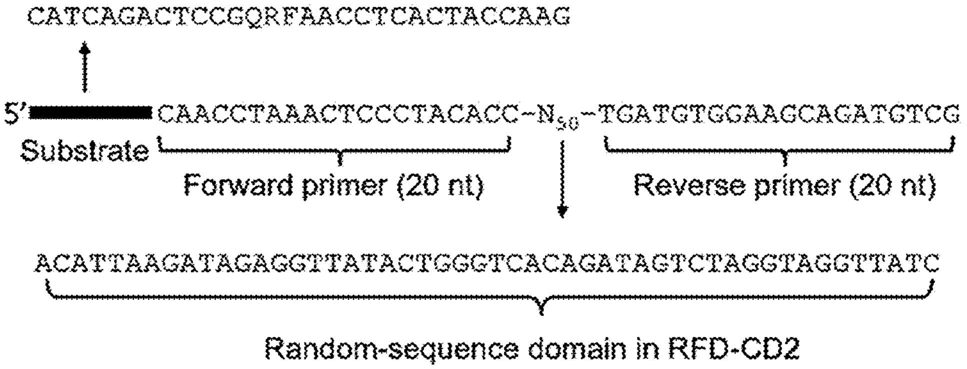
Figure 1C:
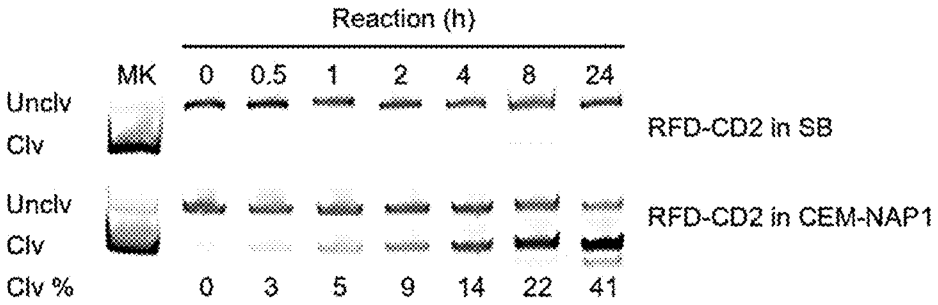
Figure 1D:
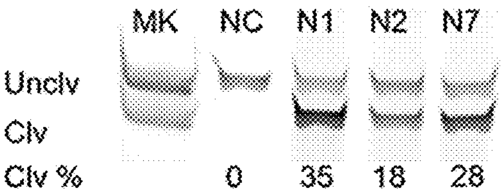
Figure 4:
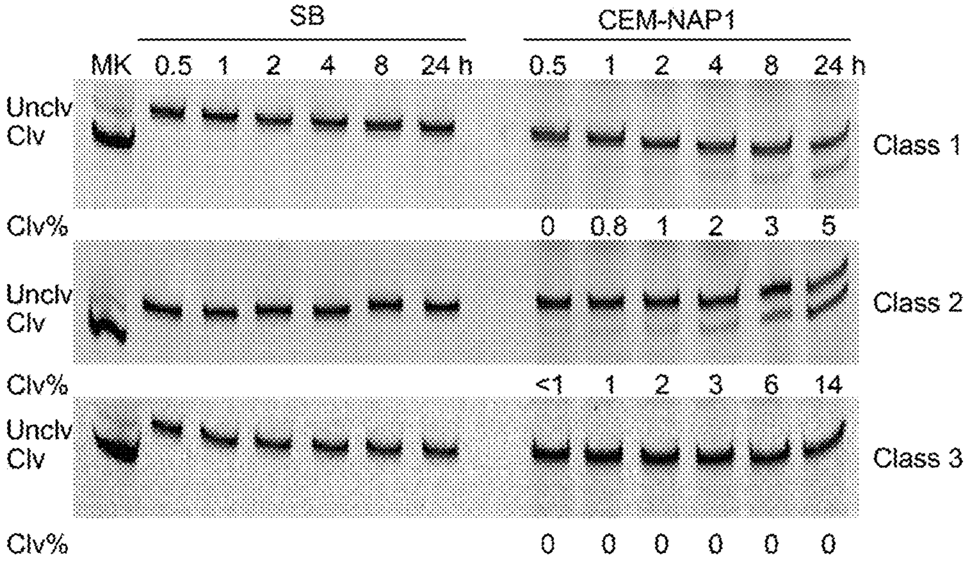

Several candidate DNAzymes were discovered from pool 7 (Table 2). These sequences were assessed for RNA-cleaving activities in SB with and without CEM-NAP1 (FIG. 4). Class 2 DNAzyme exhibited the highest cleavage activity among tested candidates. This DNAzyme, which is named RFD-CD2 (FIG. 1B), is interesting for two reasons. First, as shown in FIG. 1C, RFD-CD2 displayed no cleavage activity in SB only even after 24-hour incubation. In contrast, in the presence of CEM-NAP1, a cleavage signal was detected after only 30-minute incubation, and exhibited a time-dependent increase and reached 41% cleavage after 24-hour incubation. As shown in FIG. 1D, RFD-CD2 did not show strain-selectivity, as it was able to cleave in the presence of the CEM from NAP1, NAP2 and NAP7, despite the fact that the mixture of CEM-NAP2, CEM-NAP4 and CEM-NAP7 was used as the counter-selection target from round 4 to round 7 and the expectation that such a selection protocol would generate DNAzymes that were selective for NAP1. The behavior of RFD-CD2 is in stark contrast with previously reported DNAzyme RFD-CD1, which is highly specific towards the BI/027-H (Hamilton) strain of *C. difficile*.[21] Therefore, a comprehensive characterization study of RFD-CD2 was conducted as it represents a new *C. difficile*-specific RFD that can be broadly activated by diverse *C. difficile* strains.

Reaction condition improvement. RFD-CD2 was active in SB containing CEM-NAP1, but it was only able to achieve ~40% cleavage in 24 hours. One way to improve its performance is to establish its reaction conditions. For this reason, its dependence on metal ions, reaction temperature, and pH was examined. The data from these experiments are presented in FIG. 5.

Divalent metal ions are often an essential cofactor for RNA-cleaving DNAzymes.[24] Various divalent metal ions can have a significant effect on the catalytic performance of a DNAzyme. Different metal ions were tested to find the one that best supports the activity of RFD-CD2 in the presence of CEM-NAP1. Nine tested metal ions were: $Mg^{2+}$, $Co^{2+}$, $Mn^{2+}$, $Cd^{2+}$, $Zn^{2+}$, $Cu^{2+}$, $Ni^{2+}$, $Ba^{2+}$, and $Ca^{2+}$ (15 mM; FIG. 6). RFD-CD2 showed the best cleavage activity in the presence of $Mg^{2+}$ (10-40 fold higher than other metal ion-promoted activities). This DNAzyme was originally selected in SB containing 15 mM $Mg^{2+}$. Therefore, $Mg^{2+}$ was chosen as the divalent metal ion for RFD-CD2 for further experiments.

RFD-CD2 was then examined for activity in SB containing $Mg^{2+}$ concentrations ranging from 0 to 200 mM (FIG. 5A). The cleavage percentage obtained at each concentration was normalized to that at 15 mM. The cleavage activity increased as the concentration of $Mg^{2+}$ was increased from 0 mM to 50 mM. After peaking at 50 mM (normalized activity ~120%), the cleavage activity experienced a gradual decrease; for example, only ~50% normalized activity was observed at 200 mM $Mg^{2+}$. Therefore, 50 mM $Mg^{2+}$ was finalized as the $Mg^{2+}$ concentration to set up the improved Reaction Buffer 1 (RB1) for RFD-CD2.

The improved reaction temperature of RFD-CD2 was next examined by incubating RFD-CD2 with CEM-NAP1 at 4° C., 22° C., 37° C., 50° C., and 65° C. in RB1 (FIG. 5B). The cleavage percentage achieved at each temperature was normalized to that at 22° C. (room temperature, which was the temperature used for the DNAzyme selection experiment). RFD-CD2 produced the highest activity at 37° C. (110%) and the next highest activity at 22° C. (100%). Decreasing the reaction temperature to 4° C. or increasing it to 50° C. and 65° C. caused significant reduction in the cleavage activity. 37° C. was then chosen as the improved temperature for RFD-CD2.

The cleavage activity of RFD-CD2 at different pH conditions was examined next (FIG. 5C). The cleavage percentage obtained under pH 7.5 (HEPES) was normalized as 100%. RFD-CD2 exhibited robust activity between pH 7.5-8.5 but showed much weakened activity in acidic environment (<10% normalized activity under pH 6.0). The activity reached its maximum at pH 8.0, then dropped to ~75% at pH 8.5. To examine if the buffering agent can affect the performance of RFD-CD2, both HEPES and Tris were used to prepare the reaction buffer at pH 7.5 and pH 8.0. However, the activity gap in the reaction buffers prepared from both buffering agents was undetectable. Based on these findings, HEPES at pH 8.0 was chosen to set up the improved Reaction Buffer 2 (RB2; 50 mM $MgCl_2$, 150 mM NaCl, 50 mM HEPES, pH 8.0) for RFD-CD2.

The kinetic profile RFD-CD2 was then compared in SB and RB2 (FIG. 5D). The $k_{obs}$ in SB was determined to be $9\times10^{-4}$ $min^{-1}$; it doubled to $2\times10^{-3}$ $min^{-1}$ in RB2. The $k_{obs}$ value observed under improved reaction conditions ($2\times10^{3}$ $min^{-1}$) is still 20 times smaller than that seen with Lp1F5' ($4\times10^{-2}$ $min^{-1}$), one of the best bacteria-responding DNAzymes reported, which can be specifically activated by the bacterium *Legionella pneumophila*.[39] To assess if the reduced $k_{obs}$ value may be caused by the unsaturated binding between the DNAzyme and its target, CEM-NAP1 was concentrated 23 times using a spin column; the concentrated CEM-NAP1 was then incubated with RFD-CD2. Under this condition, RFD-CD2 produced a $k_{obs}$ of $9\times10^{-2}$ $min^{-1}$ (FIG. 5E), a much-improved catalytic rate constant, which is even better than that of Lp5.

Target identification for RFD-CD2. RFD-CD2 was isolated using CEM-NAP1 as the complex target based on the assumption that one or more molecules in CEM-NAP1 would function as the binding partner to induce the cleavage activities of the DNAzymes to be isolated. As a mixture, CEM-NAP1 contains a large variety of molecules secreted by bacteria. Previous experiments with other RFDs have revealed that the activating targets for bacteria-responding RFDs have been protein molecules.[21,37-41,45] Based on this knowledge, further studies focused on investigating if the activating molecule for RFD-CD2 was also a protein molecule.

Proteinase K was used to degrade protein molecules in CEM-NAP1. The proteinase K-treated CEM was not able to induce the cleavage activity of RFD-CD2 (FIG. 7A), showing that RFD-CD2 indeed recruited a protein molecule as the binding partner. Additional supporting evidence came from a heat-inactivation experiment: when CEM-NAP1 was heated at 90° C. for 5 minutes prior to the incubation with RFD-CD2, the cleavage activity was not detected at all (FIG. 7B).

Spin columns with membrane filters of varying molecule-weight cut-offs were applied next to estimate the molecular weight of the target protein, an approach that was previously applied to estimate molecular weights of RFD-activating protein targets.[21,37-41,45] Molecules larger than the pore size of the membrane-based filter were expected to remain on top of the membrane upon centrifugation (which was collected as the concentrate fraction or "C" fraction), while other molecules would pass through the membrane (which was collected as the filtrate fraction or "F" fraction). Multiple F and C fractions were produced by subjecting CEM-NAP1 through centrifugation with membranes with pore sizes of 3, 10, 30, 50 and 100 kDa (kilo Dalton). For example, upon centrifugation of CEM-NAP1 with a membrane cut-off of 50 kDa, two fractions would be generated: the F fraction denoted 50 KF and the C fraction denoted 50 KC.

All of the F and C fractions were then tested for the induction of the cleavage activity of RFD-CD2. All the C fractions induced the cleavage; however, only 50 KF and 100 KF fractions produced cleavage (FIG. 7C). The observation that 3 KF, 10 KF and 30 KF were unable to induce any cleavage of RFD-CD2 shows that the protein target has a molecular weight significantly larger than 30 kDa. However, cleavage activity was observed with both 50 KF and 100 KF, but 100 KF produced much stronger activity than 50 KF.

Another interesting observation is that even 100 KC was still able to induce robust cleavage of RFD-CD2. These results show that the molecular weight range of the DNAzyme-activating target (or targets) is quite broad: it is surely bigger than 30 kDa but it can also be bigger than 100 kDa.

The data show that (1) the target (or targets) is proteinaceous in nature; and (2) RFD-CD2 can have recruited a single protein binding partner, which could be present in CEM-NAP1 in multiple forms, including (1) a full-length form and a partially degraded but still active form; or (2) a full-length form and a complex form with another protein or other proteins. Alternatively, RFD-CD2 can have recruited two or more protein binding partners with different molecular weights.

Species specificity and strain selectivity of RFD-CD2. The recognition specificity of RFD-CD2 was next investigated using CEM samples prepared from nine different bacteria species: three gram-positive bacteria and six gram-negative bacteria. The reaction was conducted in RB2 at 37° C. for 4 hours. No detectable cleavage was observed in non-targeted bacteria (FIG. 8A). The result clearly shows that RFD-CD2 is highly specific towards *C. difficile.*

The selectivity of RFD-CD2 towards diverse strains of *C. difficile* was also assessed. Nine different strains purchased from ATCC (American Type Culture Collection) and CCUG (Culture Collection University of Gothenburg) were tested. These strains include BAA-1870 (NAP1), BAA-1803 (also NAP1 but with a different toxin type, see Table 3), BAA-1871 (NAP2), BAA-1872 (NAP4), BAA-1875 (NAP7), BAA-1814, 51695, 43594, and CCUG 20309. These strains were selected for their toxigenicity as toxin A and toxin B are the major virulence factors for *C. difficile.*[46-47] All tested strains produced both toxin A and toxin B other than CCUG 20309, which only produced toxin B (Table 3). As $TcdA^{-}TcdB^{+}$ *C. difficile* strain was previously documented for infection outbreaks,[48] including this special strain, it is important to examine the response of RFD-CD2 towards diverse pathogenic *C. difficile* strains. Other tested strains are relevant to historic *C. difficile* outbreaks. For example, NAP1 strain caused an outbreak around the world in early 2000, which was reported to be responsible for 51% CDI cases in the US and 84% in Canada in early 2000.[49,50] NAP2 was another predominant strains across the world,[51-53] while NAP4 was the second most prevalent strain in Canada during 2009-2015.[54] NAP7, a hypervirulent strain associated with severe diarrhea and a high mortality rate, has caused outbreaks in the United Kingdom and the Netherlands.[55-57] Other tested strains have the ribotype that has caused multiple outbreaks around the world.[58-60]

Cleavage activity was detected in all tested *C. difficile* strains, although percent cleavage varied noticeably among these strains (FIG. 8B). CEM-NAP1 (BAA-1870) produced the highest cleavage activity (43%), in agreement with RFD-CD2 being selected positively towards this strain. BAA-1875 (NAP7) induced the second highest activity (31%), followed by BAA-1803 (also NAP1) and BAA-1871 (NAP2) with 22% and 19%, respectively. BAA-1872 (NAP4) and 51695 strain produced the weakest cleavage, as only 1-2% cleavage was observed. Taken together, RFD-CD2 is highly specific for *C. difficile* but is reactive with diverse clinical strains of *C. difficile*, showing it could be further developed as a universal DNAzyme probe for diagnosing CDI.

Detection sensitivity of RFD-CD2 as a fluorescent sensor. The RFD-CD2 was next examined as a fluorescent sensor in four different ways: fluorescence reading and dPAGE-based analysis of reactions of RFD-CD2 with either whole cell culture of NAP1 or CEM-NAP1. The fluorescence assay was conducted by incubating a gradually increased concentration of a target sample with RFD-CD2 and the fluorescence intensity of the reaction was recorded every 15 minutes. The limit of detection (LOD) for this fluorescence assay is defined as 3σ+mean negative control, with a being the standard deviation of the negative control samples. As *C. difficile* whole cells were recovered from patients' fecal samples for culturing detection, both whole cell culture and CEM are interesting target forms to examine for RFD-CD2. The LOD was determined to be $10^4$ CFU/mL towards both target forms (FIG. 9A and FIG. 9B) but CEM-NAP1 induced a higher level of fluorescence intensity than the whole cell culture. This LOD was reached after 1-hour incubation (FIG. 10), however, extending the reaction for three more hours failed to improve the detection sensitivity. The lower cleavage signal with the whole cell culture can be attributed to the presence of cell membrane, a complex biological surface with various surface ligands and proteins, some of which can interact with RFD-CD2 and negatively impact its functionality.

As a detection method comparison, the cleavage reaction mixtures were also analyzed by 10% dPAGE after incubating RFD-CD2 with a target sample for 4 hours at 37° C. The LOD for dPAGE analysis is defined as the lowest concentration of target that was capable of producing an observable cleavage band on gel. An LOD of $10^3$ CFU/mL for whole cell culture and an LOD of $10^2$ CFU/mL for CEM-NAP1 were achieved (FIG. 9C), which was about 10-fold more sensitive than fluorescence assay, respectively. As a comparison, EIA against GDH or EIA against toxin A/B can reach $10^3$ CFU/g (feces).[61] The LOD of PCR assays varies from $10^1$ to $10^4$ CFU/mL (CFU/g).[62-64] Overall, RFD-CD2 based assays displayed very comparable LODs with these two detection methods. The culturing methods, however, can reach an LOD of $10^1$ to $10^2$ CFU/mL depending on the recovery method.[65] To further improve the detection limit, a signal amplifier (e.g., rolling circle amplification, loop-mediated isothermal amplification) or a more sensitive signal transduction mechanism (e.g., electrochemical signal) will be investigated in the future.[66-69]

Identification of functionally important sequence elements of RFD-CD2 via nucleotide truncations. A shorter but active version of RFD-CD2 was then derived by nucleotide truncation as a shorter sequence costs less to synthesize and is simpler for biosensor engineering. The truncation of non-essential nucleotides is expected to have a neutral or even positive effect on the performance of a DNAzyme; however, the removal of functionally important nucleotides will have a significant impact on the catalytic activity.

The activity of a series of shortened sequences of RFD-CD2—with a block of nucleotides removed from the 3' end, from the 5' or internally—was tested. Each truncated sequence was assessed for its relative cleavage activity at 4-hour incubation with CEM-NAP1 at 37° C., with the percent cleavage observed for the full-length RFD-CD2 taken as 100. In total, 22 sequences were tested in this experiment and the data is provide in Table 4. The normalized activities of these truncation variants vary significantly, ranging from 3.4 for RFD-CD2-TV14 to 106.4 for RFD-CD2-TV22 (Table 4). Most importantly, the results obtained with these truncation variants clearly identified two sequence elements as functionally important, which are denoted as "important sequence element 1" (covering $T_{41}$ to $C_{71}$) and "important sequence element 2" (covering $G_{81}$ to $G_{108}$) in FIG. 11A. The best truncated sequence is RFD-CD2-TV22, which exhibited a normalized activity of 106.4 even though it contains 31 fewer nucleotides in comparison to RFD-CD2 (FIG. 11A), with 10, 9 and 12 nucleotides truncated from the 5' end, internally, and from the 3' end, respectively (FIG. 11A).

Examination of sequence conservation of RFD-CD2 via reselection. Next, reselection was performed to identify functionally important nucleotides. The reselection experiment used a partially randomized library based on the original sequence of RFD-CD2 with a degeneracy of 0.24 at each of the original random-sequence positions (i.e., the $A_{51}$-$A_{110}$ element shown in FIG. 1B). Specifically, during the chemical synthesis of the DNA pool for reselection, a mixture of amidites was used to introduce mutations at each of these nucleotide positions, with the original (wild-type) nucleotide set at 76% and each of remaining three nucleotides set at 8%. This same mutation strategy has been successfully used in previous studies to isolate various mutant DNAzymes.[70-72] The sequences of all the DNA molecules used for reselection are provided in Table 5. Note that the sequence of the reverse primer binding site (shown in FIG. 6B as italic letter at the 3'-end of the library sequence) was changed to avoid potential contamination by the DNAzymes from the original selection. Upon completion of the reselection experiment and sequencing, functionally important nucleotides are expected to be highly conserved while non-essential nucleotides would tolerate mutations.[71,74] Six rounds of selection were carried out. The detailed parameters for the reselection experiment are provided in Table 6 and the progress of reselection, measured as percent cleavage of each round of selection is summarized in FIG. 6.

Concentrated CEM-NAP1 was used as the positive-selection target in each round. The selection pressure was increased during the reselection process by reducing the concentrations of both the DNA pool and CEM-NAP1 as well as reducing the incubation time—these measures were implemented in order to isolate the most active sequence. Specifically, for the first three rounds, 23× concentrated CEM-NAP1 was used as the positive target, the reaction time was set at 30 minutes, while the concentration of the DNA pool was reduced from 1 μM in round 1 to 0.5 μM in round 2 and then to 0.25 μM in round 3.

By round 3, strong cleavage (16.2%) was observed (FIG. 12). For rounds 4-6, the concentration of CEM-NAP1 was reduced to 12× in round 4 and 4× in rounds 5 and 6; the reaction time was reduced to 15 minutes in round 4, 5 minutes in round 5 and 1 minute in round 6; the concentration of the DNA pool was reduced to 0.2 μM in round 4 to 0.1 μM in rounds 5 and 6. 13.8%, 5% and 0.4% cleavage was observed with the DNA pools at rounds 4, 5 and 6, respectively (FIG. 12). The low-level cleavage in round 6 suggested that the pool reached its catalytic limit.

Counter-selection steps were conducted in round 4 (with SB; reaction time: 18 hours) and round 6 (with CMB; reaction time: 24 hours), which were intended to remove self-cleaving RFDs and RFDs that could be activated by background molecules in the culture media. The cleavage was not observed in SB only in round 4 and the cleavage level observed with CMB in round 6 was small (2.1%) even with an incubation times of 24 hours, showing that the DNA pool was dominated by RFDs responsive to CEM-NAP1.

Deep sequencing was performed with the round-6 cleavage product. Nucleotide mutation and conservation pattern observed with the top 450 sequences was organized into "variation index (VI)" chart shown in FIG. 11B. VI, used in previous publications,[75] is a measurement of mutation at each nucleotide portion from a DNAzyme reselection experiment. A VI for each nucleotide in RDF-CD2 was calculated by dividing the experimentally observed mutation rate by 0.24 (the mutation rate of the starting library). A VI of 0 means that the nucleotide at this position is absolutely conserved in all of the mutant DNAzymes from the reselection and is highly important to the function of RFD-CD2. A VI of 1 means that mutation rate at this position is equal to that in the starting library and thus mutations at this position is tolerated, signifying that the original nucleotide at this location is not functionally important. A VI greater than 1 can be interpreted as the positions are non-essential or one or more mutated nucleotides are preferred over the original nucleotide.[75]

The first highly conserved sequence element from reselection overlaps well with the important sequence element identified by the sequence truncation experiment. Specifically, the important sequence element 1 established by the truncation analysis covers $T_{41}$-$C_{71}$, while the conserved sequence element 1 from reselection covers $A_{51}$-$C_{71}$. However, $T_{41}$-$C_{50}$ is part of the forward primer binding site for reselection and thus was not subjected to mutagenesis.

The important sequence element 2 by the truncation analysis covers $G_{81}$-$C_{108}$, which only partially overlaps with $G_{91}$-$G_{108}$, the conserved sequence element 2 from reselection. In other words, the truncation experiment identified $G_{81}$-$G_{90}$ as "functionally important" while the reselection showed a portion the nucleotides in this region can tolerate mutations. The apparent contradictory findings will be rationalized in the next section where the secondary structure of RFD-CD2 is elucidated: it turns out that $G_{81}$-$G_{90}$ merely acts as a structural linker and the identities of the nucleotides in this region are unimportant.

Elucidation of secondary structure of RFD-CD2. To further investigate the apparent contradictory findings in functionally important sequence elements, the secondary structure of RFD-CD2 was elucidated. A proposed secondary structure model of RFD-CD2 is provided in FIG. 13B, which comprises two pairing elements P1 and P2, two pseudoknot loops PL12 and PL21, and two single-stranded elements SS1 and SS2.

P1 involves the pairing of the $G_{12}$-$C_{21}$ element (10 nucleotides) within the substrate domain with the $G_{62}$-$C_{71}$ element (10 nucleotides) within the random-sequence domain (also indicated by the grey lines in FIG. 13A). The existence of P1 explains the high-level conservation of the $G_{62}$-$C_{71}$ element: because the $G_{12}$-$C_{21}$ element is located within the substrate domain and remained unmutagenized during reselection, the $G_{62}$-$C_{71}$ element would have to remain conserved in order to allow the formation of the P1 element.

P2 involves the pairing of the $A_{57}$-$A_{61}$ element (5 nucleotides) with the $T_{97}$-$T_{101}$ element (5 nucleotides), both of which are located within the random-sequence domain (indicated by black lines in FIG. 13A) and are subjected to mutations. Indeed many complementary base covariations were observed in the selected mutants of RFD-CD2 (FIG. 13D). There were only 17 sequences with complementary base covariations in P2 from the round-3 cleavage pool, but this number increased to 30 in round 6. This finding shows that sequences with base-pairing at these sequence elements were enriched by reselection.

Three RFD-CD2 mutants were also designed and activities tested to further verify the importance of P2 to the DNAzyme function (FIG. 13E). Specifically, $A_{59}T_{60}$ was mutated into $C_{59}G_{60}$ to disrupt the formation of the two middle Watson-Crick base pairs in P2, and the relative activity of the resultant mutant M1 was sharply reduced from 100 to 9 (the sequences of all DNAzyme mutants tested in this section are provided Table 7 along with their relative activities). However, when $A_{98}T_{99}$ were mutated to $C_{98}G_{99}$, which restored the Watson-Crick pairing interactions at these locations, the relative activity of the new mutant M2 jumped from 9 to 80 (FIG. 13E). Analysis of mutations observed at position 60 (originally $T_{60}$) and position 98 (originally $A_{98}$) led to the discovery of $A_{60}$-$T_{98}$ being a frequent complementary base covariation. This new RFD-CD2 variant, which is listed as M3 in FIG. 13E, indeed showed slightly enhanced catalytic activity (relative activity is 103).

The proposed secondary structure of RFD-CD2 was also consistent with nucleotide truncation data. Specifically, the minimized but fully active sequence RFD-CD2-TV22 maintained the key pseudoknot structural arrangement, as shown in FIG. 13C. Any nucleotide truncations that would weaken the P1 and P2 pairing interactions were observed to cause significant activity reduction (Table 4). The key differences between the structures of RFD-CD2 and RFD-CD2-TV22 are the size reduction of PL12 (removal of 10 nucleotides), PL21 (removal of 9 nucleotides) and SS2 (removal of 12 nucleotides); these removed nucleotides are located either in the constant-sequence regions or in the non-conserved sequence elements in the random-sequence domain.

The truncation data given in Table 4 indicates the $G_{81}$-$G_{90}$ element cannot be truncated, and yet the reselection data shows these ten nucleotides are highly mutated (FIG. 11B). A possible explanation is that this sequence element merely functions as a linking element to assist structural formation of the DNAzyme and the nucleotide identities within this linker are not important. To assess this, 6 mutants of RFD-CD2-TV22 were created, wherein this 10-nucleotide linker was changed to a linker containing 10 (M4), 9 (M5), 8 (M6), 7 (M7), 6 (M8) and 5 (M9) T residues (FIG. 13F; note that the $G_{81}$-$G_{90}$ element in RFD-CD2 becomes the $G_{62}$-$G_{71}$ element in RFD-CD2-TV22). Indeed, all of the non-T nucleotides within this sequence element can be altered into T nucleotides without impacting the catalytic activity. The DNAzyme needs to possess a linker at this location with a size of at least 9 nucleotides to retain full activity (FIG. 13F), based on the observation M4 (with a 10T linker) and M5 (with a 9T linker) mutants of RFD-CD2-TV22 retained full activity while M6, M7, M8 and M9 mutants produced progressively reduced activities when the linker was reduced to 8T, 7T, 6T and 5T, respectively (FIG. 13F). Thus, it turns out that $G_{81}$-$G_{90}$ merely acts as a structural linker and the identities of the nucleotides in this region are unimportant.

Finally, based on the reselection data and mutagenesis analysis, a new variant of RFD-CD2 was designed, termed RFD-CD2M10 hereinafter, which incorporates the 9T linker and the $A_{50}$-$T_{79}$ base pair. RFD-CD2-M10 has the smallest sequence but showed highest activity: it contains 88 nucleotides and had a relative activity of 121. Moreover, the specificity of RFD-CD2-M10 was minimally impacted by the truncation and mutation, as RFD-CD2-M10 still exhibited high specificity towards *C. difficile* species and still responded to multiple clinical strains of *C. difficile* (FIG. 14).

CONCLUSION

In summary, an RNA-cleaving fluorogenic DNAzyme named RFD-CD2 that is responsive to diverse *C. difficile* strains was developed. Under improved reaction conditions and a saturating target concentration, RFD-CD2 exhibited a catalytic rate constant ($k_{obs}$) of 0.09 $min^{1}$ and thus qualifies as one of the most active bacteria-responding RFD reported to date. The target molecule for RFD-CD2 is a heat-sensitive, proteinaceous molecule (or molecules) with a molecular weight greater than 30 kDa. Comprehensive sequence and structure characterization revealed a pseudoknot in the structure of RFD-CD2 and a significantly minimized but more active sequence RFD-CD2-M10 (88 nt) was established. RFD-CD2 not only exhibited high species-specificity towards *C. difficile* but is also reactive towards diverse clinically relevant *C. difficile* strains investigated in this disclosure. This specificity pattern renders RFD-CD2 a potential universal sensing probe for CDI diagnosis. As a fluorescent sensor, RFD-CD2 is able to achieve an LOD of 100 CFU/mL with 4-hour incubation using dPAGE analysis and an LOD of $10^4$ CFU/mL within 1-hour incubation using a fluorimeter. Note that the *C. difficile* count in CDI clinical feces was at $10^6$ CFU/g (feces wet weight);[76] if 1 g of wet fecal sample is dissolved in 1 mL solution, the concentration of *C. difficile* in the test sample would be $10^6$ CFU/mL. Given the LOD of RFD-CD2 from 1-hour assay using a fluorimeter was $10^4$ CFU/mL, the DNAzyme assay is sensitive enough to identify CDI.

While the present disclosure has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

Tables

TABLE 1

Sequences used for in vitro selection.

| SEQ ID NO | Name | Sequence (5' to 3') |
|---|---|---|
| 1 | QRF30 (substrate, 30 nt) | CATCAGACTC CGQRFAACCT CACTACCAAG<br>F: fluorescein-dT; Q: dabcyl-dT; R: adenosine ribonucleotide |
| 2 | LT1 (ligation template, 35 nt) | GGTGTAGGGA GTTTAGGTTG CTTGGTAGTG AGGTT |
| 3 | FP1 (forward primer, 20 nt) | CAACCTAAAC TCCCTACACC |
| 4 | RP1 (reverse primer 1, 20 nt) | CGACATCTGC TTCCACATCA |
| 4 + 5 | RP2 (reverse primer 2, 40 nt) | AAAAAAAAAA AAAAAAAAAA L CGACATCTGC TTCCACATCA<br>(SEQ ID NO: 4 - CGACATCTGC TTCCACATCA)<br>(SEQ ID NO: 5 - AAAAAAAAAA AAAAAAAAAA)<br>L: Non-amplifiable triethylene glycol linker<br>The 5' deoxycytidine in SEQ ID NO: 4 is attached through the non-amplifiable triethylene glycol linker to the 3' deoxyadenosine in SEQ ID NO: 5 |
| 6 | Anti-RP1 (antisense reverse primer 1, 20 nt) | TGATGTGGAA GCAGATGTCG |
| 6 + 7 | Anti-RP2 (antisense reverse primer 1, 40 nt) | TGATGTGGAA GCAGATGTCG L TTTTTTTTTT TTTTTTTTTT<br>(SEQ ID NO: 6 - TGATGTGGAA GCAGATGTCG)<br>(SEQ ID NO: 7 - TTTTTTTTTT TTTTTTTTTT)<br>L: Non-amplifiable triethylene glycol linker<br>The 5' thymidine in SEQ ID NO: 7 is attached through the non-amplifiable triethylene glycol linker to the 3' deoxyguanosine in SEQ ID NO: 6 |
| 54 | DL1 | CATCAGACTC CGQRFAACCT CACTACCAAG NNNNNNNNNN NNNNNNNNNN NNNNNNNNNN NNNNNNNNNN NNNNNNNNNN TGATGTGGAA GCAGATGTCG<br>F: fluorescein-dT; Q: dabcyl-dT; R: adenosine ribonucleotide; N = A, C, G, or T |

TABLE 2

Top candidate DNAzymes from the round-7 pool and their corresponding sequences from the random-sequence domain.

| SEQ ID NO | Class/Notes | Sequence (5'-3') |
|---|---|---|
| 10 | 1 | CAACCTAAACTCCCTACACCCCAAACTGGTTATGAAGG TATGGGTTATATGAGTCAAGAATGAGATACTGTGATGT GGAAGCAGATGTCG |
| 11 | 2 | CAACCTAAACTCCCTACACCACATTAAGATAGAGGTTA TACTGGGTCACAGATAGTCTAGGTAGGTTATCTGATGT GGAAGCAGATGTCG |
| 12 | 3 | CAACCTAAACTCCCTACACCGTTCTTAGTATATAGAATT ATTTAGTTAATGAGTTATCGGACGACAAATGATGTGGA AGCAGATGTCG |
| 13 | 4 | CAACCTAAACTCCCTACACCCCTAAGATAAATGGATCC TAGACCCACAGTGATGATTAACGGCGATATTTGATGTG GAAGCAGATGTCG |
| 14 | 5 | CAACCTAAACTCCCTACACCGTTCTCAGAACAATCAAT TCAAAATTTTAGTAAGGTTAACGGCTACATATGATGTG GAAGCAGATGTCG |
| 55 | (random-sequence domain of SEQ ID NO: 10) | CCAAACTGGTTATGAAGGTATGGGTTATATGAGTCAAG AATGAGATACTG |
| 56 | (random-sequence domain of SEQ ID NO: 11) | ACATTAAGATAGAGGTTATACTGGGTCACAGATAGTCT AGGTAGGTTATC |
| 57 | (random-sequence domain of SEQ ID NO: 12) | GTTCTTAGTATATAGAATTATTTAGTTAATGAGTTATCG GACGACAAA |
| 58 | (random-sequence domain of SEQ ID NO: 13) | CCTAAGATAAATGGATCCTAGACCCACAGTGATGATTA ACGGCGATATT |
| 59 | (random-sequence domain of SEQ ID NO: 14) | GTTCTCAGAACAATCAATTCAAAATTTTAGTAAGGTTA ACGGCTACATA |

TABLE 3

Strain information summary of tested *C. difficile* strains. Information was collected from ATCC and CCUG website.

| Strain name | PFGE type | Ribotype | Toxin-type | Toxigenic | tcdA | tcdB |
|---|---|---|---|---|---|---|
| BAA-1870 | NAP1 | 027 | lllb | yes | + | + |
| BAA-1803 | NAP1 | 027 | IIIc | yes | + | + |
| BAA-1871 | NAP2 | 001 | 0 | yes | + | + |
| BAA-1872 | NAP4 | 207 | 0 | yes | + | + |
| BAA-1875 | NAP7 | 078 | V | yes | + | + |
| BAA-1814 | N/A | 251 | XXII | yes | + | + |
| 51695 | N/A | 001 | 0 | yes | + | + |
| 43594 | N/A | 005 | 0 | yes | + | + |
| CCUG 20309 | N/A | N/A | N/A | yes | − | + |

PFGE: Pulsed Field Gel Electrophoresis Typing.
tcdA: the toxin A-coding gene in *C. difficile*.
tcdB: the toxin B-coding gene in *C. difficile*.

TABLE 4

Truncated sequences information and normalized activity. Each dash represented one truncated nucleotide. NCP represents "normalized cleavage percentage", which was calculated by dividing the cleavage percentage of a truncated sequence to that of RFD-CD2. Each sequence was tested in triplicate, NCP value represents the NCP mean plus standard deviation of three trials.

| SEQ ID NO | Name | Sequence (5' to 3') | NCP |
|---|---|---|---|
| 11 | RFD-CD2 | CAACCTAAACTCCCTACACCACATTAAG ATAGAGGTTATACTGGGTCACAGATAGT CTAGGTAGGTTATCTGATGTGGAAGCAG ATGTCG | 100 |
| 15 | RFD-CD2-TV1 | CAACCTAAACTCCCTACACCACATTAAG ATAGAGGTTATACTGGGTCACAGATAGT CTAGGTAGGTTATCTGATGTGGAAGCAG A----- | 83.8 ± 5.6 |
| 16 | RFD-CD2-TV2 | CAACCTAAACTCCCTACACCACATTAAG ATAGAGGTTATACTGGGTCACAGATAGT CTAGGTAGGTTATCTGATGTGGAA---- ------ | 68.9 ± 3.8 |
| 17 | RFD-CD2-TV3 | CAACCTAAACTCCCTACACCACATTAAG ATAGAGGTTATACTGGGTCACAGATAGT CTAGGTAGGTTATCTGATG-------------- | 18.2 ± 3.0 |
| 18 | RFD-CD2-TV4 | CAACCTAAACTCCCTACACCACATTAAG ATAGAGGTTATACTGGGTCACAGATAGT CTAGGTAGGTTATC------------------- | 8.3 ± 1.0 |
| 19 | RFD-CD2-TV5 | ----- TAAACTCCCTACACCACATTAAGATAGA GGTTATACTGGGTCACAGATAGTCTAGG TAGGTTATCTGATGTGGAA---------- | 74.5 ± 5.3 |
| 20 | RFD-CD2-TV6 | ---------- TCCCTACACCACATTAAGATAGAGG TTATACTGGGTCACAGATAGTCTAGGTA GGTTATCTGATGTGGAA---------- | 41.3 ± 4.1 |
| 21 | RFD-CD2-TV7 | --------------- ACACCACATTAAGATAGAGGTTA TACTGGGTCACAGATAGTCTAGGTAGGT TATCTGATGTGGAA---------- | 36.3 ± 2.7 |
| 22 | RFD-CD2-TV8 | -------------------- ACATTAAGATAGAGGTTATA CTGGGTCACAGATAGTCTAGGTAGGTTA TCTGATGTGGAA---------- | 5.0 ± 0.6 |
| 23 | RFD-CD2-TV9 | ---------- TCCCTACACCACATTAAGATAGAGG TTATACTGGGTCACAGATAGTCTAGGTA GGTTATCTGATGTGG------------ | 67.0 ± 3.5 |
| 24 | RFD-CD2-TV10 | ----------TCCCT----- ACATTAAGATAGAGGTTA TACTGGGTCACAGATAGTCTAGGTAGGT TATCTGATGTGG----------- | 7.6 ± 0.5 |
| 25 | RFD-CD2-TV11 | ----------TCCCTACACC----- AAGATAGAGGTTA TACTGGGTCACAGATAGTCTAGGTAGGT TATCTGATGTGG- | 5.2 ± 0.5 |
| 26 | RFD-CD2-TV12 | ----------TCCCTACACCACATT----- AGAGGTTA TACTGGGTCACAGATAGTCTAGGTAGGT TATCTGATGTGG----------- | 5.0 ± 0.7 |
| 27 | RFD-CD2-TV13 | TCCCTACACCACATTAAGAT----- TTA TACTGGGTCACAGATAGTCTAGGTAGGT TATCTGATGTGG----------- | 3.6 ± 0.8 |
| 28 | RFD-CD2-TV14 | ---------- TCCCTACACCACATTAAGATAGAGG----- CTGGGTCACAGATAGTCTAGGTAGGTTA TCTGATGTGG----------- | 3.4 ± 0.9 |

TABLE 4-continued

Truncated sequences information and normalized activity. Each dash represented one truncated nucleotide. NCP represents "normalized cleavage percentage", which was calculated by dividing the cleavage percentage of a truncated sequence to that of RFD-CD2. Each sequence was tested in triplicate, NCP value represents the NCP mean plus standard deviation of three trials.

| SEQ ID NO | Name | Sequence (5' to 3') | NCP |
|---|---|---|---|
| 29 | RFD-CD2-TV15 | ----------<br>TCCCTACACCACATTAAGATAGAGG<br>TTATA-----<br>TCACAGATAGTCTAGGTAGGTTA<br>TCTGATGTGG------------ | 43.6 ± 4.8 |
| 30 | RFD-CD2-TV16 | ----------<br>TCCCTACACCACATTAAGATAGAGG<br>TTATACTGGG----<br>GATAGTCTAGGTAGGTTA<br>TCTGATGTGG------------ | 74.8 ± 2.3 |
| 31 | RFD-CD2-TV17 | ----------<br>TCCCTACACCACATTAAGATAGAGG<br>TTATACTGGGTCACA-----<br>TCTAGGTAGGTTA<br>TCTGATGTGG------------ | 39.7 ± 1.3 |
| 32 | RFD-CD2-TV18 | ----------<br>TCCCTACACCACATTAAGATAGAGG<br>TTATACTGGGTCACAGATAG-----<br>GTAGGTTA<br>TCTGATGTGG------------ | 64.1 ± 1.2 |
| 33 | RFD-CD2-TV19 | ----------<br>TCCCTACACCACATTAAGATAGAGG<br>TTATACTGGGTCACAGATAGTCTAG-----<br>TTA<br>TCTGATGTGG------------ | 7.4 ± 0.4 |
| 34 | RFD-CD2-TV20 | ----------<br>TCCCTACACCACATTAAGATAGAGG<br>TTATACTGGGTCACAGATAGTCTAGGTA<br>GG-----TGATGTGG------------ | 5.2 ± 0.7 |
| 35 | RFD-CD2-TV21 | ----------<br>TCCCTACACCACATTAAGATAGAGG<br>TTATACTGGGTCACAGATAGTCTAGGTA<br>GGTTATC-----TGG------------ | 7.0 ± 0.5 |
| 36 | RFD-CD2-TV22 | ----------<br>TCCCTACACCACATTAAGATAGAGG<br>TTATAC---------<br>GATAGTCTAGGTAGGTTATC<br>TGATGTGG------------ | 106.4 ± 6.3 |

TABLE 5

Sequences used in the reselection experiment. The sequence of RFD-CD2 (SEQ ID NO: 11) was chemically synthesized to contain two primer binding regions (bold nucleotides) and a central, partially randomized region where each nucleotide position was given a degeneracy of 0.24 for (76% for wild-type nucleotide and 8% for each of the three remaining nucleotides).

| SEQ ID NO | Name | Sequence (5' to 3') |
|---|---|---|
| 1 | QRF30 (substrate, 30 nt) | CATCAGACTC CGQRFAACCT<br>CACTACCAAG<br>F: fluorescein-dT; Q: dabcyl-dT; R: adenosine ribonucleotide |
| 76 | Base sequence of QRF30 (substrate, 30 nt) | CATCAGACTC CGTRTAACCT<br>CACTACCAAG<br>R: adenosine ribonucleotide |
| 37 | DL2 (library, 100 nt) | **CAACCTAAACTCCCTACACC**ACATTAAGA<br>TAGAGGTTATACTGGGTCACAGATAGTCTA<br>GGTAGGTTATCTGATGTGGAA**TCTTGTCAT**<br>**CGGAGGCTTAG** |

TABLE 5-continued

Sequences used in the reselection experiment. The sequence of RFD-CD2 (SEQ ID NO: 11) was chemically synthesized to contain two primer binding regions (bold nucleotides) and a central, partially randomized region where each nucleotide position was given a degeneracy of 0.24 for (76% for wild-type nucleotide and 8% for each of the three remaining nucleotides).

| SEQ ID NO | Name | Sequence (5' to 3') |
|---|---|---|
| 2 | LT1 (ligation template, 35 nt) | GGTGTAGGGA GTTTAGGTTG CTTGGTAGTG AGGTT |
| 3 | FP1 (forward primer 1, 20 nt) | CAACCTAAAC TCCCTACACC |
| 8 | RP3 (reverse primer 3, 20 nt) | CTAAGCCTCC GATGACAAGA |
| 5 + 8 | RP4 (reverse primer 4, 40 nt) | AAAAAAAAAA AAAAAAAAAA L CTAAGCCTCC GATGACAAGA<br>L: Non-amplifiable triethylene glycol linker<br>(SEQ ID NO: 5 - AAAAAAAAAA AAAAAAAAAA)<br>(SEQ ID NO: 8 - CTAAGCCTCC GATGACAAGA)<br>The 5' deoxycytidine in SEQ ID NO: 8 is attached through the non-amplifiable triethylene glycol linker to the 3' deoxy adenosine in SEQ ID NO: 5 |
| 9 | Anti-RP3 (antisense reverse primer 3, 20 nt) | GATTCGGAGG CTACTGTTCT |
| 7 + 9 | Anti-RP4 (antisense reverse primer 4, 40 nt) | GATTCGGAGG CTACTGTTCT L TTTTTTTTTT TTTTTTTTTT<br>L: Non-amplifiable triethylene glycol linker<br>(SEQ ID NO: 7 - TTTTTTTTTT TTTTTTTTTT)<br>(SEQ ID NO: 9 - GATTCGGAGG CTACTGTTCT)<br>The 5' thymidine in SEQ ID NO: 7 is attached through the non-amplifiable triethylene glycol linker to the 3' thymidine in SEQ ID NO: 9 |

TABLE 6

Parameters for the reselection experiment with RFD-CD2 (SEQ ID NO. 11). CMB: cooked meat broth, the culture media for NAP1. CEM used in positive selection was NAP1-CEM, the number before CEM indicated the concentration times.

| | Target and incubation time | | Library concentration (μM) | |
|---|---|---|---|---|
| Round | Counter selection | Positive selection | Counter selection | Positive selection |
| 1 | — | 23 × CEM (30 minutes) | — | 1 |
| 2 | — | 23 × CEM (30 minutes) | — | 0.5 |
| 3 | — | 23 × CEM (30 minutes) | — | 0.25 |
| 4 | Selection buffer (18 hours) | 12 × CEM (15 minutes) | 0.4 | 0.2 |
| 5 | — | 4 × CEM (5 minutes) | — | 0.1 |
| 6 | CMB (24 hours) | 4 × CEM (1 minute) | 2.8 | 0.1 |

TABLE 7

Mutated sequences information and normalized activity. Each dash represented one truncated nucleotide. NCP represented "normalized cleavage percentage", which was calculated by dividing the cleavage percentage to that of RFD-CD2 (SEQ ID NO: 11). Each sequence was tested in triplicate, NCP value represents the mean and standard deviation of three trials.

| SEQ ID NO | Name | Sequence (5' to 3') | NCP |
|---|---|---|---|
| 11 | RFD-CD2 | CAACCTAAACTCCCTACACCACATTAAGATAG AGGTTATACTGGGTCACAGATAGTCTAGGTAG GTTATCTGATGTGGAAGCAGATGTCG | 100 |

TABLE 7-continued

Mutated sequences information and normalized activity. Each dash represented one truncated nucleotide. NCP represented "normalized cleavage percentage", which was calculated by dividing the cleavage percentage to that of RFD-CD2 (SEQ ID NO: 11). Each sequence was tested in triplicate, NCP value represents the mean and standard deviation of three trials.

| SEQ ID NO | Name | Sequence (5' to 3') | NCP |
|---|---|---|---|
| 38 | RFD-CD2-M1 | CAACCTAAACTCCCTACACCACATTAAGCGAG<br>AGGTTATACTGGGTCACAGATAGTCTAGGTAG<br>GTTATCTGATGTGGAAGCAGATGTCG | 9.2 ± 5.3 |
| 39 | RFD-CD2-M2 | CAACCTAAACTCCCTACACCACATTAAGCGAG<br>AGGTTATACTGGGTCACAGATAGTCTAGGTAG<br>GTTCGCTGATGTGGAAGCAGATGTCG | 79.6 ± 4.8 |
| 40 | RFD-CD2-M3 | CAACCTAAACTCCCTACACCACATTAAGAAAG<br>AGGTTATACTGGGTCACAGATAGTCTAGGTAG<br>GTTTTCTGATGTGGAAGCAGATGTCG | 103.0 ± 12.6 |
| 41 | RFD-CD2-M4 | ----------TCCCTACACCACATTAAGATAGAGGTT<br>ATAC---------TTTTTTTTTGTAGGTTATCTGATG<br>TGG------------ | 103.9 ± 3.0 |
| 42 | RFD-CD2-M5 | ----------TCCCTACACCACATTAAGATAGAGGTT<br>ATAC----------TTTTTTTTGTAGGTTATCTGATG<br>TGG------------ | 109.9 ± 7.3 |
| 43 | RFD-CD2-M6 | ----------TCCCTACACCACATTAAGATAGAGGTT<br>ATAC-----------TTTTTTTGTAGGTTATCTGATGT<br>GG------------ | 75.9 ± 5.9 |
| 44 | RFD-CD2-M7 | ----------TCCCTACACCACATTAAGATAGAGGTT<br>ATAC------------TTTTTTGTAGGTTATCTGATGT<br>GG------------ | 33.4 ± 2.4 |
| 45 | RFD-CD2-M8 | ----------TCCCTACACCACATTAAGATAGAGGTT<br>ATAC-------------TTTTTGTAGGTTATCTGATGTG<br>G----------- | 13.2 ± 0.9 |
| 46 | RFD-CD2-M9 | ----------TCCCTACACCACATTAAGATAGAGGTT<br>ATAC--------------TTTTGTAGGTTATCTGATGTG<br>G------------ | 7.3 ± 1.0 |
| 47 | RFD-CD2-M10 | ----------TCCCTACACCACATTAAGAAAGAGGTT<br>ATAC----------TTTTTTTTGTAGGTTTTCTGATGT<br>GG------------ | 120.6 ± 7.1 |

TABLE 8

Counter-selection and positive-selection conditions - SB: selection buffer; CMB: cooked meat broth media.

| | R1 | R2-3 | R4-7 |
|---|---|---|---|
| Counter selection | SB<br>(3 hours) | CMB<br>(3 hours) | NAP 2, 4, 7<br>CEM (3 hours) |

TABLE 8-continued

Counter-selection and positive-selection conditions - SB: selection buffer; CMB: cooked meat broth media.

| | R1 | R2-3 | R4-7 |
|---|---|---|---|
| Positive selection | NAP 1<br>CEM (3 hours) | NAP 1<br>CEM (3 hours) | NAP 1<br>CEM (1 hour) |

TABLE 9

Full-length catalytic nucleic acid probe sequences with high cleavage activity.

| SEQ ID NO | Name | Sequence (5' to 3') |
|---|---|---|
| 48 | QRF30-RFD-CD2 | CATCAGACTC CGQRFAACCT CACTACCAAG<br>CAACCTAAAC TCCCTACACC ACATTAAGAT<br>AGAGGTTATA CTGGGTCACA GATAGTCTAG<br>GTAGGTTATC TGATGTGGAA GCAGATGTCG |
| 49 | QRF30-RFD-CD-TV22 | CATCAGACTC CGQRFAACCT CACTACCAAG<br>TCCCTACACC ACATTAAGAT AGAGGTTATA<br>CGATAGTCTA GGTAGGTTAT CTGATGTGG |
| 50 | QRF30-RFD-CD2-M3 | CATCAGACTC CGQRFAACCT CACTACCAAG<br>CAACCTAAAC TCCCTACACC ACATTAAGAA |

TABLE 9-continued

Full-length catalytic nucleic acid probe sequences with high cleavage activity.

| SEQ ID NO | Name | Sequence (5' to 3') |
|---|---|---|
| | | AGAGGTTATA CTGGGTCACA GATAGTCTAG GTAGGTTTTC TGATGTGGAA GCAGATGTCG |
| 51 | QRF30-RFD-CD2-M4 | CATCAGACTC CGQRFAACCT CACTACCAAG TCCCTACACC ACATTAAGAT AGAGGTTATA CTTTTTTTTT TGTAGGTTAT CTGATGTGG |
| 52 | QRF30-RFD-CD2-M5 | CATCAGACTC CGQRFAACCT CACTACCAAG TCCCTACACC ACATTAAGAT AGAGGTTATA CTTTTTTTTT GTAGGTTATC TGATGTGG |
| 53 | QRF30-RFD-CD2-M10 | CATCAGACTC CGQRFAACCT CACTACCAAG TCCCTACACC ACATTAAGAA AGAGGTTATA CTTTTTTTTT GTAGGTTTTC TGATGTGG |

TABLE 10

Additional Sequences of the Disclosure.

| SEQ ID NO | Name | Sequence (5' to 3') |
|---|---|---|
| 60 | Partially randomized region for reselection shown in FIG. 13D | ACATTAAGAT AGAGGTTATA CTGGGTCACA GATAGTCTAG GTAGGTTATC TGATGTGGAA |
| 61 | Partially randomized region for reselection shown in FIG. 13D | ACATTAAGAA AGAGGTTATA CGGAGTGACT GATAGTCAAG GTAGGTTTTC TGATGTGGA |
| 62 | Partially randomized region for reselection shown in FIG. 13D | ACATTAAGAG AGAGGTTATA CTGGGTTACA GATAGTCTAG GTAGGTTCTC TGATTTGTAA |
| 63 | Partially randomized region for reselection shown in FIG. 13D | ACATTAAGAT GGAGGTTATA CTGGGTCACA GATAATGAAG GTAGGTCATC TGATGTGGAC |
| 64 | Partially randomized region for reselection shown in FIG. 13D | CCATTAAGAA AGAGGTTATA CTGGGTCACA TATAGTCTAG GTAGGTTTTC TGATGTGGTA |
| 65 | Partially randomized region for reselection shown in FIG. 13D | ACATTAAGAT TGAGGTTATA CTGGGTCAAA GATAAACTAG GTAGGTAATC TGATGTGGAA |
| 66 | Partially randomized region for reselection shown in FIG. 13D | ACATTACGAT AGAGGTTATA CTGGGTCACA CATAGCGTAG GTAGGGTATC GGATGTGGAA |
| 67 | Partially randomized region for reselection shown in FIG. 13D | ACATTAAGAT GGAGGTTATA CTCGGTCACT GATAGTCTCG GTAGGTCTTC TGATGTGGAA |
| 68 | Partially randomized region for reselection shown in FIG. 13D | ACATTAAGAT TGAGGTTATA CTAGGTCACA GATAGTCTAG GTAGGTAATC TGTTGTGGAA |
| 69 | RFD-CD2TV22 shown in FIG. 3F | GATAGTCTAG |
| 70 | Base sequence of QRF30-RFD-CD2 | CATCAGACTC CGTRTAACCT CACTACCAAG CAACCTAAAC TCCCTACACC ACATTAAGAT AGAGGTTATA CTGGGTCACA GATAGTCTAG GTAGGTTATC TGATGTGGAA GCAGATGTCG |
| 71 | Base sequence of QRF30-RFD-CD-TV22 | CATCAGACTC CGTRTAACCT CACTACCAAG TCCCTACACC ACATTAAGAT AGAGGTTATA CGATAGTCTA GGTAGGTTAT CTGATGTGG |

TABLE 10-continued

Additional Sequences of the Disclosure.

| SEQ ID NO | Name | Sequence (5' to 3') |
|---|---|---|
| 72 | Base sequence of QRF30-RFD-CD2-M3 | CATCAGACTC CGTRTAACCT CACTACCAAG CAACCTAAAC TCCCTACACC ACATTAAGAA AGAGGTTATA CTGGGTCACA GATAGTCTAG GTAGGTTTTC TGATGTGGAA GCAGATGTCG |
| 73 | Base sequence of QRF30-RFD-CD2-M4 | CATCAGACTC CGTRTAACCT CACTACCAAG TCCCTACACC ACATTAAGAT AGAGGTTATA CTTTTTTTTT TGTAGGTTAT CTGATGTGG |
| 74 | Base sequence of QRF30-RFD-CD2-M5 | CATCAGACTC CGTRTAACCT CACTACCAAG TCCCTACACC ACATTAAGAT AGAGGTTATA CTTTTTTTTT GTAGGTTATC TGATGTGG |
| 75 | Base sequence of QRF30-RFD-CD2-M10 | CATCAGACTC CGTRTAACCT CACTACCAAG TCCCTACACC ACATTAAGAA AGAGGTTATA CTTTTTTTTT GTAGGTTTTC TGATGTGG |

CITATIONS

[1] W. K. Smits, D. Lyras, D. B. Lacy, M. H. Wilcox, E. J. Kuijper, *Nat. Rev. Dis. Primer* 2016, 2, 1-20.

[2] P. N. Wiegand, D. Nathwani, M. H. Wilcox, J. Stephens, A. Shelbaya, S. Haider, *J. Hosp. Infect.* 2012, 81, 1-14.

[3] G. K. B. Ong, T. J. Reidy, M. D. Huk, F. R. Lane, *Am. J. Surg.* 2017, 213, 565-571.

[4] D. A. Leffler, J. T. Lamont, *N. Engl. J. Med* 2015, 372, 1539-1548.

[5] J. S. H. Martin, T. M. Monaghan, M. H. Wilcox, *Nat. Rev. Gastroenterol. Hepatol.* 2016, 13, 206-216.

[6] J. Czepiel, M. Dróżdż, H. Pituch, E. J. Kuijper, W. Perucki, A. Mielimonka, S. Goldman, D. Wultańska, A. Garlicki, G. Biesiada, *Eur. J. Clin. Microbiol. Infect. Dis.* 2019, 38, 1211-1221.

[7] F. C. Lessa, Y. Mu, W. M. Bamberg, Z. G. Beldavs, G. K. Dumyati, J. R. Dunn, M. M. Farley, S. M. Holzbauer, J. I. Meek, E. C. Phipps, L. E. Wilson, L. G. Winston, J. A. Cohen, B. M. Limbago, S. K. Fridkin, D. N. Gerding, L. C. McDonald, *N. Engl. J. Med* 2015, 372, 825-834.

[8] Y. Xia, M. Tunis, C. Frenette, K. Katz, K. Amaratunga, S. R. Rose, A. House, C. Quach, *Can. Commun. Dis. Rep.* 2019, 45, 191-211.

[9] J. Czepiel, M. Krutova, A. Mizrahi, N. Khanafer, D. A. Enoch, M. Patyi, A. Deptuła, A. Agodi, X. Nuvials, H. Pituch, M. Wójcik-Bugajska, I. Filipczak-Bryniarska, B. Brzozowski, M. Krzanowski, K. Konturek, M. Fedewicz, M. Michalak, L. Monpierre, P. Vanhems, T. Gouliouris, A. Jurczyszyn, S. Goldman-Mazur, D. Wultańska, E. J. Kuijper, J. Skupień, G. Biesiada, A. Garlicki, *Antibiotics* 2021, 10, 299.

[10] E. Finn, F. L. Andersson, M. Madin-Warburton, *BMC Infect. Dis.* 2021, 21, 456.

[11] Z. Peng, L. Ling, C. W. Stratton, C. Li, C. R. Polage, B. Wu, Y.-W. Tang, *Emerg. Microbes Infect.* 2018, 7, 15.

[12] M. B. F. Jensen, K. E. P. Olsen, X. C. Nielsen, A. M. Hoegh, R. B. Dessau, T. Atlung, J. Engberg, *Eur. J. Clin. Microbiol. Infect. Dis. Off Publ. Eur. Soc. Clin. Microbiol.* 2015, 34, 727-736.

[13] D. A. Solomon, D. A. Milner, *Open Forum Infect. Dis.* 2014, 1, ofu007.

[14] E. Kouhsari, S. Abbasian, M. Sedighi, H. F. Yaseri, S. Nazari, A. Z. Bialvaei, P. Dahim, E. Z. Mirzaei, M. Rahbar, *Rev. Med Microbiol.* 2018, 29, 103-109.

[15] F. Y. Khan, A.-N. Elzouki, *Asian Pac. J. Trop. Med* 2014, 7, S6-S13.

[16] Y. Longtin, S. Trottier, G. Brochu, B. Paquet-Bolduc, C. Garenc, V. Loungnarath, C. Beaulieu, D. Goulet, J. Longtin, *Clin. Infect. Dis.* 2013, 56, 67-73.

[17] M. Liu, Q. Yin, J. D. Brennan, Y. Li, *Biochimie* 2018, 145, 151-157.

[18] M. Liu, Q. Yin, Y. Chang, Q. Zhang, J. D. Brennan, Y. Li, *Angew. Chem. Int. Ed* 2019, 58, 8013-8017.

[19] M. Liu, J. Wang, Y. Chang, Q. Zhang, D. Chang, C. Y. Hui, J. D. Brennan, Y. Li, *Angew. Chem. Int. Ed.* 2020, 59, 7706-7710.

[20] J. Li, J. Gu, H. Zhang, R. Liu, W. Zhang, M. Mohammed-Elsabagh, J. Xia, D. Morrison, S. Zakaria, D. Chang, A. Arrabi, Y. Li, *ACS Appl. Mater. Interfaces* 2021, 13, 9464-9471.

[21] Z. Shen, Z. Wu, D. Chang, W. Zhang, K. Tram, C. Lee, P. Kim, B. J. Salena, Y. Li, *Angew. Chem. Int. Ed Engl.* 2016, 55, 2431-2434.

[22] A. D. Ellington, J. W. Szostak, *Nature* 1990, 346, 818-822.

[23] C. Tuerk, L. Gold, *Science* 1990, 249, 505-10.

[24] S. K. Silverman, *Nucleic Acids Res.* 2005, 33, 6151-6163.

[25] J. Liu, Z. Cao, Y. Lu, *Chem. Rev.* 2009, 109, 1948-1998.

[26] K. Schlosser, Y. Li, *Chem. Biol.* 2009, 16, 311-322.

[27] D. Morrison, M. Rothenbroker, Y. Li, *Small Methods* 2018, 2, 1700319.

[28] E. M. McConnell, I. Cozma, D. Morrison, Y. Li, *Anal. Chem.* 2020, 92, 327-344.

[29] E. M. McConnell, I. Cozma, Q. Mou, J. D. Brennan, Y. Lu, Y. Li, *Chem. Soc. Rev.* 2021, 50, 8954-8994.

[30] R. Liu, F. Zhang, Y. Sang, I. Katouzian, S. M. Jafari, X. Wang, W. Li, J. Wang, Z. Mohammadi, *Trends Food Sci. Technol.* 2022, 123, 355-375.

[31] B. Huo, Y. Hu, Z. Gao, G. Li, *Talanta* 2021, 222, 121565.

[32] D. Chang, S. Zakaria, S. Esmaeili Samani, Y. Chang, C. D. M. Filipe, L. Soleymani, J. D. Brennan, M. Liu, Y. Li, *Acc. Chem. Res.* 2021, 54, 3540-3549.

[33] I. Cozma, E. M. McConnell, J. D. Brennan, Y. Li, *Biosens. Bioelectron.* 2021, 177, 112972.

[34] M. Liu, D. Chang, Y. Li, *Acc. Chem. Res.* 2017, 50, 2273-2283.

[35] S. H. J. Mei, Z. Liu, J. D. Brennan, Y. Li, *J. Am. Chem. Soc.* 2003, 125, 3106-3114.

[36] Z. Liu, S. H. J. Mei, J. D. Brennan, Y. Li, *J. Am. Chem. Soc.* 2003, 125, 7539-7545.
[37] M. M. Ali, S. D. Aguirre, H. Lazim, Y. Li, *Angew. Chem. Int. Ed.* 2011, 50, 3751-3754.
[38] M. M. Ali, M. Wolfe, K. Tram, J. Gu, C. D. M. Filipe, Y. Li, J. D. Brennan, *Angew. Chem. Int. Ed.* 2019, 58, 9907-9911.
[39] M. Rothenbroker, E. M. McConnell, J. Gu, M. L. Urbanus, S. E. Samani, A. W. Ensminger, C. D. M. Filipe, Y. Li, *Angew. Chem.* 2021, 133, 4832-4838.
[40] M. M. Ali, R. Silva, D. White, S. Mohammadi, Y. Li, A. Capretta, J. D. Brennan, *Angew. Chem. Int. Ed.* 2022, 61, e202112346.
[41] M. M. Ali, A. Slepenkin, E. Peterson, W. Zhao, *Chembiochem Eur. J. Chem. Biol.* 2019, 20, 906-910.
[42] R. Schmieder, R. Edwards, *Bioinforma. Oxf. Engl.* 2011, 27, 863-864.
[43] W. Li, A. Godzik, *Bioinforma. Oxf Engl.* 2006, 22, 1658-1659.
[44] Z. Zhang, J. Li, J. Gu, R. Amini, H. D. Stacey, J. C. Ang, D. White, C. D. M. Filipe, K. Mossman, M. S. Miller, B. J. Salena, D. Yamamura, P. Sen, L. Soleymani, J. D. Brennan, Y. Li, *Chem.-Eur. J.* 2022, 28, e202200078.
[45] D. Chang, T. Chang, B. Salena, Y. Li, *Chem Bio Chem* 2020, 21, 464-468.
[46] M. Monot, C. Eckert, A. Lemire, A. Hamiot, T. Dubois, C. Tessier, B. Dumoulard, B. Hamel, A. Petit, V. Lalande, L. Ma, C. Bouchier, F. Barbut, B. Dupuy, *Sci. Rep.* 2015, 5, 15023.
[47] S. P. Borriello, *J. Antimicrob. Chemother.* 1998, 41, 13-19.
[48] D. Drudy, S. Fanning, L. Kyne, *Int. J. Infect. Dis.* 2007, 11, 5-10.
[49] L. C. McDonald, G. E. Killgore, A. Thompson, R. C. Owens, S. V. Kazakova, S. P. Sambol, S. Johnson, D. N. Gerding, *N. Engl. J. Med.* 2005, 353, 2433-2441.
[50] V. G. Loo, L. Poirier, M. A. Miller, M. Oughton, M. D. Libman, S. Michaud, A.-M. Bourgault, T. Nguyen, C. Frenette, M. Kelly, A. Vibien, P. Brassard, S. Fenn, K. Dewar, T. J. Hudson, R. Horn, P. René, Y. Monczak, A. Dascal, *N. Engl. J. Med.* 2005, 353, 2442-2449.
[51] M. Miller, D. Gravel, M. Mulvey, G. Taylor, D. Boyd, A. Simor, M. Gardam, A. McGeer, J. Hutchinson, D. Moore, S. Kelly, *Clin. Infect. Dis.* 2010, 50, 194-201.
[52] A. Jiménez, R. Araya, D. Paniagua, Z. Camacho-Mora, T. Du, G. R. Golding, G. Leandro-Astorga, C. Rodríguez, C. Quesada-Gómez, *J. Hosp. Infect.* 2018, 99, 475-480.
[53] D. W. Eyre, K. A. Davies, G. Davis, W. N. Fawley, K. E. Dingle, N. De Maio, A. Karas, D. W. Crook, T. E. A. Peto, A. S. Walker, M. H. Wilcox, *Clin. Infect. Dis. Off. Publ. Infect. Dis. Soc. Am.* 2018, 67, 1035-1044.
[54] K. C. Katz, G. R. Golding, K. B. Choi, L. Pelude, K. R. Amaratunga, M. Taljaard, S. Alexandre, J. C. Collet, I. Davis, T. Du, G. A. Evans, C. Frenette, D. Gravel, S. Hota, P. Kibsey, J. M. Langley, B. E. Lee, C. Lemieux, Y. Longtin, D. Mertz, L. M. D. Mieusement, J. Minion, D. L. Moore, M. R. Mulvey, S. Richardson, M. Science, A. E. Simor, P. Stagg, K. N. Suh, G. Taylor, A. Wong, N. Thampi, *CMAJ* 2018, 190, E758-E765.
[55] A. Goorhuis, D. Bakker, J. Corver, S. B. Debast, C. Harmanus, D. W. Notermans, A. A. Bergwerff, F. W. Dekker, E. J. Kuijper, *Clin. Infect. Dis.* 2008, 47, 1162-1170.
[56] M. P. M. Hensgens, A. Goorhuis, C. M. J. van Kinschot, M. J. T. Crobach, C. Harmanus, E. J. Kuijper, *Eur. J. Clin. Microbiol. Infect. Dis.* 2011, 30, 587-593.
[57] D. Bakker, J. Corver, C. Harmanus, A. Goorhuis, E. C. Keessen, W. N. Fawley, M. H. Wilcox, E. J. Kuijper, *J. Clin. Microbiol.* 2010, 48, 3744-3749.
[58] M. C. Wehrhahn, C. Keighley, J. Kurtovic, D. R. Knight, S. Hong, M. L. Hutton, D. Lyras, Q. Wang, R. Leong, T. Borody, M. Edye, T. V. Riley, *Anaerobe* 2019, 55, 117-123.
[59] M. Arvand, A. M. Hauri, N. H. Zaiss, W. Witte, G. Bettge-Weller, *Eurosurveillance* 2009, 14, 19403.
[60] H. Huang, H. Fang, A. Weintraub, C. E. Nord, *Clin. Microbiol. Infect.* 2009, 15, 1170-1173.
[61] A. Calderaro, M. Buttrini, M. Martinelli, C. Gorrini, S. Montecchini, M. C. Medici, M. C. Arcangeletti, F. De Conto, S. Covan, C. Chezzi, *New Microbiol.* 2013, 36, 57-63.
[62] U. Eigner, D. Nörz, S. Reucher, J. Furrer, J. Sun, K. Chu, M. Kolb, N. Hefner, S. Pfefferle, M. Lütgehetmann, *J. Microbiol. Methods* 2020, 172, 105882.
[63] S. D. Belanger, M. Boissinot, N. Clairoux, François. J. Picard, M. G. Bergeron, *J. Clin. Microbiol.* 2003, 41, 730-734.
[64] L. Ganji, M. Azimirad, N. Farzi, M. Alebouyeh, M. H. Shirazi, S. S. Eshraghi, A. Mirshafiey, N. E. Daryani, M. R. Zali, *Arch. Pediatr. Infect. Dis.* 2017, 5, DOI 10.5812/pedinfect.38888.
[65] T. Hink, C.-A. D. Burnham, E. R. Dubberke, *Anaerobe* 2013, 19, 39-43.
[66] R. Pandey, Y. Lu, E. Osman, S. Saxena, Z. Zhang, S. Qian, A. Pollinzi, M. Smieja, Y. Li, L. Soleymani, T. Hoare, *ACS Sens.* 2022, 7, 985-994.
[67] M. Liu, Q. Zhang, Z. Li, J. Gu, J. D. Brennan, Y. Li, *Nat. Commun.* 2016, 7, 12074.
[68] R. Pandey, D. Chang, M. Smieja, T. Hoare, Y. Li, L. Soleymani, *Nat. Chem.* 2021, 13, 895-901.
[69] Y. Chi, M. Shi, Y. Wu, Y. Wu, Y. Chang, M. Liu, *Anal. Methods* 2022, 14, 2244-2248.
[70] S. A. McManus, Y. Li, *J. Mol. Biol.* 2008, 375, 960-968.
[71] W. Chiuman, Y. Li, *J. Mol. Biol.* 2006, 357, 748-754.
[72] W. Chiuman, Y. Li, *PLOS ONE* 2007, 2, e1224.
[73] S. A. Kandadai, Y. Li, *Nucleic Acids Res.* 2005, 33, 7164-7175.
[74] Z. Chen, P. A. Lichtor, A. P. Berliner, J. C. Chen, D. R. Liu, *Nat. Chem.* 2018, 10, 420-427.
[75] J. C. Achenbach, G. A. Jeffries, S. A. McManus, L. P. Billen, Y. Li, *Biochemistry* 2005, 44, 3765-3774.
[76] T. J. Louie, B. Byrne, J. Emery, L. Ward, W. Krulicki, D. Nguyen, K. Wu, K. Cannon, *Clin. Infect. Dis. Off. Publ. Infect. Dis. Soc. Am.* 2015, 60 *Suppl* 2, S91-97.

The invention claimed is:

1. A catalytic nucleic acid for detecting *Clostridium difficile* comprising the sequence selected from the group consisting of SEQ ID NO: 11, 15-16, 19-21, 23, 29-32, 36-37, 39-44, and 47 or a functional fragment or variant thereof, wherein the functional fragment or variant comprises a first domain comprising nucleotides 21-41 of SEQ ID NO: 11 and a second domain comprising nucleotides 61-78 of SEQ ID NO: 11; or the catalytic nucleic acid comprises one of SEQ ID NO: 10, 12, 13, or 14.

2. The catalytic nucleic acid of claim 1, comprising the nucleotide sequence selected from the group consisting of SEQ ID NOs: 10-15, 19, 30, 36, 37, 39-43, and 47.

3. The catalytic nucleic acid of claim 1, comprising the nucleotide sequence selected from the group consisting of SEQ ID NOs: 11, 36, 40-42, and 47.

4. The catalytic nucleic acid of claim 1, wherein the catalytic nucleic acid has a limit-of-detection of about 100 CFU/mL *C. difficile.*

5. The catalytic nucleic acid of claim 1, wherein the catalytic nucleic acid is for cleavage of a nucleic acid substrate.

6. A catalytic nucleic acid probe comprising the catalytic nucleic acid of claim 1 and a detectable substrate.

7. The catalytic nucleic acid probe of claim 6, wherein the detectable substrate comprises the nucleotide sequence of SEQ ID NO: 1 or 76.

8. The catalytic nucleic acid probe of claim 6, wherein the catalytic nucleic acid probe comprises the nucleotide sequence selected from the group consisting of SEQ ID NOs: 48-53 and 70-75.

9. The catalytic nucleic acid probe of claim 6, wherein the detectable substrate comprises a ribonucleotide flanked by a fluorophore modified nucleic acid residue and a quencher modified nucleic acid residue.

10. The catalytic nucleic acid probe of claim 6, wherein the catalytic nucleic acid probe is configured to generate a fluorogenic signal upon contacting *C. difficile.*

11. A biosensor for detecting *C. difficile* comprising the catalytic nucleic acid of claim 1, functionalized on and/or in a material.

12. A method for detecting the presence of *C. difficile* in a sample, the method comprising:

a) combining the sample with the catalytic nucleic acid probe of claim 6 in a liquid to form a mixture;

b) incubating the mixture to allow for a cleavage reaction in which the catalytic nucleic acid cleaves the detectable substrate, thereby releasing a fragment comprising a quencher modified nucleic acid residue to produce a fluorogenic signal;

c) optionally quenching the cleavage reaction;

d) detecting the fluorogenic signal and/or a cleaved fragment;

wherein detecting the fluorogenic signal and/or the cleaved fragment indicates presence of *C. difficile* in the sample.

13. The method of claim 12, wherein a) the liquid is a buffer and, optionally, the buffer comprises about 50 mM $Mg^{2+}$, and/or wherein b) comprises incubating the mixture at about 37° C.

14. The method of claim 13, wherein the buffer is about pH 8.0.

15. The method of claim 12, wherein the quenching of the cleavage reaction comprises adding a quenching buffer to the mixture.

16. The method of claim 15, wherein the quenching buffer comprises EDTA and/or urea.

17. The method of claim 12, wherein the detecting the fluorogenic signal comprises analysis via a fluorescence assay.

18. The method of claim 12, wherein the method detects *C. difficile* infection in a subject.

19. The method of claim 12, wherein the sample is a stool sample.

20. A kit for detecting *C. difficile* in a sample, wherein the kit comprises the catalytic nucleic acid probe of claim 6, and instructions for use of the kit.

* * * * *

SEQUENCE LISTING

```
Sequence total quantity: 76
SEQ ID NO: 1             moltype = DNA  length = 30
FEATURE                  Location/Qualifiers
source                   1..30
                         mol_type = other DNA
                         organism = synthetic construct
```

```
modified_base         13
                      mod_base = OTHER
                      note = dabcyl deoxythymidine
modified_base         14
                      mod_base = OTHER
                      note = adenine ribonucleotide
modified_base         15
                      mod_base = OTHER
                      note = fluorescein deoxythymidine
SEQUENCE: 1
catcagactc cgtataacct cactaccaag                                30

SEQ ID NO: 2          moltype = DNA  length = 35
FEATURE               Location/Qualifiers
source                1..35
                      mol_type = other DNA
                      organism = synthetic construct
SEQUENCE: 2
ggtgtaggga gtttaggttg cttggtagtg aggtt                          35

SEQ ID NO: 3          moltype = DNA  length = 20
FEATURE               Location/Qualifiers
source                1..20
                      mol_type = other DNA
                      organism = synthetic construct
SEQUENCE: 3
caacctaaac tccctacacc                                           20

SEQ ID NO: 4          moltype = DNA  length = 20
FEATURE               Location/Qualifiers
source                1..20
                      mol_type = other DNA
                      note = Note=The 5' deoxycytidine can be attached to a
                       non-amplifiable triethylene glycol linker that can be
                       attached to the 3' deoxyadenosine of SEQ ID NO: 5
                      organism = synthetic construct
SEQUENCE: 4
cgacatctgc ttccacatca                                           20

SEQ ID NO: 5          moltype = DNA  length = 20
FEATURE               Location/Qualifiers
source                1..20
                      mol_type = other DNA
                      note = The 3' deoxyadenosine can be attached through a
                       non-amplifiable triethylene glycol linker that can be
                       attached to the 5' deoxycytidine of SEQ ID NO: 4 or 8
                      organism = synthetic construct
SEQUENCE: 5
aaaaaaaaaa aaaaaaaaaa                                           20

SEQ ID NO: 6          moltype = DNA  length = 20
FEATURE               Location/Qualifiers
source                1..20
                      mol_type = other DNA
                      note = Note=The 5' deoxyguanosine can be attached to a
                       non-amplifiable triethylene glycol linker that can be
                       attached to the 3' deoxyadenosine of SEQ ID NO: 7
                      organism = synthetic construct
SEQUENCE: 6
tgatgtggaa gcagatgtcg                                           20

SEQ ID NO: 7          moltype = DNA  length = 20
FEATURE               Location/Qualifiers
source                1..20
                      mol_type = other DNA
                      note = Note=The 5' thymidine is attached through a
                       non-amplifiable triethylene glycol linker that can be
                       attached to the 3' deoxyguanosine of SEQ ID NO: 6 or 3'
                       thymidine of SEQ ID NO: 9
                      organism = synthetic construct
SEQUENCE: 7
tttttttttt tttttttttt                                           20

SEQ ID NO: 8          moltype = DNA  length = 20
FEATURE               Location/Qualifiers
source                1..20
                      mol_type = other DNA
                      note = Note=The 5' deoxycytidine can be attached through a
                       non-amplifiable triethylene glycol linker that can be
```

```
                         attached to the 3' deoxyadenosine of SEQ ID NO: 5
                         organism = synthetic construct
SEQUENCE: 8
ctaagcctcc gatgacaaga                                              20

SEQ ID NO: 9             moltype = DNA  length = 20
FEATURE                  Location/Qualifiers
source                   1..20
                         mol_type = other DNA
                         note = Note=The 3' thymidine can be attached through a
                          non-amplifiable triethylene glycol linker that can be
                          attached to the 5' thymidine of SEQ ID NO: 7
                         organism = synthetic construct
SEQUENCE: 9
gattcggagg ctactgttct                                              20

SEQ ID NO: 10            moltype = DNA  length = 90
FEATURE                  Location/Qualifiers
source                   1..90
                         mol_type = other DNA
                         organism = synthetic construct
SEQUENCE: 10
caacctaaac tccctacacc ccaaactggt tatgaaggta tgggttatat gagtcaagaa  60
tgagatactg tgatgtggaa gcagatgtcg                                   90

SEQ ID NO: 11            moltype = DNA  length = 90
FEATURE                  Location/Qualifiers
source                   1..90
                         mol_type = other DNA
                         organism = synthetic construct
SEQUENCE: 11
caacctaaac tccctacacc acattaagat agaggttata ctgggtcaca gatagtctag  60
gtaggttatc tgatgtggaa gcagatgtcg                                   90

SEQ ID NO: 12            moltype = DNA  length = 88
FEATURE                  Location/Qualifiers
source                   1..88
                         mol_type = other DNA
                         organism = synthetic construct
SEQUENCE: 12
caacctaaac tccctacacc gttcttagta tatagaatta tttagttaat gagttatcgg  60
acgacaaatg atgtggaagc agatgtcg                                     88

SEQ ID NO: 13            moltype = DNA  length = 89
FEATURE                  Location/Qualifiers
source                   1..89
                         mol_type = other DNA
                         organism = synthetic construct
SEQUENCE: 13
caacctaaac tccctacacc cctaagataa atggatccta gacccacagt gatgattaac  60
ggcgatattt gatgtggaag cagatgtcg                                    89

SEQ ID NO: 14            moltype = DNA  length = 89
FEATURE                  Location/Qualifiers
source                   1..89
                         mol_type = other DNA
                         organism = synthetic construct
SEQUENCE: 14
caacctaaac tccctacacc gttctcagaa caatcaattc aaaattttag taaggttaac  60
ggctacatat gatgtggaag cagatgtcg                                    89

SEQ ID NO: 15            moltype = DNA  length = 85
FEATURE                  Location/Qualifiers
source                   1..85
                         mol_type = other DNA
                         organism = synthetic construct
SEQUENCE: 15
caacctaaac tccctacacc acattaagat agaggttata ctgggtcaca gatagtctag  60
gtaggttatc tgatgtggaa gcaga                                        85

SEQ ID NO: 16            moltype = DNA  length = 80
FEATURE                  Location/Qualifiers
source                   1..80
                         mol_type = other DNA
                         organism = synthetic construct
SEQUENCE: 16
caacctaaac tccctacacc acattaagat agaggttata ctgggtcaca gatagtctag  60
gtaggttatc tgatgtggaa                                              80
```

```
SEQ ID NO: 17          moltype = DNA  length = 75
FEATURE                Location/Qualifiers
source                 1..75
                       mol_type = other DNA
                       organism = synthetic construct
SEQUENCE: 17
caacctaaac tccctacacc acattaagat agaggttata ctgggtcaca gatagtctag  60
gtaggttatc tgatg                                                   75

SEQ ID NO: 18          moltype = DNA  length = 70
FEATURE                Location/Qualifiers
source                 1..70
                       mol_type = other DNA
                       organism = synthetic construct
SEQUENCE: 18
caacctaaac tccctacacc acattaagat agaggttata ctgggtcaca gatagtctag  60
gtaggttatc                                                         70

SEQ ID NO: 19          moltype = DNA  length = 75
FEATURE                Location/Qualifiers
source                 1..75
                       mol_type = other DNA
                       organism = synthetic construct
SEQUENCE: 19
taaactccct acaccacatt aagatagagg ttatactggg tcacagatag tctaggtagg  60
ttatctgatg tggaa                                                   75

SEQ ID NO: 20          moltype = DNA  length = 70
FEATURE                Location/Qualifiers
source                 1..70
                       mol_type = other DNA
                       organism = synthetic construct
SEQUENCE: 20
tccctacacc acattaagat agaggttata ctgggtcaca gatagtctag gtaggttatc  60
tgatgtggaa                                                         70

SEQ ID NO: 21          moltype = DNA  length = 65
FEATURE                Location/Qualifiers
source                 1..65
                       mol_type = other DNA
                       organism = synthetic construct
SEQUENCE: 21
acaccacatt aagatagagg ttatactggg tcacagatag tctaggtagg ttatctgatg  60
tggaa                                                              65

SEQ ID NO: 22          moltype = DNA  length = 60
FEATURE                Location/Qualifiers
source                 1..60
                       mol_type = other DNA
                       organism = synthetic construct
SEQUENCE: 22
acattaagat agaggttata ctgggtcaca gatagtctag gtaggttatc tgatgtggaa  60

SEQ ID NO: 23          moltype = DNA  length = 68
FEATURE                Location/Qualifiers
source                 1..68
                       mol_type = other DNA
                       organism = synthetic construct
SEQUENCE: 23
tccctacacc acattaagat agaggttata ctgggtcaca gatagtctag gtaggttatc  60
tgatgtgg                                                           68

SEQ ID NO: 24          moltype = DNA  length = 63
FEATURE                Location/Qualifiers
source                 1..63
                       mol_type = other DNA
                       organism = synthetic construct
SEQUENCE: 24
tccctacatt aagatagagg ttatactggg tcacagatag tctaggtagg ttatctgatg  60
tgg                                                                63

SEQ ID NO: 25          moltype = DNA  length = 63
FEATURE                Location/Qualifiers
source                 1..63
                       mol_type = other DNA
                       organism = synthetic construct
SEQUENCE: 25
tccctacacc aagatagagg ttatactggg tcacagatag tctaggtagg ttatctgatg  60
tgg                                                                63
```

```
SEQ ID NO: 26          moltype = DNA  length = 63
FEATURE                Location/Qualifiers
source                 1..63
                       mol_type = other DNA
                       organism = synthetic construct
SEQUENCE: 26
tccctacacc acattagagg ttatactggg tcacagatag tctaggtagg ttatctgatg  60
tgg                                                                63

SEQ ID NO: 27          moltype = DNA  length = 63
FEATURE                Location/Qualifiers
source                 1..63
                       mol_type = other DNA
                       organism = synthetic construct
SEQUENCE: 27
tccctacacc acattaagat ttatactggg tcacagatag tctaggtagg ttatctgatg  60
tgg                                                                63

SEQ ID NO: 28          moltype = DNA  length = 63
FEATURE                Location/Qualifiers
source                 1..63
                       mol_type = other DNA
                       organism = synthetic construct
SEQUENCE: 28
tccctacacc acattaagat agaggctggg tcacagatag tctaggtagg ttatctgatg  60
tgg                                                                63

SEQ ID NO: 29          moltype = DNA  length = 63
FEATURE                Location/Qualifiers
source                 1..63
                       mol_type = other DNA
                       organism = synthetic construct
SEQUENCE: 29
tccctacacc acattaagat agaggttata tcacagatag tctaggtagg ttatctgatg  60
tgg                                                                63

SEQ ID NO: 30          moltype = DNA  length = 63
FEATURE                Location/Qualifiers
source                 1..63
                       mol_type = other DNA
                       organism = synthetic construct
SEQUENCE: 30
tccctacacc acattaagat agaggttata ctggggatag tctaggtagg ttatctgatg  60
tgg                                                                63

SEQ ID NO: 31          moltype = DNA  length = 63
FEATURE                Location/Qualifiers
source                 1..63
                       mol_type = other DNA
                       organism = synthetic construct
SEQUENCE: 31
tccctacacc acattaagat agaggttata ctgggtcaca tctaggtagg ttatctgatg  60
tgg                                                                63

SEQ ID NO: 32          moltype = DNA  length = 63
FEATURE                Location/Qualifiers
source                 1..63
                       mol_type = other DNA
                       organism = synthetic construct
SEQUENCE: 32
tccctacacc acattaagat agaggttata ctgggtcaca gataggtagg ttatctgatg  60
tgg                                                                63

SEQ ID NO: 33          moltype = DNA  length = 63
FEATURE                Location/Qualifiers
source                 1..63
                       mol_type = other DNA
                       organism = synthetic construct
SEQUENCE: 33
tccctacacc acattaagat agaggttata ctgggtcaca gatagtctag ttatctgatg  60
tgg                                                                63

SEQ ID NO: 34          moltype = DNA  length = 63
FEATURE                Location/Qualifiers
source                 1..63
                       mol_type = other DNA
                       organism = synthetic construct
SEQUENCE: 34
```

```
tccctacacc acattaagat agaggttata ctgggtcaca gatagtctag gtaggtgatg  60
tgg                                                                63

SEQ ID NO: 35          moltype = DNA  length = 63
FEATURE                Location/Qualifiers
source                 1..63
                       mol_type = other DNA
                       organism = synthetic construct
SEQUENCE: 35
tccctacacc acattaagat agaggttata ctgggtcaca gatagtctag gtaggttatc  60
tgg                                                                63

SEQ ID NO: 36          moltype = DNA  length = 59
FEATURE                Location/Qualifiers
source                 1..59
                       mol_type = other DNA
                       organism = synthetic construct
SEQUENCE: 36
tccctacacc acattaagat agaggttata cgatagtcta ggtaggttat ctgatgtgg   59

SEQ ID NO: 37          moltype = DNA  length = 100
FEATURE                Location/Qualifiers
source                 1..100
                       mol_type = other DNA
                       organism = synthetic construct
SEQUENCE: 37
caacctaaac tccctacacc acattaagat agaggttata ctgggtcaca gatagtctag  60
gtaggttatc tgatgtggaa tcttgtcatc ggaggcttag                        100

SEQ ID NO: 38          moltype = DNA  length = 90
FEATURE                Location/Qualifiers
source                 1..90
                       mol_type = other DNA
                       organism = synthetic construct
SEQUENCE: 38
caacctaaac tccctacacc acattaagcg agaggttata ctgggtcaca gatagtctag  60
gtaggttatc tgatgtggaa gcagatgtcg                                   90

SEQ ID NO: 39          moltype = DNA  length = 90
FEATURE                Location/Qualifiers
source                 1..90
                       mol_type = other DNA
                       organism = synthetic construct
SEQUENCE: 39
caacctaaac tccctacacc acattaagcg agaggttata ctgggtcaca gatagtctag  60
gtaggttcgc tgatgtggaa gcagatgtcg                                   90

SEQ ID NO: 40          moltype = DNA  length = 90
FEATURE                Location/Qualifiers
source                 1..90
                       mol_type = other DNA
                       organism = synthetic construct
SEQUENCE: 40
caacctaaac tccctacacc acattaagaa agaggttata ctgggtcaca gatagtctag  60
gtaggttttc tgatgtggaa gcagatgtcg                                   90

SEQ ID NO: 41          moltype = DNA  length = 59
FEATURE                Location/Qualifiers
source                 1..59
                       mol_type = other DNA
                       organism = synthetic construct
SEQUENCE: 41
tccctacacc acattaagat agaggttata cttttttttt tgtaggttat ctgatgtgg   59

SEQ ID NO: 42          moltype = DNA  length = 58
FEATURE                Location/Qualifiers
source                 1..58
                       mol_type = other DNA
                       organism = synthetic construct
SEQUENCE: 42
tccctacacc acattaagat agaggttata cttttttttt gtaggttatc tgatgtgg    58

SEQ ID NO: 43          moltype = DNA  length = 57
FEATURE                Location/Qualifiers
source                 1..57
                       mol_type = other DNA
                       organism = synthetic construct
SEQUENCE: 43
tccctacacc acattaagat agaggttata cttttttttg taggttatct gatgtgg     57
```

```
SEQ ID NO: 44          moltype = DNA  length = 56
FEATURE                Location/Qualifiers
source                 1..56
                       mol_type = other DNA
                       organism = synthetic construct
SEQUENCE: 44
tccctacacc acattaagat agaggttata cttttttgt aggttatctg atgtgg      56

SEQ ID NO: 45          moltype = DNA  length = 55
FEATURE                Location/Qualifiers
source                 1..55
                       mol_type = other DNA
                       organism = synthetic construct
SEQUENCE: 45
tccctacacc acattaagat agaggttata cttttttgta ggttatctga tgtgg       55

SEQ ID NO: 46          moltype = DNA  length = 54
FEATURE                Location/Qualifiers
source                 1..54
                       mol_type = other DNA
                       organism = synthetic construct
SEQUENCE: 46
tccctacacc acattaagat agaggttata ctttttgtag gttatctgat gtgg        54

SEQ ID NO: 47          moltype = DNA  length = 58
FEATURE                Location/Qualifiers
source                 1..58
                       mol_type = other DNA
                       organism = synthetic construct
SEQUENCE: 47
tccctacacc acattaagaa agaggttata cttttttttt gtaggttttc tgatgtgg    58

SEQ ID NO: 48          moltype = DNA  length = 120
FEATURE                Location/Qualifiers
source                 1..120
                       mol_type = other DNA
                       organism = synthetic construct
modified_base          13
                       mod_base = OTHER
                       note = dabcyl deoxythymidine
modified_base          14
                       mod_base = OTHER
                       note = adenine ribonucleotide
modified_base          15
                       mod_base = OTHER
                       note = fluorescein deoxythymidine
SEQUENCE: 48
catcagactc cgtataacct cactaccaag caacctaaac tccctacacc acattaagat  60
agaggttata ctgggtcaca gatagtctag gtaggttatc tgatgtggaa gcagatgtcg  120

SEQ ID NO: 49          moltype = DNA  length = 89
FEATURE                Location/Qualifiers
source                 1..89
                       mol_type = other DNA
                       organism = synthetic construct
modified_base          13
                       mod_base = OTHER
                       note = dabcyl deoxythymidine
modified_base          14
                       mod_base = OTHER
                       note = adenine ribonucleotide
modified_base          15
                       mod_base = OTHER
                       note = fluorescein deoxythymidine
SEQUENCE: 49
catcagactc cgtataacct cactaccaag tccctacacc acattaagat agaggttata  60
cgatagtcta ggtaggttat ctgatgtgg                                    89

SEQ ID NO: 50          moltype = DNA  length = 120
FEATURE                Location/Qualifiers
source                 1..120
                       mol_type = other DNA
                       organism = synthetic construct
modified_base          13
                       mod_base = OTHER
                       note = dabcyl deoxythymidine
modified_base          14
                       mod_base = OTHER
```

```
                         note = adenine ribonucleotide
modified_base            15
                         mod_base = OTHER
                         note = fluorescein deoxythymidine
SEQUENCE: 50
catcagactc cgtataacct cactaccaag caacctaaac tccctacacc acattaagaa  60
agaggttata ctgggtcaca gatagtctag gtaggttttc tgatgtggaa gcagatgtcg  120

SEQ ID NO: 51            moltype = DNA  length = 89
FEATURE                  Location/Qualifiers
source                   1..89
                         mol_type = other DNA
                         organism = synthetic construct
modified_base            13
                         mod_base = OTHER
                         note = dabcyl deoxythymidine
modified_base            14
                         mod_base = OTHER
                         note = adenine ribonucleotide
modified_base            15
                         mod_base = OTHER
                         note = fluorescein deoxythymidine
SEQUENCE: 51
catcagactc cgtataacct cactaccaag tccctacacc acattaagat agaggttata  60
cttttttttt tgtaggttat ctgatgtgg                                    89

SEQ ID NO: 52            moltype = DNA  length = 88
FEATURE                  Location/Qualifiers
source                   1..88
                         mol_type = other DNA
                         organism = synthetic construct
modified_base            13
                         mod_base = OTHER
                         note = dabcyl deoxythymidine
modified_base            14
                         mod_base = OTHER
                         note = adenine ribonucleotide
modified_base            15
                         mod_base = OTHER
                         note = fluorescein deoxythymidine
SEQUENCE: 52
catcagactc cgtataacct cactaccaag tccctacacc acattaagat agaggttata  60
cttttttttt gtaggttatc tgatgtgg                                     88

SEQ ID NO: 53            moltype = DNA  length = 88
FEATURE                  Location/Qualifiers
source                   1..88
                         mol_type = other DNA
                         organism = synthetic construct
modified_base            13
                         mod_base = OTHER
                         note = dabcyl deoxythymidine
modified_base            14
                         mod_base = OTHER
                         note = adenine ribonucleotide
modified_base            15
                         mod_base = OTHER
                         note = fluorescein deoxythymidine
SEQUENCE: 53
catcagactc cgtataacct cactaccaag tccctacacc acattaagaa agaggttata  60
cttttttttt gtaggttttc tgatgtgg                                     88

SEQ ID NO: 54            moltype = DNA  length = 100
FEATURE                  Location/Qualifiers
source                   1..100
                         mol_type = other DNA
                         organism = synthetic construct
modified_base            13
                         mod_base = OTHER
                         note = dabcyl deoxythymidine
modified_base            14
                         mod_base = OTHER
                         note = adenine ribonucleotide
modified_base            15
                         mod_base = OTHER
                         note = fluorescein deoxythymidine
misc_feature             31..70
                         note = n is a, c, g, or t
SEQUENCE: 54
```

-continued

```
catcagactc cgtataacct cactaccaag nnnnnnnnnn nnnnnnnnnn nnnnnnnnnn  60
nnnnnnnnnn nnnnnnnnnn tgatgtggaa gcagatgtcg                        100

SEQ ID NO: 55          moltype = DNA  length = 50
FEATURE                Location/Qualifiers
source                 1..50
                       mol_type = other DNA
                       organism = synthetic construct
SEQUENCE: 55
ccaaactggt tatgaaggta tgggttatat gagtcaagaa tgagatactg             50

SEQ ID NO: 56          moltype = DNA  length = 50
FEATURE                Location/Qualifiers
source                 1..50
                       mol_type = other DNA
                       organism = synthetic construct
SEQUENCE: 56
acattaagat agaggttata ctgggtcaca gatagtctag gtaggttatc             50

SEQ ID NO: 57          moltype = DNA  length = 48
FEATURE                Location/Qualifiers
source                 1..48
                       mol_type = other DNA
                       organism = synthetic construct
SEQUENCE: 57
gttcttagta tatagaatta tttagttaat gagttatcgg acgacaaa               48

SEQ ID NO: 58          moltype = DNA  length = 49
FEATURE                Location/Qualifiers
source                 1..49
                       mol_type = other DNA
                       organism = synthetic construct
SEQUENCE: 58
cctaagataa atggatccta gacccacagt gatgattaac ggcgatatt              49

SEQ ID NO: 59          moltype = DNA  length = 49
FEATURE                Location/Qualifiers
source                 1..49
                       mol_type = other DNA
                       organism = synthetic construct
SEQUENCE: 59
gttctcagaa caatcaattc aaaattttag taaggttaac ggctacata              49

SEQ ID NO: 60          moltype = DNA  length = 60
FEATURE                Location/Qualifiers
source                 1..60
                       mol_type = other DNA
                       organism = synthetic construct
SEQUENCE: 60
acattaagat agaggttata ctgggtcaca gatagtctag gtaggttatc tgatgtggaa  60

SEQ ID NO: 61          moltype = DNA  length = 59
FEATURE                Location/Qualifiers
source                 1..59
                       mol_type = other DNA
                       organism = synthetic construct
SEQUENCE: 61
acattaagaa agaggttata cggagtgact gatagtcaag gtaggttttc tgatgtgga   59

SEQ ID NO: 62          moltype = DNA  length = 60
FEATURE                Location/Qualifiers
source                 1..60
                       mol_type = other DNA
                       organism = synthetic construct
SEQUENCE: 62
acattaagag agaggttata ctgggttaca gatagtctag gtaggttctc tgatttgtaa  60

SEQ ID NO: 63          moltype = DNA  length = 60
FEATURE                Location/Qualifiers
source                 1..60
                       mol_type = other DNA
                       organism = synthetic construct
SEQUENCE: 63
acattaagat ggaggttata ctgggtcaca gataatgaag gtaggtcatc tgatgtggac  60

SEQ ID NO: 64          moltype = DNA  length = 60
FEATURE                Location/Qualifiers
source                 1..60
                       mol_type = other DNA
```

```
                       organism = synthetic construct
SEQUENCE: 64
ccattaagaa agaggttata ctgggtcaca tatagtctag gtaggttttc tgatgtggta  60

SEQ ID NO: 65          moltype = DNA  length = 60
FEATURE                Location/Qualifiers
source                 1..60
                       mol_type = other DNA
                       organism = synthetic construct
SEQUENCE: 65
acattaagat tgaggttata ctgggtcaaa gataaactag gtaggtaatc tgatgtggaa  60

SEQ ID NO: 66          moltype = DNA  length = 60
FEATURE                Location/Qualifiers
source                 1..60
                       mol_type = other DNA
                       organism = synthetic construct
SEQUENCE: 66
acattacgat agaggttata ctgggtcaca catagcgtag gtagggtatc ggatgtggaa  60

SEQ ID NO: 67          moltype = DNA  length = 60
FEATURE                Location/Qualifiers
source                 1..60
                       mol_type = other DNA
                       organism = synthetic construct
SEQUENCE: 67
acattaagat ggaggttata ctcggtcact gatagtctcg gtaggtcttc tgatgtggaa  60

SEQ ID NO: 68          moltype = DNA  length = 60
FEATURE                Location/Qualifiers
source                 1..60
                       mol_type = other DNA
                       organism = synthetic construct
SEQUENCE: 68
acattaagat tgaggttata ctaggtcaca gatagtctag gtaggtaatc tgttgtggaa  60

SEQ ID NO: 69          moltype = DNA  length = 10
FEATURE                Location/Qualifiers
source                 1..10
                       mol_type = other DNA
                       organism = synthetic construct
SEQUENCE: 69
gatagtctag                                                         10

SEQ ID NO: 70          moltype = DNA  length = 120
FEATURE                Location/Qualifiers
source                 1..120
                       mol_type = other DNA
                       organism = synthetic construct
modified_base          14
                       mod_base = OTHER
                       note = adenine ribonucleotide
SEQUENCE: 70
catcagactc cgtataacct cactaccaag caacctaaac tccctacacc acattaagat  60
agaggttata ctgggtcaca gatagtctag gtaggttatc tgatgtggaa gcagatgtcg  120

SEQ ID NO: 71          moltype = DNA  length = 89
FEATURE                Location/Qualifiers
source                 1..89
                       mol_type = other DNA
                       organism = synthetic construct
modified_base          14
                       mod_base = OTHER
                       note = adenine ribonucleotide
SEQUENCE: 71
catcagactc cgtataacct cactaccaag tccctacacc acattaagat agaggttata  60
cgatagtcta ggtaggttat ctgatgtgg                                    89

SEQ ID NO: 72          moltype = DNA  length = 120
FEATURE                Location/Qualifiers
source                 1..120
                       mol_type = other DNA
                       organism = synthetic construct
modified_base          14
                       mod_base = OTHER
                       note = adenine ribonucleotide
SEQUENCE: 72
catcagactc cgtataacct cactaccaag caacctaaac tccctacacc acattaagaa  60
agaggttata ctgggtcaca gatagtctag gtaggttttc tgatgtggaa gcagatgtcg  120
```

-continued

```
SEQ ID NO: 73           moltype = DNA  length = 89
FEATURE                 Location/Qualifiers
source                  1..89
                        mol_type = other DNA
                        organism = synthetic construct
modified_base           14
                        mod_base = OTHER
                        note = adenine ribonucleotide
SEQUENCE: 73
catcagactc cgtataacct cactaccaag tccctacacc acattaagat agaggttata  60
cttttttttt tgtaggttat ctgatgtgg                                     89

SEQ ID NO: 74           moltype = DNA  length = 88
FEATURE                 Location/Qualifiers
source                  1..88
                        mol_type = other DNA
                        organism = synthetic construct
modified_base           14
                        mod_base = OTHER
                        note = adenine ribonucleotide
SEQUENCE: 74
catcagactc cgtataacct cactaccaag tccctacacc acattaagat agaggttata  60
cttttttttt gtaggttatc tgatgtgg                                      88

SEQ ID NO: 75           moltype = DNA  length = 88
FEATURE                 Location/Qualifiers
source                  1..88
                        mol_type = other DNA
                        organism = synthetic construct
modified_base           14
                        mod_base = OTHER
                        note = adenine ribonucleotide
SEQUENCE: 75
catcagactc cgtataacct cactaccaag tccctacacc acattaagaa agaggttata  60
cttttttttt gtaggttttc tgatgtgg                                      88

SEQ ID NO: 76           moltype = DNA  length = 30
FEATURE                 Location/Qualifiers
source                  1..30
                        mol_type = other DNA
                        organism = synthetic construct
modified_base           14
                        mod_base = OTHER
                        note = adenine ribonucleotide
SEQUENCE: 76
catcagactc cgtataacct cactaccaag                                    30
```